United States Patent
Fulton, III

(10) Patent No.: US 12,263,293 B2
(45) Date of Patent: Apr. 1, 2025

(54) SYSTEM AND METHOD OF ORAL TREATMENT AND RELIEVING STRESS

(71) Applicant: Nfinium Vascular Technologies, LLC, Grand Junction, CO (US)

(72) Inventor: Richard Eustis Fulton, III, Grand Junction, CO (US)

(73) Assignee: Nfinium Vascular Technologies, LLC, Grand Junction, CO (US)

( * ) Notice: Subject to any disclaimer, the term of this patent is extended or adjusted under 35 U.S.C. 154(b) by 1098 days.

(21) Appl. No.: 17/061,339

(22) Filed: Oct. 1, 2020

(65) Prior Publication Data
US 2021/0085837 A1 Mar. 25, 2021

Related U.S. Application Data

(63) Continuation-in-part of application No. 15/945,495, filed on Apr. 4, 2018, now abandoned, which is a continuation of application No. 15/084,230, filed on Mar. 29, 2016, now abandoned, which is a continuation-in-part of application No. 14/504,518, filed on Oct. 2, 2014, now Pat. No. 9,545,195.
(Continued)

(51) Int. Cl.
| | |
|---|---|
| *A61C 17/08* | (2006.01) |
| *A61B 1/015* | (2006.01) |
| *A61B 1/24* | (2006.01) |
| *A61B 1/32* | (2006.01) |
| *A61C 5/90* | (2017.01) |
| *A61M 1/00* | (2006.01) |

(52) U.S. Cl.
CPC ............... *A61M 1/84* (2021.05); *A61B 1/015* (2013.01); *A61B 1/24* (2013.01); *A61B 1/32* (2013.01); *A61C 5/90* (2017.02); *A61C 17/08* (2019.05)

(58) Field of Classification Search
CPC . A61M 1/84; A61C 5/90; A61C 17/08; A61B 1/015; A61B 1/24; A61B 1/32; A63B 23/032
See application file for complete search history.

(56) References Cited

U.S. PATENT DOCUMENTS

| | | |
|---|---|---|
| 160,604 A | 3/1875 | Lewis |
| 637,970 A | 11/1899 | Nyman |
| (Continued) | | |

OTHER PUBLICATIONS

Official Action for Chinese Patent Application No. 201480066016.0, dated Dec. 7, 2017.
(Continued)

*Primary Examiner* — Ralph A Lewis
(74) *Attorney, Agent, or Firm* — Sheridan Ross P.C.

(57) ABSTRACT

A device, system, and method for relaxing jaw muscles of a user. The device has a tooth engaging portion which operates by stretching the users jaw in the open position, thereby simulating a yawn. The device may be optimized to be used as a dental tool having a suction end. The system may include a computer program having stored or downloaded guided meditation programs, soothing sounds, inspirational messages, or similar. The system may also include a reminder that reminds the user to perform the task via a smart device. Further, the device may be used as a method of preventing or treating migraine headaches by relieving stress and relaxing the user.

18 Claims, 42 Drawing Sheets

Related U.S. Application Data

(60) Provisional application No. 62/178,129, filed on Mar. 30, 2015, provisional application No. 62/274,625, filed on Jan. 4, 2016, provisional application No. 61/961,106, filed on Oct. 2, 2013, provisional application No. 61/967,319, filed on Mar. 13, 2014, provisional application No. 61/997,780, filed on Jun. 9, 2014, provisional application No. 62/966,475, filed on Jan. 27, 2020.

(56) References Cited

U.S. PATENT DOCUMENTS

| | | | |
|---|---|---|---|
| 1,042,133 | A | 10/1912 | Marshall |
| 1,053,965 | A | 2/1913 | Barghausen et al. |
| 1,466,559 | A | 8/1923 | Purdy |
| 1,557,744 | A | 10/1925 | Tobriner |
| 1,731,322 | A | 10/1929 | Riddle |
| 1,930,712 | A | 10/1933 | Girvin |
| 3,090,122 | A | 5/1963 | Erickson |
| 3,091,859 | A | 6/1963 | Baughn |
| 3,101,543 | A | 8/1963 | Baughn |
| 3,802,081 | A | 4/1974 | Rogers |
| 4,112,934 | A | 9/1978 | Rizk |
| 4,158,916 | A | 6/1979 | Adler |
| 4,259,067 | A | 3/1981 | Nelson |
| 4,259,068 | A | 3/1981 | Stephens |
| 5,431,610 | A * | 7/1995 | Miller ............... A63B 23/032 482/122 |
| 5,462,435 | A | 10/1995 | Young |
| 5,588,836 | A | 12/1996 | Landis et al. |
| 5,931,670 | A | 8/1999 | Davis |
| 6,030,217 | A | 2/2000 | Fletcher |
| 6,213,772 | B1 | 4/2001 | Costello |
| 9,545,195 | B2 | 1/2017 | Fulton, III |
| 2006/0008764 | A1 | 1/2006 | Abo |
| 2007/0078294 | A1 * | 4/2007 | Jain ............... A61M 21/00 600/28 |
| 2007/0082319 | A1 | 4/2007 | Fletcher et al. |
| 2010/0305510 | A1 | 12/2010 | Spinoza |
| 2016/0270878 | A1 | 9/2016 | Fulton, III |
| 2018/0289869 | A1 | 10/2018 | Fulton, III |

OTHER PUBLICATIONS

Official Action (with English translation) for Chinese Patent Application No. 201480066016.0, dated Jun. 3, 2019, 11 pages.

International Search Report and Written Opinion for International (PCT) Patent Application No. PCT/US2014/058904, dated Jan. 7, 2015, 16 pages.

Extended European Search Report for European Patent Application No. 14851077.9, dated Aug. 19, 2016, 7 pages.

Notice of Allowance for European Patent Application No. 14851077.9, dated Sep. 18, 2018, 5 pages.

International Search Report and Written Opinion for International (PCT) Patent Application No. PCT/US2016/024773, dated Sep. 2, 2016, 20 pages.

Official Action for U.S. Appl. No. 14/504,518, filed Apr. 1, 2016, 12 pages.

Official Action for U.S. Appl. No. 14/504,518, filed Jul. 1, 2016, 5 pages.

Notice of Allowance for U.S. Appl. No. 14/504,518, filed Aug. 29, 2016, 6 pages.

Official Action for U.S. Appl. No. 14/504,518, filed Jan. 4, 2016, 10 pages.

Notice of Allowance for U.S. Appl. No. 14/504,518, filed Dec. 1, 2016, 2 pages.

Official Action for U.S. Appl. No. 15/084,230, filed Oct. 5, 2017, 13 pages.

Official Action for U.S. Appl. No. 15/945,495, filed Apr. 1, 2020, 6 pages.

* cited by examiner

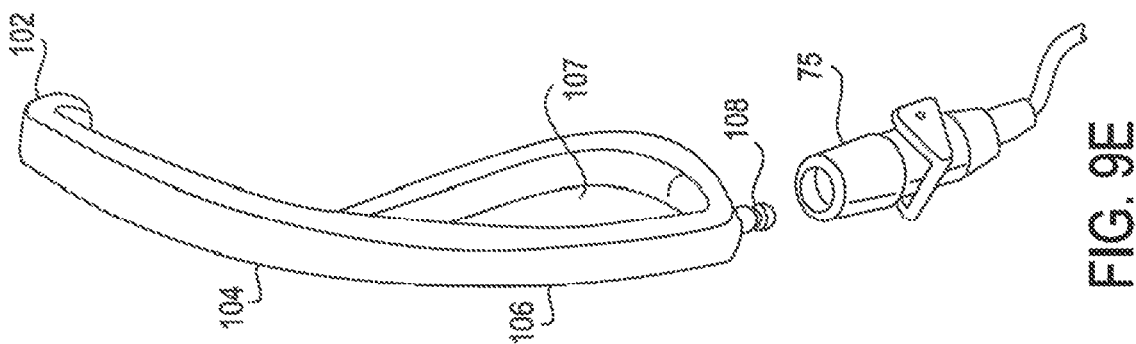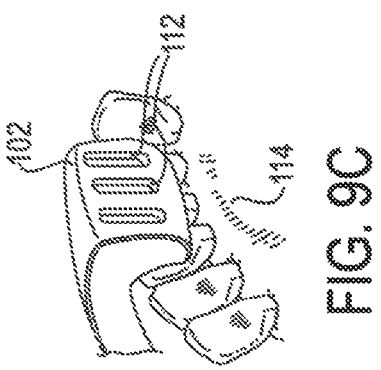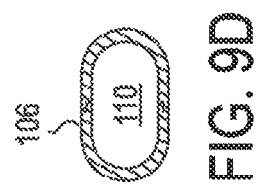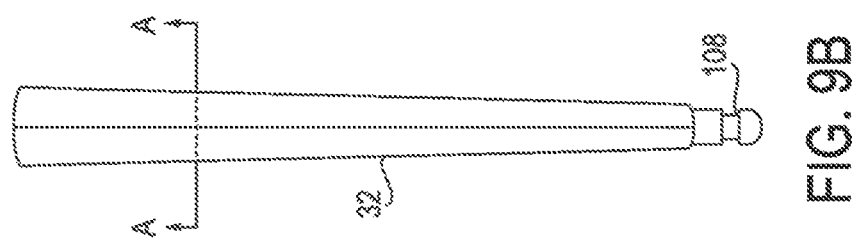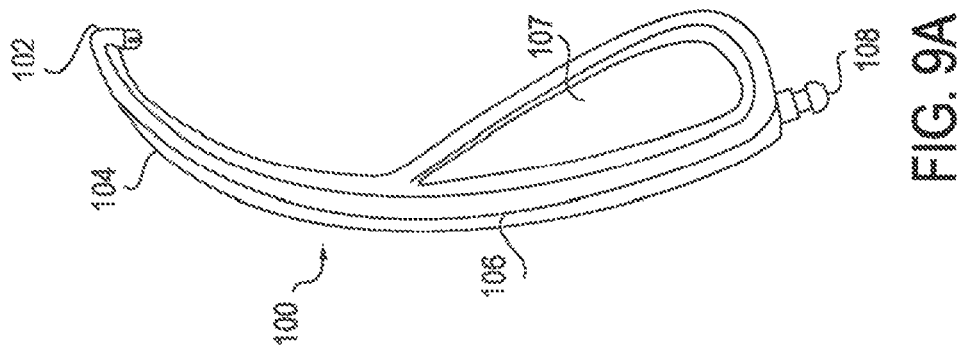

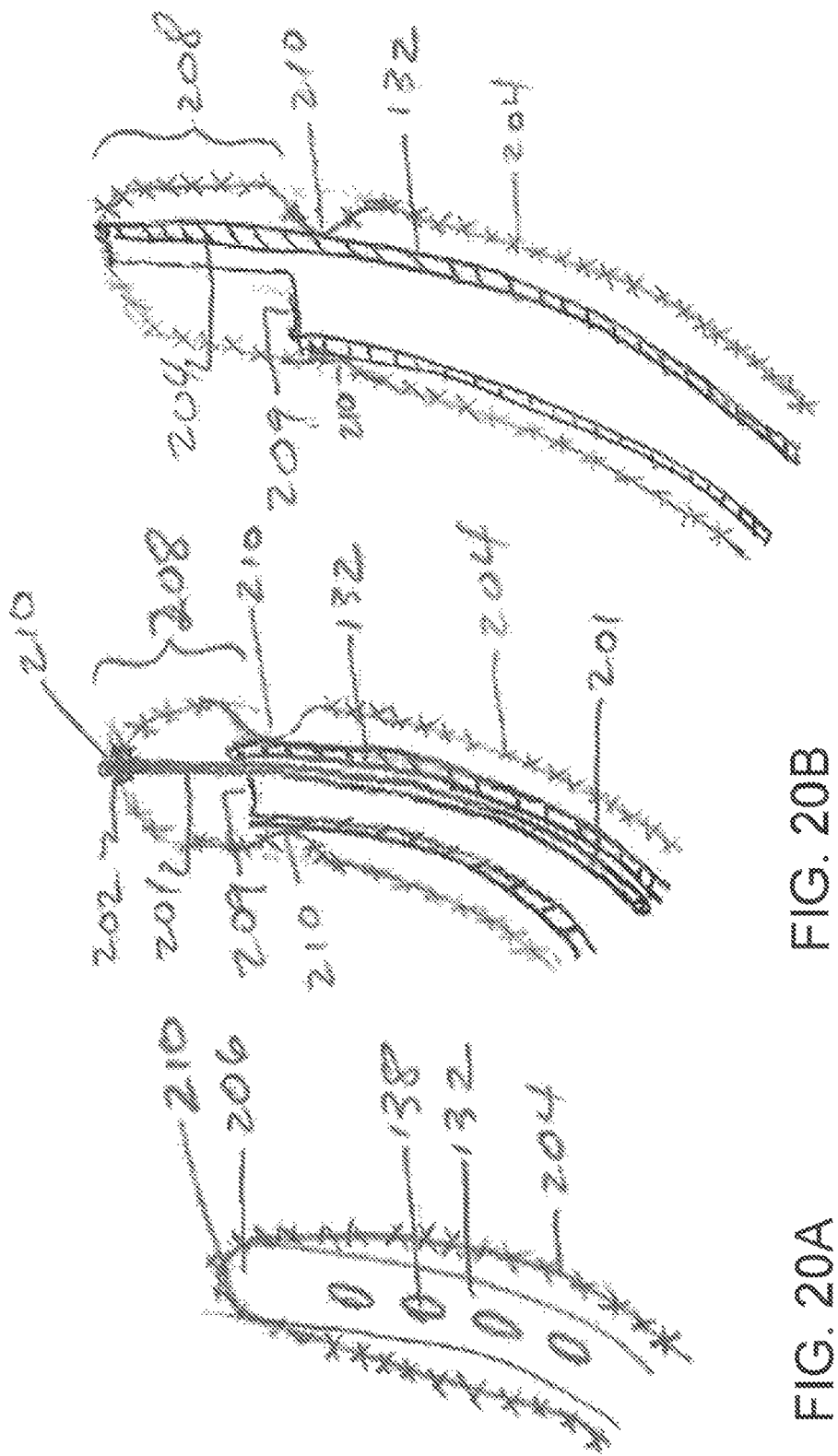

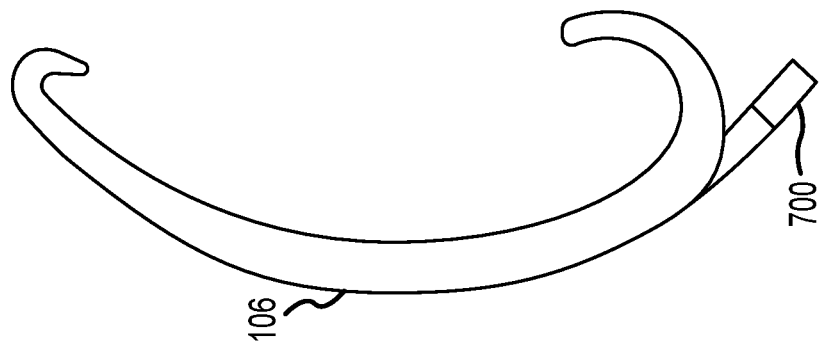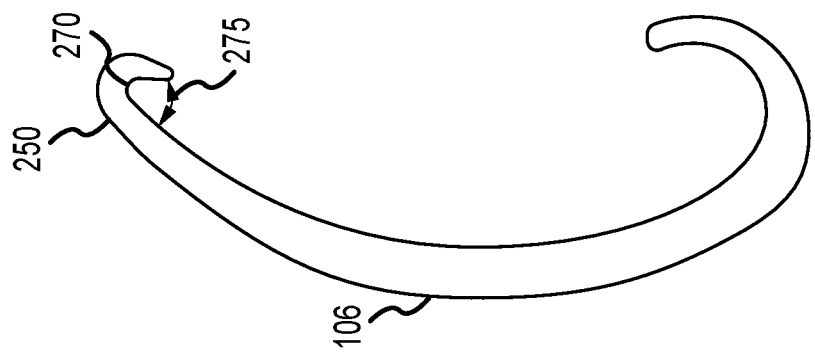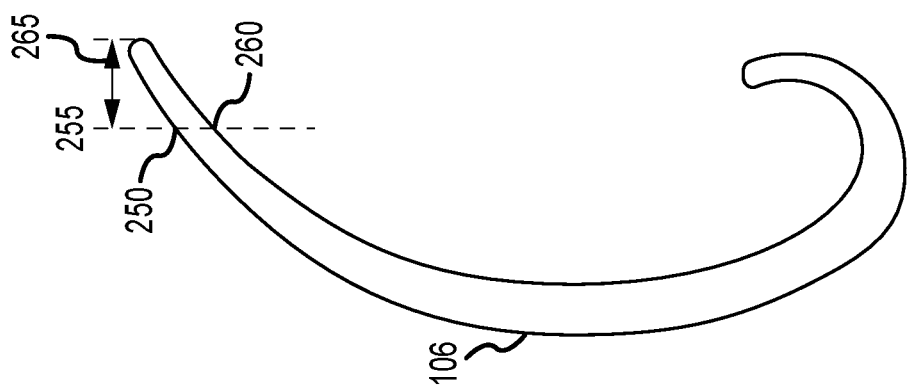

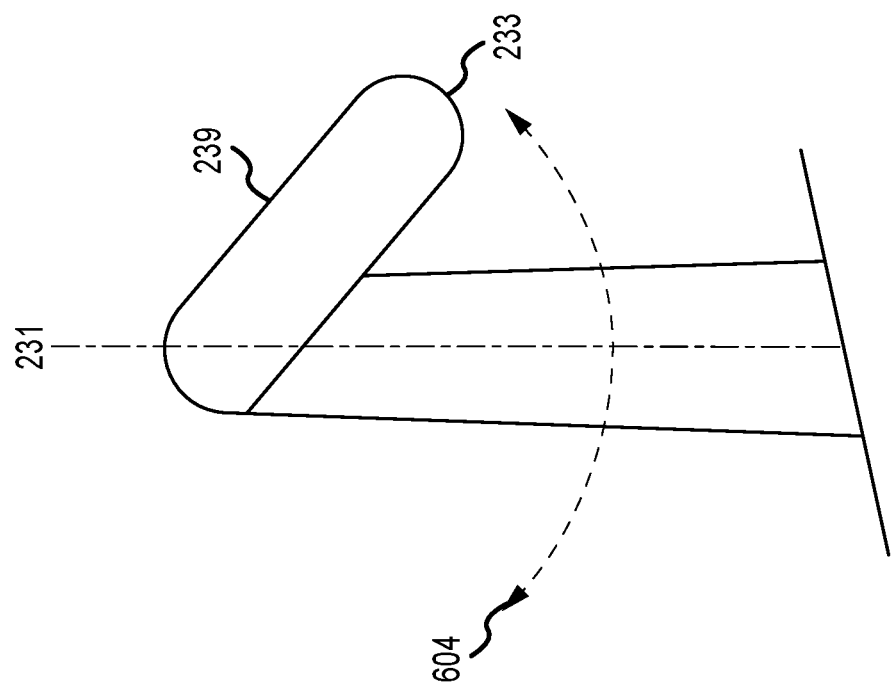
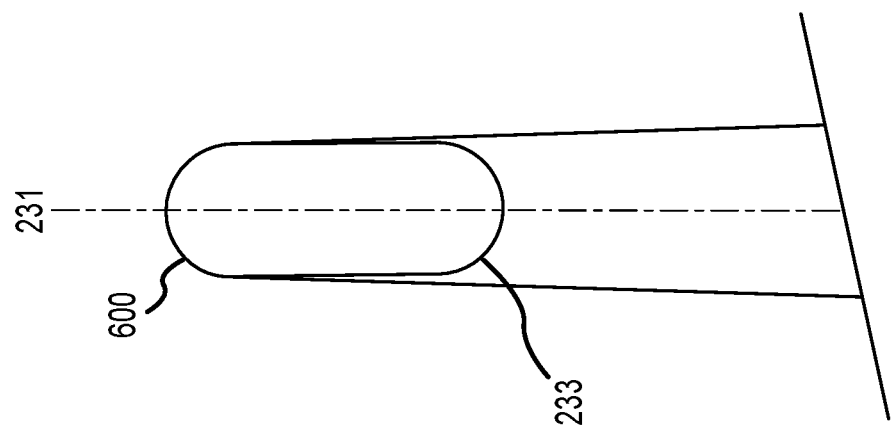
FIG.30B
FIG.30A

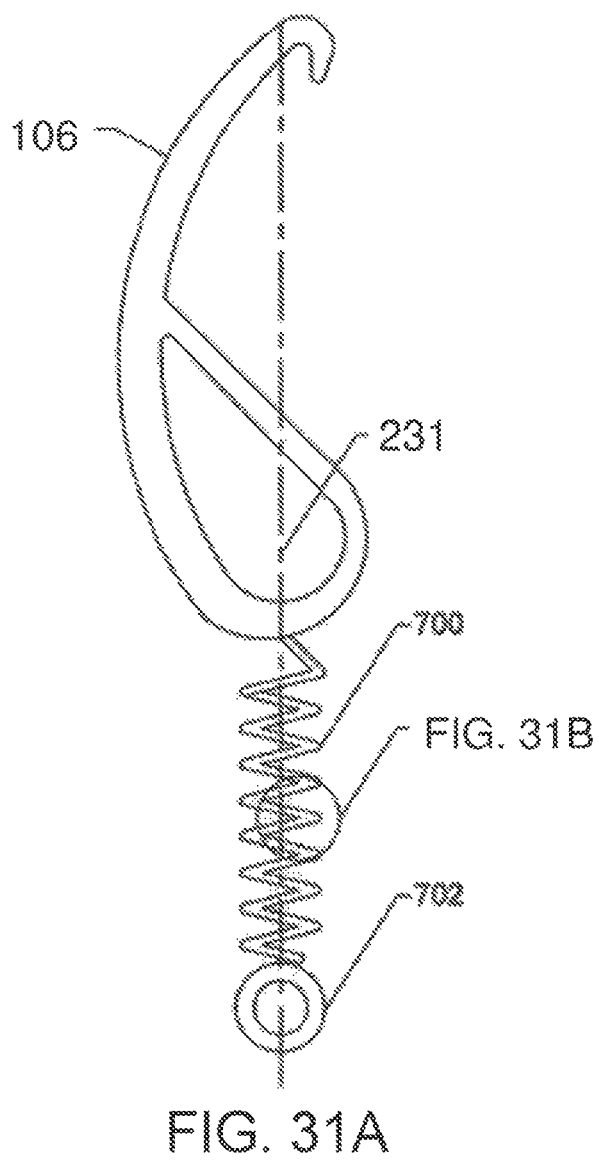
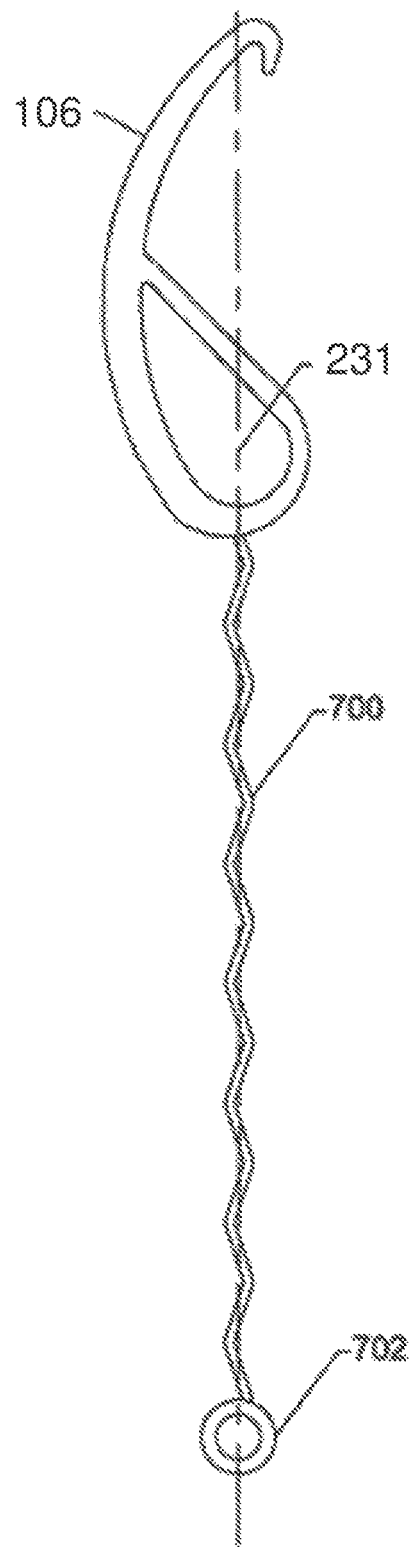
FIG. 31A
FIG. 31B
FIG. 31C

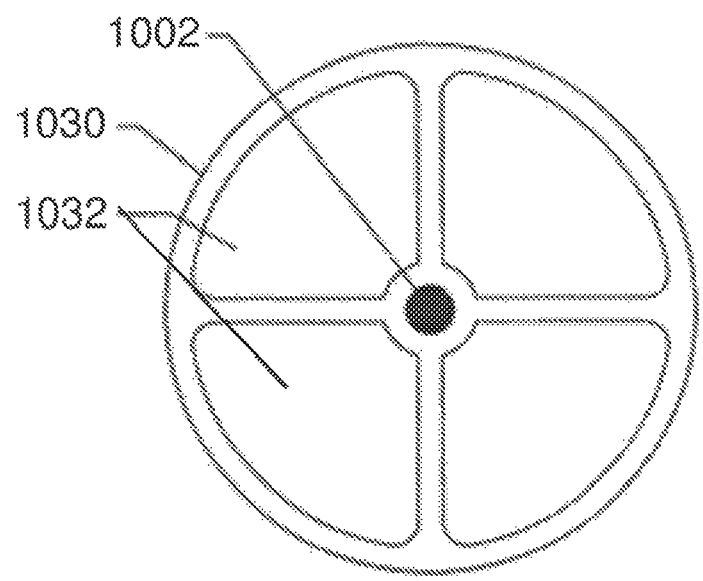
FIG. 38
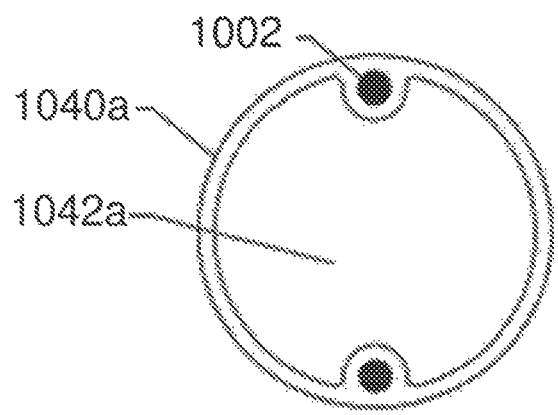 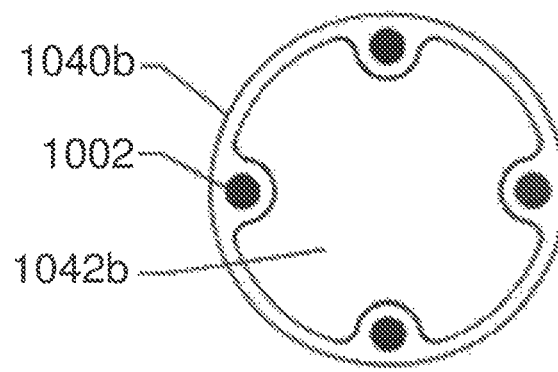
FIG. 39A  FIG. 39B

SYSTEM AND METHOD OF ORAL TREATMENT AND RELIEVING STRESS

CROSS REFERENCE TO RELATED APPLICATIONS

This U.S. Non-Provisional Patent Application is a Continuation-in-Part of and claims the benefit of priority of U.S. patent application Ser. No. 15/945,495 filed Apr. 4, 2018, and entitled "Dental Device and Suction Device," which is a Continuation of U.S. patent application Ser. No. 15/084,230, filed on Mar. 29, 2016, which claims priority to U.S. Provisional Patent Application Ser. Nos. 62/178,129, filed on Mar. 30, 2015, and 62/274,625, filed on Jan. 4, 2016, and which is a Continuation-in-Part of U.S. patent application Ser. No. No. 14/504,518, filed on Oct. 2, 2014 and which issued as U.S. Pat. No. 9,545,195 on Jan. 17, 2017, and which claims priority to U.S. Provisional Patent Application Ser. Nos. 61/961,106, filed on Oct. 2, 2013, 61/967,319, filed on Mar. 13, 2014, and 61/997,780, filed on Jun. 9, 2014, the entire disclosures of which are incorporated herein by reference. This application also claims the benefit of U.S. Provisional Application Ser. No. 62/966,475, filed on Jan. 27, 2020, the entire disclosure of which is incorporated herein by reference.

FIELD

The present invention generally relates to relaxation devices, methods, maneuvers, and systems. More specifically, it relates to a device that stretches muscles of the jaw utilizing a physiologic maneuver to activate the parasympathetic nervous system to promote relaxation and health. The device may be used or optimized for relaxation and dental procedures.

BACKGROUND

Stress has been defined as "a state of mental or emotional strain or tension resulting from adverse or very demanding circumstances" and is usually considered the result of an individual's response to the adverse or demanding circumstances. Simply, the adverse circumstance is the stressor and one's response is the stress. While some stress is good for us ("eustress") as it is the stimulus to perform optimally, the eustress frequently morphs into bad stress ("distress") when our responses to the increasing load of stressors exceeds a certain level. That level is different in different individuals and may be modified within each individual with certain maneuvers which will be discussed herein. The term "stress" as used herein refers to distress.

The World Health Organization has deemed stress as the number one health epidemic of the 21st Century. Stress is pervasive and ubiquitous, and it affects us all. In fact, stress (referred to herein as just 'stress') is estimated to cost the United States economy between $200-$300 billion per year. These economic costs due to stress are further appreciated by the following facts: for every 10 employees on any given day, estimates are that one is absent and three are present but less productive because of stress (40% of the workforce); 75-90% of physician visits are stress related; 60-80% of workplace accidents are related to stress; 60% of employees report diminished productivity from stress; and healthcare costs are 46% higher than less stressed employees. The personal cost of stress may even be more important as stress leads to unhealthy behavior according to the American Psychological Association as amongst highly stressed people: 30% are less likely to eat healthy; 25% are less likely to exercise; 200% less likely to succeed in a weight loss program; get half as much sleep as low-stressed individuals; are at risk of a multitude of chronic diseases as stress has been implicated in immune system disorders including auto-immune diseases and reduced ability to fight off and recover from illnesses, cardiovascular diseases, stroke, Alzheimer's disease, some cancers, depression, and Anxiety Disorders. Most body systems are affected by stress including: mood issues including anger, irritability, and depression, lack of energy and concentration, insomnia, headaches, high blood pressure, increased heart rate, higher cholesterol levels, increase heart attack risk; loss of libido and increased menstrual irregularities and pain; aches and pains in joints and muscles. Stress tends to affect women more than men. Stress severely affects college students with 86% feeling overwhelmed with more than 20% experiencing suicidal ideation and 1.4% attempting suicide. The causes of stress and distress are numerous, and it has been demonstrated that the presence of one stressor will accentuate the stress caused by a separate event or situation. There is in essence a stress multiplier effect.

Humans are wired for protection. This wiring is one major reason our species has survived, and eventually has thrived, over the centuries prior to and since the Cognitive Revolution of 70,000 years ago. To keep us from danger, threats are detected immediately by the amygdala, an almond like structure in our prehistoric or "lizard' brain. The amygdala almost instantaneously begins a cascade of neurotransmitters and substances (epinephrine, norepinephrine, cortisol, ACTH, et al) from the sympathetic portion of the autonomic nervous system that result in the "fight or flight" response very quickly being activated. This was hugely important when humans were threatened by predators or other humans. Our prefrontal cortex, which appeared on the scene approximately 70,000 years ago and gives Homo Sapiens the ability to reflect and reason, can override the fight or flight response generated by the amygdala, but it is much slower acting. There would be no reason to reflect and consider the pros and cons of a threat or a situation if one did not survive, hence this arrangement has worked well in the past when threats to survival were real. We no longer face threats and physical danger to our survival in the first world and the majority of the world. However, the multitude of first world problems from any one or all of the demanding circumstances we are exposed to on a daily if not hourly basis still create a stress reaction within us. This stress reaction inhibits one's ability to create a proper assessment, reflection, and strategy formulation for dealing with the stress from the prefrontal cortex. According to the doctrine of "emotional incompatibility," it is impossible to be creative and reactive at the same time. We simply are prevented from creating a solution to the challenge when we are reactive. Again, not bad in the old days for survival, but problematic in 2020 (and likely even more problematic going forward).

It was also hugely important for our ancestors to recover from these periods of stress. The autonomic nervous system has two divisions: 1), the sympathetic division which generally prepares the body for stressful or emergency situations, i.e., "fight or flight," and 2) the parasympathetic division which controls body processes during ordinary situations and is responsible for recovery, rest, and relaxation. These two systems should be fairly balanced, but the overwhelming input from present society creates a reactive overload imbalance where one is continually under sympathetic stimulation with precious little time to rest and activate the parasympathetic nervous system so recovery can take place. The instant device, system, maneuver, and method will be directed to enhancing parasympathetic nervous system activation so that there is more of a sympathetic/parasympathetic balance. This parasympathetic activation provided by the instant device, system, maneuver, and method will promote better short and long term well-being, serve to prevent chronic diseases, and generally provide an opportunity to enjoy life rather than being continually stressed about it. And it will allow us to be creative so we can create solutions to our challenges rather than just react to them without an optimal solution.

Chronic stress also diminishes one's cognitive ability (i.e., to learn) even when an immediate threat is not present. Acute and chronic stress also inhibits one's ability to make the most optimal decisions (partly because inability to learn, but partly because of fatigue, lack of clarity, diminished motivation, and inability to concentrate amongst others). Hence, stress is an immense villain to students. Stress may be an even more egregious villain in the workplace when one begins to learn experientially but is prevented from optimal learning as one's cognitive ability is diminished and one's ability to make optimized decisions is also limited by stress. Basically, the employee cannot learn the task or job adequately nor respond with the best solution or work product if stressed. Stress is essentially a threat to our society and should be considered not only as a harmful villain, but also as an insidious but threatening enemy as stress creates an invisible ceiling of sorts on one's potential. Chronic stress releases neurotransmitters and peptides in the brain that causes us to feel less energetic, less motivated, more nervous, and less optimistic than we need to be and want to be. Stress is one of the major factors that prevents us from achieving the peak of Maslow's famous triangle, a target and human need that we are all programmed to at least attempt to reach. On the other side of the equation, certain positive activities as well as the act of creating other positive activities causes the release of "good" neurotransmitters that cause us to feel pleasant, good, enthusiastic, and confident in our abilities to overcome challenges that may arise.

Activities such as, exercise, gratitude, movement, being outdoors, adequate sleep, empathy, love, relaxing in a comfortable environment, a positive attitude, and believing in something generate a cascade of those calming inducing neurotransmitters. It is simply our body's way of telling us what is good for us and what is bad for us. We need to listen and do those healthy things that cause us to feel good.

Most people do not listen to their body's messages or do not have the tools to deal with these even if they do recognize them. They are hung up in the lower strata of the triangle still seeking psychological safety and security and preventing the upward transformation that is programmed within all of us. Simply, the stress conundrum causes people to feel poorly about themselves, their place in the world, who they are, why they are here and prevents the full enjoyment of the short time they/we have on this earth. They all want to feel better. Many have headaches, jaw pain, neck stiffness as a result of the tension caused by stress. Pain seems to attract attention. And rightly so. But the headaches are only the tip of the iceberg as there are many deleterious effects of stress affecting all of the multitude of body systems as previously discussed. Also, the iceberg example can be utilized to explain that there is no one cause for pain, headaches and the stressed out feeling that is so pervasive. There are multiple causes that contribute to the headaches, pain, and tension which are perceived by stressed individuals and all of these stressors contribute to and magnify the total stress load.

The physical pain that stress causes is of more concern to most than the psychological pain, but the low level of psychological pain is still perceived as a worrisome pest rather than a harmful villain. It is impossible to be stressed and relaxed at the same time. This is an example of a well-accepted psychological principle termed "emotional incompatibility" that was popularized in the 1960's. It also is impossible to be happy and sad, reactive and creative, or optimistic and pessimistic simultaneously. Since stress and relaxation are incompatible, one way to diminish stress is to encourage relaxation. This has been addressed over the eons of time with unhealthy habits involving alcohol, substances (legal and illegal), drugs (prescription and illicit), and the like.

Humans have also employed meditation, exercise, prayer, solitude, long walks, spa treatments, and other healthy means of relaxation. The easy route seems to be the unhealthy habits all of which have destructive components. Hence, there is a need for a relaxation tool, system, maneuver, and method that promotes relaxation while promoting better health and well-being, and for that tool and method to be augmented by other tools and methods that will create a resilience to stressors that inevitably appear daily and a resilience to those long term stressors which hang around for months if not years. It would be short sighted to attempt to relieve the stress without any effort to control it long term. It would be short sighted to offer an incomplete product (device) to the huge markets that need the whole product (products and systems). One device of the present invention has been previously described in issued U.S. Pat. No. 9,545,195, entitled, "Patient Controlled Dental Device and Method" which is incorporated herein by reference. The device was intended for use in the dental office by providing a jaw retraction means to obviate the aching discomfort experienced by 60% of the dental population from the unnatural act of holding the mouth open for a protracted period of time. It was discovered that the device relieved headaches which was believed at the time to be a result of the simple stretching of the jaw muscles with the device.

It is an object of the present disclosure to provide improved devices and methods for maintaining a mouth in an open position for prolonged periods of time for dental procedures. Ideally, these devices and methods provide improvements over the prior art devices and methods and reduce or eliminate at least some of the discomfort and pain of maintaining an open jaw. Such devices and methods do not overly obstruct a dentist's access to the mouth for performing procedures. The embodiments described herein provide such methods, systems and devices.

SUMMARY

Applicant has determined by that headache and pain relief is not only due to the simple act of stretching muscles, but it is also due to relaxing the subject via parasympathetic activation pathways. This discovery has the potential to bolster the physiological reasons and explanation for relieving headaches, but also to assist stressed individuals in achieving parasympathetic activation so they are allowed to rest and recover from the sympathetic fight or flight producing stressors that they may encounter dozens of times during a normal day. These discoveries are as follows: relaxing combats stress. Stress can be relieved, controlled, and prevented by relaxation. The use of a jaw stretching device to stretch the jaw muscles does indeed relax people and relieves stress.

Use of a jaw stretching device according to embodiments of the present disclosure induces relaxation by three independent but complimentary actions:
1) Stretching of the jaw muscles relaxes them just as any other muscle in the body. Also, stretching and relaxation of one muscle group will relax other muscle groups in the body, which will diminish the overall muscular tension throughout the body. Stretching the jaw muscles relaxes them and relieves the built-up tension in the jaw muscles from repeated clinching throughout the day when stressed or multi-tasking. Relief of tension in the jaw muscles prevents the spread to other muscle groups in the head and neck area which may result in headaches, neck pain, or facial pain. Stretching of the jaw routinely has been shown to prevent these tensions. Stretching of the jaw with embodiments of the present disclosure relieves the painful symptom complex, at least partially, with a single use.
2) Stretching of the jaw releases positive neurotransmitters that tell the body it is in recovery mode rather than fight or flight/chronic stress mode, and it is time to relax. Similar to a yawn, this action provokes a "relaxation reflex" of sorts. Testing performed on multiple subjects by the inventor has shown that use of the jaw stretching device improves heart rate variability in these subjects. Heart rate variability is generally accepted as reflecting parasympathetic activity and is a measure of parasympathetic function. Hence, use of the jaw stretching device does create parasympathetic activation.
3) The one or so minute it takes to perform a stretching session is an important diversion or break from the daily stressful routines and a respite from the multiple stressors that burden the individual. If structured breathing, positive messaging, positive visualizations, and/or soothing music is added to the stretching routine, it will be even more effective at relaxing the individual. Hence, in addition to stretching, adding other maneuvers proven in the past to also cause parasympathetic activation will enhance the overall effectiveness. Combining the three elements of a simple jaw stretching routine works in concert to relax a stressed individual. Each element will enhance the actions of the other individual elements. The devices, systems, maneuvers, and methods of the present disclosure are simple, time-efficient, and are provided so that they are affordable by everyone.

Moreover, humans have exaggerated connections to the brain from the hands and facial area. Employing these two areas during the relaxation session is more meaningful and impactful than attempting to relax with just meditation or measured breathing (for example). Both the hands and the facial area of the body are more richly innervated than most any other body parts and these areas occupy a much larger sensory area in the brain that is disproportionate to their actual body surface area. This arrangement is evolutionary in nature and reinforces the importance of these two areas in our lives.

The tactile experience of holding an object in ones' hand and performing an act with that device directed at the facial region (teeth) is sensed and appreciated by the brain and directs the brain's attention away from the stressors at hand. This action will make meditation, measured breathing and other relaxation maneuvers more effective. Employing a tactile experience with the hands and teeth to relax an individual is a goal of this disclosure. Employing the tactile experience involving the hands and teeth with one or more of the following activities during or associated with the tactile experience will further relax individuals and is a goal of this disclosure: stretching of the jaw, guided meditation, music, reading of educational and inspirational materials, reminders, tracking means, and the like.

The homunculus concept is demonstrated in the FIG. 1. The sensory homunculus represents a map of brain areas dedicated to sensory processing for different anatomical divisions of the body. The primary sensory cortex is located in the postcentral gyms, and handles signals coming from the thalamus. These signals are transmitted on from the gyri to the brain stem and spinal cord via corresponding nerves. Along the length of the primary motor and sensory cortices, the areas specializing in different parts of the body are arranged in an orderly manner, although ordered differently than one might expect. The toes are represented at the top of the cerebral hemisphere (or more accurately, "the upper end", since the cortex curls inwards and down at the top), and then as one moves down the hemisphere, progressively higher parts of the body are represented, assuming a body that's faceless and has arms raised. Going further down the cortex, the different areas of the face are represented, in approximately top-to-bottom order, rather than bottom-to-top as before. The homunculus is split in half, with motor and sensory representations for the left side of the body on the right side of the brain, and vice versa. The amount of cortex devoted to any given body region is not proportional to that body region's surface area or volume, but rather to how richly innervated that region is. Areas of the body with more complex and/or more numerous sensory or motor connections are represented as larger in the homunculus, while those with less complex and/or less numerous connections are represented as smaller. The resulting image is that of a distorted human body, with disproportionately huge hands, lips, and face.

Humans are programmed to be rewarded for utilizing these richly innervated regions of the body as the hands and the facial area are more important for survival than other less innervated areas. Neurotransmitters are released upon engaging and using these areas which cause humans to feel better than not using these areas. In essence, our bodies encourage the use of these richly innervated areas. The hands are humans most utilized tool for handling any object, feeding ourselves, caring for others, and for survival. Many societies employ the hands in relaxation activities such as rosary beads, worry beads, coin shuffling, prayer, and the like. We simply feel better when using our hands, hence providing a tactile device to be utilized during a period of relaxation will enhance the relaxation effort. The facial area is responsible for nutrition, breathing, seeing, hearing, and amorous touch amongst other functions. (Kissing is very parasympathetic activating.) Engaging the facial area in a relaxation effort will also provide additional positive input that is lacking in activities such as meditation that do not provide tactile stimulation of this area. The combination of combining the hands and facial area together during a relaxation session will further enhance that session and the relaxation effort and is an object of this invention.

The relaxation of the individual is responsible for the relief and relative prevention of tension type headaches, migraine headaches, orofacial pain, neck stiffness, and psychological tension. This relief is not just due to the simple stretching of muscles as originally thought.

The method of utilizing a jaw stretching device to relax an individual is an object of this invention. There remains a need to protect the subject long term and beyond the immediate relief that a jaw stretching device provides. That is an object of the current device, system, maneuver, and method.

Systems and methods of the present disclosure are constructed and provided to bolster the body's healthy responses to stress and make individuals better prepared to deal with the inevitable stressors that arise. Poor daily habits create stressors to the body that provide a foundation for the experienced stressful state of the individual, and changing or minimizing these poor daily habits need to be incorporated into any relaxation/stress management program in order to effect a lasting change and to make the individual more resilient to daily stressors. There are four major categories of activities which have a major impact on how we feel every day, and how daily stressors may affect us. These four activity classes may be grouped into general categories which have been arbitrarily termed the "Four Pillars of Well-Being" and are: Attitude; Sleep; Movement; and Nutrition.; It is imperative to combine the short-term relaxation effects of the use of a calming and relaxing jaw stretching device with a program to improve poor habits that actually contribute to stress and may prevent the individual from diminishing the effects of stress in the long term. Changing habits may be difficult for most, hence it also is imperative to provide the individual with proven methods and techniques to effect habit change. The instant system and method may provide these. Science has shown that the three elements that drive habit formation are: 1) Instant gratification, 2) Social awareness of what others are doing, and 3) Progress monitoring. The use of the instant Stress Management System of the current invention will incorporate all of these. The jaw stretching device does provide more or less instant relief. The System may also provide a means of connecting with others and their successes and a means for monitoring one's progress in the system in addition to the lifestyle changes needed to reduce the stressors which contribute to the underlying stress load we all carry.

The physiologic maneuver comprises placing the tooth engaging tip of the device of the current invention on the top of the lower incisor teeth and exerting downward traction by engaging a portion of the hand in the handle of the device, the handle being placed directly beneath the chin, hence the downward traction is aligned more or less with the vertical axis of the teeth. The downward traction is maintained for a period of time ranging from 10 seconds to several minutes, but optimally for a minute.

During this period of time, additional components may be utilized which may include one or more of the following adjunctive actions: measured breathing, yawning, mental focus on one's breath, meditative techniques and the like. The maneuver distracts and disengages the user from the user's current issues, problems, and concerns while stretching the jaw muscles and relaxing the individual by neurochemical means stimulated by the adjunctive actions. The maneuver may include only the stretching of the jaw muscles or may include any or all of the adjunctive actions and/or the momentary disengagement measures.

Related to the stressors and relaxation benefits discussed above, dental procedures can benefit from the relaxed and stretched jaw muscles.

Dental procedures are very common and are necessary for proper dental health, whether it be dental fillings, dental crown applications, root canals, orthodontic work, periodontal surgery, dental cleaning, and many other procedures. One common problem with these dental procedures is that the patient must maintain an open mouth for extended periods of time. The dentist, dental assistant, or dental hygienist must have adequate exposure to access the site to be treated. While opening of the mouth for short periods of time is not problematic for most patients, many, if not most, patients do have difficulty maintaining an open mouth for the extended periods of time required for many dental procedures. All dental patients have at least some difficulty opening their mouths for prolonged periods, as this prolonged opening fatigues the muscles and becomes uncomfortable. Most patients just accept that going to the dentist is uncomfortable and just tolerate the discomfort. Fifty percent of patients have significant difficulty keeping the mouth open for any procedure. This percentage increases with the length of time of the procedure. Elderly, young, and patients on psychotropic drugs have more difficulty that others, but virtually all patients have discomfort opening the mouth for any period of time.

This rather high figure may reflect the prevalence of temporomandibular joint disorders (TMD) in the general population. Epidemiological studies have revealed an average of 30%-44% prevalence of TMD in the general population. All of these patients will experience difficulty at the dentist, with either limited mouth opening or with pain and discomfort in the jaw muscles from straining to keep the mouth open or both. There is also a subset of the population that does not have TMD but that does have difficulty and/or pain with limited mouth opening, due to other causes of muscle tightness. Examples of such causes of difficulty with mouth opening include bruxism, clenching, stress, psychological issues, and others. This segment accounts for as much as 20% of the population. Hence, well over 50% of the population may have difficulty with prolonged mouth opening for dental procedures.

The typical reason for difficulty with prolonged mouth opening is muscle fatigue and spasm that initially becomes uncomfortable but progresses to become quite painful. The human mouth is a simple hinge, with the mandible articulated with the skull at the temporomandibular joint. The muscle systems that cause the mandible to close are mainly the large masseter muscles and the temporalis muscles. These are robust and responsible for forceful chewing, mastication, clenching, bruxing, etc. The corresponding muscles responsible for opening the mouth are mainly the small and delicate pterygoid muscles. This causes a disparity in the opposing muscle groups, which is not of importance in the normal function of the mouth during usual activities such as eating, drinking, speaking, and the like. However, prolonged opening of the mouth is affected by, and very difficult because of, the size, disparity, and arrangement of the opposing muscle sets. The smaller pterygoid muscles tire after several minutes of prolonged opening, causing discomfort and actual pain.

This creates a dilemma, as the dental practitioner must have access to the oral cavity to perform the necessary task, but frequently the simple act of holding the mouth open is uncomfortable to the patient. Devices that assist in holding the mouth open have been in use for many years for this reason. These consist of bite blocks, which are simple wedge devices placed between the teeth to prop open the mouth by creating a consistent space between the upper teeth and lower teeth by depressing the mandible. Bite blocks are used on one side of the jaw or the other to allow access for procedures, and this asymmetrical use can strain the temporomandibular joints, often triggering joint pain. Use of a bite block also creates a persistent and continuous stretching of all the muscles that affect the depression of the mandible, i.e., the pterygoids, or elevation of the mandible, i.e., the masseters and the temporalis groups. These devices offer no period of relaxation for the muscles to recover from the stress of the continuous stretching. This lack of a relaxation period can result in pain and discomfort to the patient. The bite blocks also occupy space within the oral cavity and impede access or exposure to the specific area that needs attention or treatment.

Other known devices have been developed that prop the mouth open but are almost universally awkward to employ, as they also frequently inhibit access to all parts of the oral cavity and the dental practitioner must navigate around these devices to perform the necessary and intended maneuvers. They also provide a continuous and persistent stretching of the musculature, which results in discomfort while attempting to assist in keeping the mouth open. The bite blocks commonly used actually stimulate contraction of the muscles responsible for closing the mouth and accentuate the problems and difficulties.

In U.S. Pat. No. 6,030,217, Fletcher describes a device comprised of a flexible mouthpiece that fits over the lower front teeth and an elongated flexible member attached at one end to the mouth piece and the other end to a handhold object. Fletcher's device may suffer from limitations that preclude optimal functioning to assist with opening the mouth and maintaining it open in a comfortable position in a safe manner. For instance, the mouthpiece has sufficient flexibility to permit the mouthpiece to bend and release from the lower teeth when the flexible member is subjected to a selected threshold tension. This, in essence, means that the mouthpiece will typically flex and become disengaged from the lower teeth if the patient exerts more downward force than the mouthpiece will tolerate. With significant downward force being exerted and an abrupt release by the mouthpiece, the mouthpiece may be forcefully propelled or pulled downward toward the hand. As soon as the trailing edge clears the teeth, it may engage the lower lip with significant abrupt downward force, and at the very least, bruise the lower lip if not lacerate it. As well, the mouthpiece may be propelled as a missile toward the hand, where it may impact the hand, fingers, or other body part or even the dentist or dental assistant. Just the thought of a piece of plastic flying about the dental operatory, contaminating equipment and personnel with saliva, enough to discourage the use of such a device.

Additionally, since any incremental tension may be at least partially, if not mostly, absorbed by the flexible mouth piece of Fletcher, rather than transferred to the mandible, the mouth piece will bend or deform, instead of providing additional consistent, graded and gradual downward pressure on the mandible. Slow and gradual increases in tension downward are often needed for maximum relaxation and stretching. Hence, the flexible mouthpiece of Fletcher may be limited for this reason as well.

Moreover, the elongated flexible member of Fletcher can create an unlimited number of angles and directions in which the downward force may be directed. The elongated flexible member of Fletcher may introduce variability in the use of the device, which also can be a safety issue. The teeth may be accustomed to downward pressure and are very stable when pressure is in the same plane as the long axis of the tooth. If the force is downward and forward, or downward and to one side or the other, the tooth or teeth may be loosened or tilted. Marginally loose teeth from periodontal disease or other causes could be loosened even more than at their resting state. The temporomandibular joint (TMJ) may also be damaged by inappropriately directed forces. Tension forward or outward may even dislocate the TMJ, and tension to the side may cause TMJ dysfunction or worsen TMJ preexisting conditions. With so many variations in the direction of the force, it may be exceedingly difficult to align the flexible member, the mouth piece and the handhold object so that the proper direction of the force is maintained during the entire dental procedure, which may last for an hour or longer. Hence, the flexible member of Fletcher may be convenient to connect the mouth piece with the handhold object, but it may be dangerous to the patient and the staff for a number of reasons, and it may create unintended problems and difficulties.

Additionally, there may be a need for devices or methods that increase the degree of opening of the mouth beyond passive opening using the muscles of the jaw or opening with a simple assist device. Not only do patients experience discomfort from having the jaw open for protracted periods, but the limited exposure to the dental operative field constantly constrains the dental practitioner. The ability to open the mouth maximally diminishes with the time the mouth is open, as the muscles fatigue and less than a fully open position is sought for comfort reasons. The practitioner is forced to operate and perform procedures within the mouth, which is basically a small hole, and that hole becomes smaller with time. The wider the patient is able open the teeth, the better the exposure for the dental practitioner and the less tedious the work becomes.

No known prior art devices are targeted improving the degree of opening the mouth or providing more exposure as the procedure progresses. Bite blocks act as props, and the Fletcher device may either prop or distract the mouth open, but this is where these devices stop. The bite blocks are forced between the upper and lower molars and may actually trigger a reflex to bite down. They certainly do not continue to improve the degree of opening. The Fletcher device may assist in opening the mouth and may reduce the discomfort despite the significant limitations and safety issues it presents, but it does not continue to improve the opening of the mouth and continue to improve the exposure available to the dentist. While the prior art includes devices that attempt to address the mouth-opening problem, all of these devices have shortcomings, as discussed herein.

Another major limitation of known prior art devices is that they are all placed into the mouth, in addition to other devices used in a procedure. In other words, they are additive devices and occupy valuable space in the mouth, which limits the access by the dentist or hygienist in addition to the other tools that may be used. For example, while many different tools and devices may be used during a dental procedure, suction is used almost universally in dental procedures. Hence, the known prior art devices must be inserted in addition to the suction apparatus. This may become awkward and confusing, for example, if the patient is responsible for the suction with one hand and the Fletcher prior art device with the other hand. More importantly, the space occupied by a combination of suction tube and the prior art devices may well impede access to the mouth by the dentist. There is the probability of simply having too many items in the mouth at one time to allow easy access.

The device herein disclosed and described provides a solution to the shortcomings in the prior art through the disclosure of a device, method, maneuver, and system of relieving stress. In order to achieve this outcome, a main object is to enhance the parasympathetic nervous system (PNS) activation. The PNS is activated by stretching the collective muscles of mastication. This stretching relaxes these muscles as stretching any other muscle group in the body relaxes that muscle group. It also indirectly relaxes other muscle groups in the head and neck region via a complex interaction with regional nociceptors (sensory neurons) and other feedback loops, albeit to a slightly lesser extent than the stretched muscles.

Another object of the invention is to simulate a yawn thereby once again activating the parasympathetic nervous system and promoting healing. The device is inserted onto the tops of the lower front teeth and a user pulls down carefully on the handle and thereby opening the mouth wide and stretching said muscles. Imitating yawning also triggers subconscious signals that remind a user of sleep and can induce a meditative state that enhances the relaxation process.

Furthermore, the act of yawning has been demonstrated to cause the release of a combination of neurotransmitters which produce a sense of well-being, promote increased (improved) heart rate variability (HRV), promote parasympathetic nervous system activation, and provide a calming effect psychologically. The "cocktail" of neurotransmitters released when one yawns include oxytocin (the "love" or "bliss" hormone), GABA, serotonin, dopamine, and others. It is the combination of these ingredients that produces the effect rather than just the effect of one neurotransmitter or a dominant neurotransmitter apparently. It is an object of this invention to simulate a yawn and thereby create the release of these calming neurotransmitters to calm the subject, promote a sense of well-being, promote parasympathetic activation, promote improved HRV, and to relax the subject.

Heart rate variability (HRV) is widely recognized as an indicator of parasympathetic nervous system activation. The time between each heartbeat varies more when one is relaxed than when one is stressed, essentially. HRV is a measurement of this variability.

Regarding improved HRV and parasympathetic activation, testing of multiple subjects were conducted to determine the effect on HRV and other surrogates of parasympathetic activation (readiness, sleep quality, return to calm, etc.) by stretching the jaw muscles as described above. Testing was performed with the following commercially available equipment:
   a. Polar H10 chest strap heart rate sensor and Elite HRV software
   b. CorSense fingertip sensor and Elite HRV software
   c. Oura ring and software
   d. Muse 2 brain sensing headband and software
   e. HearMath Inner Balance Bluetooth Sensor and software The relaxation stretching device was utilized for approximately one minute and testing done immediately before and after usage. Subsequently, after using the device three times per day for three days, the subjects were tested again. HRV and other surrogates for parasympathetic activation were improved after a single use and after three days of use of the device. This testing documents HRV improvement which indicates or proves that the use of the device causes parasympathetic activation. It is an object of this invention to promote increased HRV and parasympathetic function by utilizing a relaxation jaw stretching device as described and thereby relaxing the subject, hence diminishing the psychological stress since it is impossible to be stressed and relaxed and the same time.

In addition, the subject may be relaxed enough during the jaw stretching activity that a yawn may spontaneously occur which further serves to release the cocktail of calming neurotransmitters. Alternatively, the subject may visualize a yawn during the stretch to purposefully cause a yawn to occur. It is much easier to accomplish a yawn if at least partially relaxed with the mouth in a yawn position. An object of this invention is to either encourage a yawn to occur either spontaneously or with forethought so these calming neurotransmitters are released.

Another object of the invention is to provide a means to allow users to receive relaxation guidance while using the device. The mobile device software application is available on a wide range of mobile devices and lets users perform relaxation exercises anywhere. The software app includes messages and soothing sounds while the user operates the device and may comprise at least one or more of the following phases: Phase I makes suggestions to pursue personal change; Phase II makes suggestions of becoming emotionally stronger; Phase III strategies for stress management and coping; Phase IV fostering creativity and Phase V support for routine practice and a lifelong commitment to health and relaxation.

A further object of the invention is to aid in dental procedures by easing the ability of the patient to maintain an open mouth for an extended period of time, to open the mouth beyond that which is achievable from natural active opening, and to do both comfortably, the devices and methods described herein may rely on several basic physiologic principles. By exploiting these principles, a dental procedure can be more comfortable for the patient and can be performed by the practitioner more quickly and without significant interruptions. The degree that the mouth can open comfortably will also be enhanced, providing better access to the mouth for the dental practitioner.

One of the physiologic principles of which the present devices and methods may take advantage is that the distraction of the mandible may be intermittent, rather than the consistent and persistent distraction necessary with the prior art devices. This intermittent distraction may allow the musculature to rest occasionally and temporarily recover from the stress of the stretching. A brief change in the degree of stretching is often all that is frequently needed to prevent the discomfort.

Another physiologic principle is that downward pressure on the mandible actually relaxes the large masseter, temporalis, and internal pterygoid muscles that close the mouth via a reflex. This is the same reflex that relaxes these muscles when chewing exerts downward pressure on the mandible and stops the chewing motion when the teeth touch.

Hence, distraction of the mandible downward will not only aid the opening muscles of mastication (suprahyoid and lateral pterygoid muscles), but can obviate much of the contraction of the much larger and more powerful closing muscles of mastication by stretching and relaxing them.

Another principle is that continued low level, graded, and incremental traction on a muscle will relax and stretch the muscle, thus elongating the muscle and inhibiting reflex contraction of the muscle. Continued low level traction or stretching will continue to elongate the muscle. Hence, a technique and device that employs at least some of these physiologic principles may cause the mouth to open wider than possible with just active opening (without an assist) by the patient.

Another principle is that the maximum distraction of the mandible will occur when the patient temporarily relaxes the distractive force when the dental practitioner is not directly engaged in intra oral manipulations or functions. This may happen intermittently, when the practitioner must change implements or instruments, drill bits, scalers, curettes, probes, etc. During this brief interlude, the patient can temporarily relax the distraction to provide relief to the stretched muscles. Subsequent stretching will be even more effective as a result of this intermittent relaxation, which cannot occur with the use of a bite block. It may also be problematic to allow relaxation using the Fletcher device, because the mouth piece may become dislodged if all of the tension on the flexible member is relaxed, as there would be no force to hold the mouth piece adjacent to the teeth. The inability to accommodate these important maneuvers often prevent the prior art devices from functioning optimally.

Moreover, embodiments of the present disclosure may allow the dental practitioner to encourage or prompt the patient to provide more distraction at certain times. Hence, while the patient may control the force and degree of depression of the mandible, the dental practitioner has input, so adequate exposure is provided. This feedback loop may be essential in providing adequate exposure to the practitioner while providing patient comfort. The feedback loop may be another physiological principle not shown to be exploited in the prior art devices.

The feedback loop may also go from patient to practitioner. The patient frequently is unable to articulate any meaningful message to the practitioner if prior art devices are used, essentially using grunts and garbled words. The devices of the present disclosure would allow verbal and other communication, as will be described further below.

Aspects of the present disclosure provide a device for helping maintain a mouth of a patient in an open position during a dental procedure. The device may include a tooth engaging portion comprising at least one groove for accepting at least one lower tooth of the patient's lower jaw, an extension portion that extends away from the tooth engaging portion, and handle that extends down from the extension portion and ends in a caudal end. The caudal end of the handle and the groove of the tooth engaging portion may lie along a longitudinal axis drawn through a center of the groove. The handle and the extension portion may comprise a solid, one-piece construct. At least part of the tooth engaging portion may comprise the solid, one-piece construct. The tooth engaging portion may comprise a distal end of the solid, one-piece construct, and a piece of material attached to the distal end of the one-piece construct, wherein the piece of material is softer than the one-piece construct.

The extension portion may be curved. The extension portion and the tooth engaging portion may be forked, and a space between two prongs of the tooth engaging portion and the extension portion may be configured to accept a suction tube. The caudal end of the handle may comprise a finger loop through which a finger of the patient may be extended to facilitate application of downward force. A traction member may further be included to be removably coupled with the handle, for applying downward force to the handle. For example, the traction member may be a weight. The device may also additionally include a suction member coupled with the tooth engaging portion and/or the extension portion. Another feature may be a tissue displacement member coupled with the tooth engaging portion and/or the extension portion, for displacing the cheek and/or tongue of the patient. Yet another feature may be a tensiometer coupled with the device to measure downward force applied to the device.

Aspects of the present disclosure may also provide a method of maintaining a mouth of a patient in an open position during a dental procedure. These methods may involve placing a groove of a tooth engaging portion of a mouth distraction device over at least one lower tooth in a lower jaw of the patient's mouth, and pulling down on a handle of the mouth distraction device in a direction along a longitudinal axis of the lower tooth to maintain the lower jaw in an open position relative to an upper jaw of the patient's mouth. The groove of the tooth engaging portion of the mouth distraction device and the handle of the tooth distraction device may lie along a common, distraction device longitudinal axis, and the distraction device longitudinal axis may lie along the longitudinal axis of the at least one tooth during the pulling step.

The pulling step and/or the placing step may be performed by the patient. After the pulling step, the pulling force from the handle may be released to allow the lower jaw to relax and the mouth to at least partially close, and the pulling step may be repeated to reopen the mouth. The groove may be placed over multiple lower front teeth.

The methods may also involve applying suction in the patient's mouth, using a suction device incorporated into or attached to the mouth distraction device. Also, a weight may be attached to the handle of the mouth distraction device to apply downward force. The cheek and/or tongue of the patient may also be displaced using a tissue displacement member incorporated into or attached to the mouth displacement device. A lip retractor means may be attached to or incorporated into the mouth distraction device to displace the lips laterally, vertically, or other directions to provide more exposure to the oral cavity. A tensiometer coupled with the device may be used to measure downward force applied to the device. After the pulling step, a suction device may be passed through an opening in the mouth distraction device and into the patient's mouth, and suction may be applied in the mouth with the suction device, while the distraction device maintains the mouth in an open position.

The mouth opening devices described herein may be constructed for children in more or less the same configurations as described herein, but smaller to accommodate the smaller mouth and teeth of children. Moreover, attachments may be provided to the device to create a more visually appealing device to children.

These and other embodiments and aspects are described in greater detail below, in relation to the attached drawing figures.

It is briefly noted that upon a reading this disclosure, those skilled in the art will recognize various means for carrying out these intended features of the invention. As such it is to be understood that other methods, maneuvers, applications and systems adapted to the task may be configured to carry out these features and are therefore considered to be within the scope and intent of the present invention, and are anticipated. With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods, maneuvers, and systems for carrying out the several purposes of the present disclosed device. It is important, therefore, that the claims be regarded as including such equivalent construction and methodology insofar as they do not depart from the spirit and scope of the present invention. As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. The objects features, and advantages of the present invention, as well as the advantages thereof over existing prior art, which will become apparent from the description to follow, are accomplished by the improvements described in this specification and hereinafter described in the following detailed description which fully discloses the invention, but should not be considered as placing limitations thereon.

The Summary is neither intended nor should it be construed as being representative of the full extent and scope of the present disclosure. The present disclosure is set forth in various levels of detail in the Summary as well as in the attached drawings and the Detailed Description and no limitation as to the scope of the present disclosure is intended by either the inclusion or non-inclusion of elements, components, etc. in this Summary. Additional aspects of the present disclosure will become more clear from the Detailed Description, particularly when taken together with the drawings.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

The term "a" or "an" entity, as used herein, refers to one or more of that entity. As such, the terms "a" (or "an"), "one or more" and "at least one" can be used interchangeably herein.

Unless otherwise indicated, all numbers expressing quantities, dimensions, conditions, ratios, ranges, and so forth used in the specification and claims are to be understood as being modified in all instances by the term "about" or "approximately". Accordingly, unless otherwise indicated, all numbers expressing quantities, dimensions, conditions, ratios, ranges, and so forth used in the specification and claims may be increased or decreased by approximately 5% to achieve satisfactory results. Additionally, where the meaning of the terms "about" or "approximately" as used herein would not otherwise be apparent to one of ordinary skill in the art, the terms "about" and "approximately" should be interpreted as meaning within plus or minus 5% of the stated value.

All ranges described herein may be reduced to any sub-range or portion of the range, or to any value within the range without deviating from the invention. For example, the range "5 to 55" includes, but is not limited to, the sub-ranges "5 to 20" as well as "17 to 54."

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the Summary, Brief Description of the Drawings, Detailed Description, Abstract, and Claims themselves.

BRIEF DESCRIPTION OF THE DRAWINGS

The accompanying drawings, which are incorporated in and constitute a part of the specification, illustrate embodiments of the disclosed system and together with the general description of the disclosure given above and the detailed description of the drawings given below, serve to explain the principles of the disclosed system(s) and device(s).

FIGS. 9A, 9B, 9C, 9D, and 9E are side, front, close-up/perspective, end-on/cross-sectional, and posterior perspective views, respectively, of a mouth opening device with a built-in suction channel for connecting directly with a suction hose, according to many embodiments.

FIGS. 20A, 20B, and 20C show sectional views of various ways to anchor a tubular braid with a suction tube apparatus for use with a mouth opening device, according to many embodiments.

FIGS. 26A, 26B, and 26C show side views of the handles of various mouth opening device, according to many embodiments.

FIGS. 30A and 30B show end views of a tooth hook of a mouth opening device that can swing, according to many embodiments.

FIGS. 31A, 31B, and 31C show side perspective views of a mouth opening device with a secondary tether that can be pulled downward, according to many embodiments.

FIG. 38 is a transverse cross-section view of an exemplary embodiment of a multi-lumen suction tube.

FIG. 39A is a transverse cross-section view of another exemplary embodiment of a suction tube.

FIG. 39B is a transverse cross-section view of another exemplary embodiment of a suction tube.

FIG. 47 B demonstrates the path of the subject using the device, method, maneuver, and system of the current invention in controlling migraine headaches, but may be utilized for control of stress, headaches, TMJ issues, and other stress related ailments.

The drawings are not necessarily to scale. In certain instances, details that are not necessary for an understanding of the disclosure or that render other details difficult to perceive may have been omitted. It should be understood, of course, that the disclosure is not necessarily limited to the embodiments illustrated herein. As will be appreciated, other embodiments are possible using, alone or in combination, one or more of the features set forth above or described below. For example, it is contemplated that various features and devices shown and/or described with respect to one embodiment may be combined with or substituted for features or devices of other embodiments regardless of whether or not such a combination or substitution is specifically shown or described herein.

DETAILED DESCRIPTION

Figure 1A:
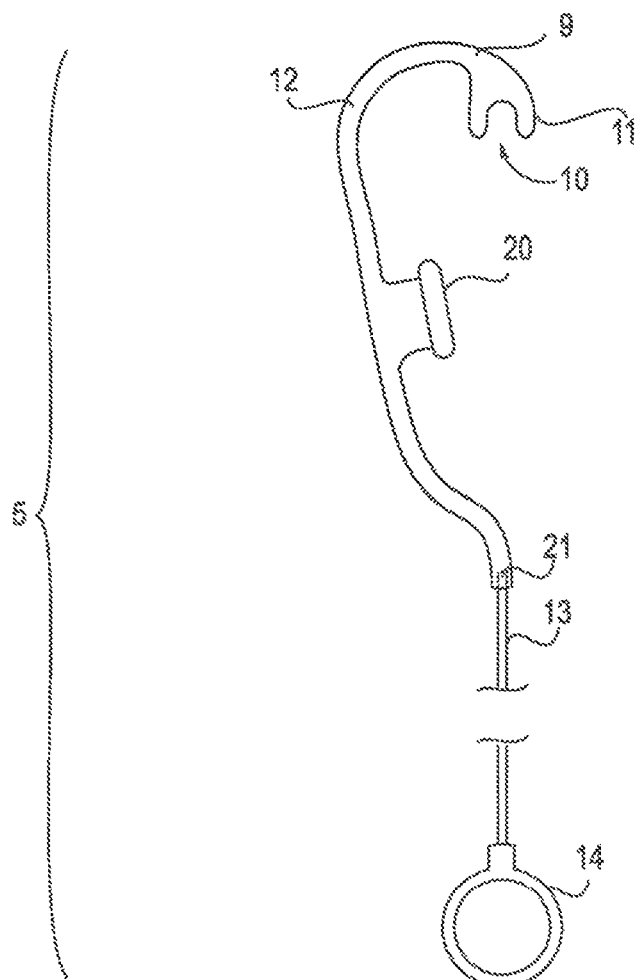
FIGS. 1A and 1B are side and top views, respectively, of a mouth opening device, according to many embodiments.

FIGS. 1A-1D illustrate a mouth opening device 5, from various perspectives (side view, top view, side view in a cross-sectional view of a mouth, and perspective view in a mouth, respectively). As illustrated in FIG. 1A, the device 5 may include a tooth piece (or "tooth component") 9, which may fit over at least one lower tooth, an extension component 12, which may extend out of the mouth and over the lower lip, extending caudally to a point under the chin and in more or less the same coronal plane as the two lower front teeth, and a flexible component (or "flexible member") 13, which may extend from at attachment point 21 at the bottom (or "caudal") end of the extension component 12 further caudally to allow a patient to provide traction on the device 5. The flexible component 13 may be attached at its caudal end to a handle or ring 14, which the patient may grip during use. The tooth piece 9 may fit over one or more lower teeth and includes a channel 10 with lips 11 on each side of the channel 10. The extension component 12 may include a chin pad 20 and may have a wide variety of lengths, shapes and sizes. For example, the extension component may have an overall length of between about 2 inches and about 24 inches.

Figure 1B:
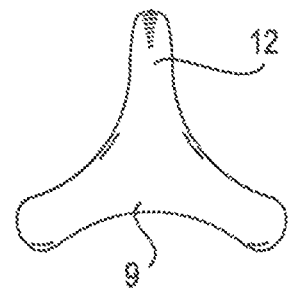

FIG. 1B is a top view of the device 5 and demonstrates the tooth component 9, which fits over the teeth, and the upper part of the extension element 12.

Figure 1C:
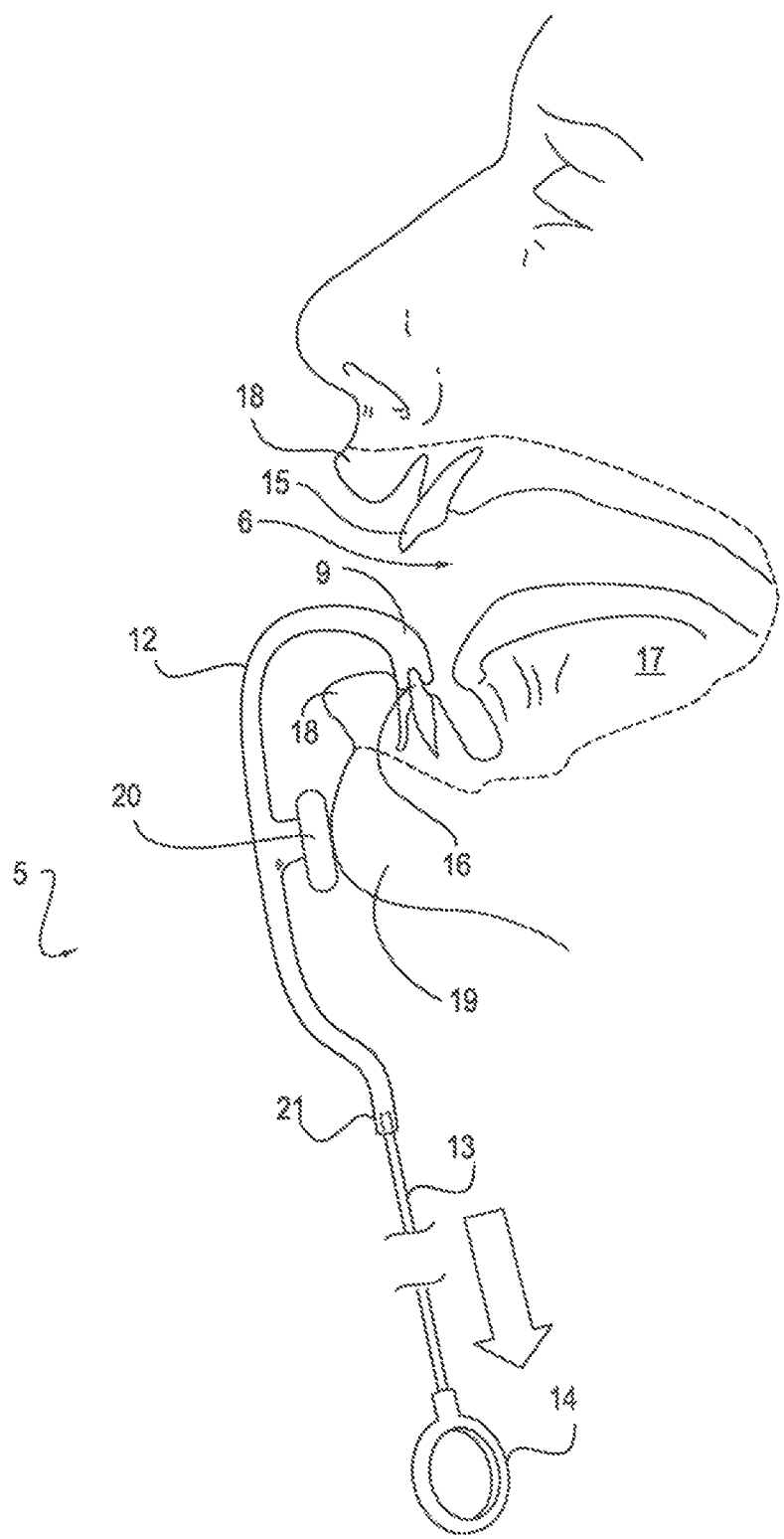
FIGS. 1C and 1D are side/cross-sectional and perspective views, respectfully, of a mouth, illustrating operation of the mouth opening device of FIGS. 1A and 1B, according to many embodiments.
Figure 1D:
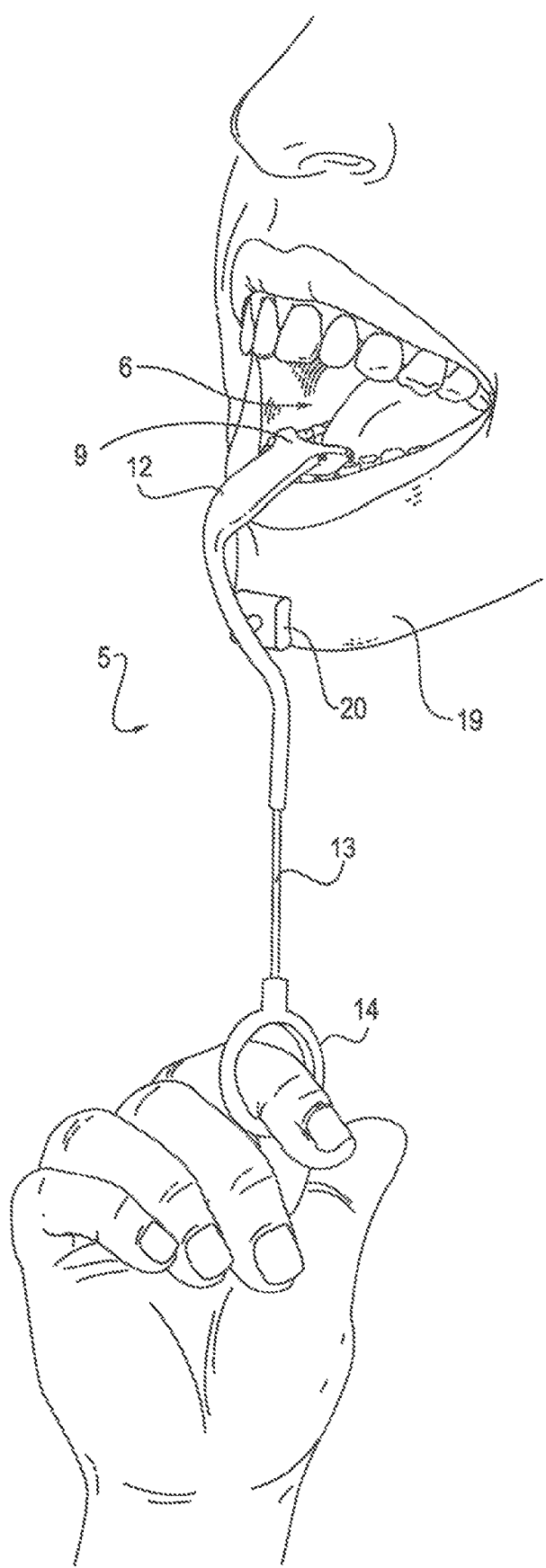

FIG. 1C is a midline cross-sectional view of a mouth 6, showing an upper tooth 15, a lower tooth 16, the tongue 17, the lips 18 and the chin 19. FIG. 1C illustrates how the tooth component 9 may rest over the lower tooth 16, with the chin pad 20 resting against the chin 19. Pulling the handle/ring 14 downward may cause the mouth to open and the chin 19 to lower relative to the skull and upper mouth. FIG. 1D is a perspective view of the mouth 6 and device 5 from FIGS. IA-IC.

As illustrated in FIGS. 1C and 1D, the device 5 may be used for deflection of the jaw or chin 19. The chin pad 20 may be included or not included. Pulling downward on the jaw can stimulate a reflex that relaxes the closing muscles of the jaw, so the action of the device can not only aid the opening muscles but can also relax the opposing closing muscles. By combining the assistance to the small opening muscles with traction and relaxing the large opposing closing muscles at the same time, the patient may be able to comfortably maintain an open mouth for a protracted period of time.

It may be important that the direction of the traction be in the longitudinal axis of the teeth, as they may be subjected to this same force daily during chewing and other activities. They may be accustomed to this direction of force. Traction anteriorly or obliquely forward may cause a tilt of the tooth and may loosen them. Any force directed other than along the long axis of the engaged teeth may be expected to displace the teeth and loosen them, especially if that force was exerted for 30 minutes or longer. The devices described herein may be designed so that the direction of force is along the vertical axis of the teeth, hence avoiding this potential problem. Additionally, traction outward or from posterior to anterior may create forces detrimental to the temporomandibular joint (TMJ). The device 5 may be designed so that the direction of force is along the vertical axis of the teeth, hence avoiding this potential problem. This direction of force is best illustrated in FIG. 1C and in FIG. 2 described below.

Figure 2:
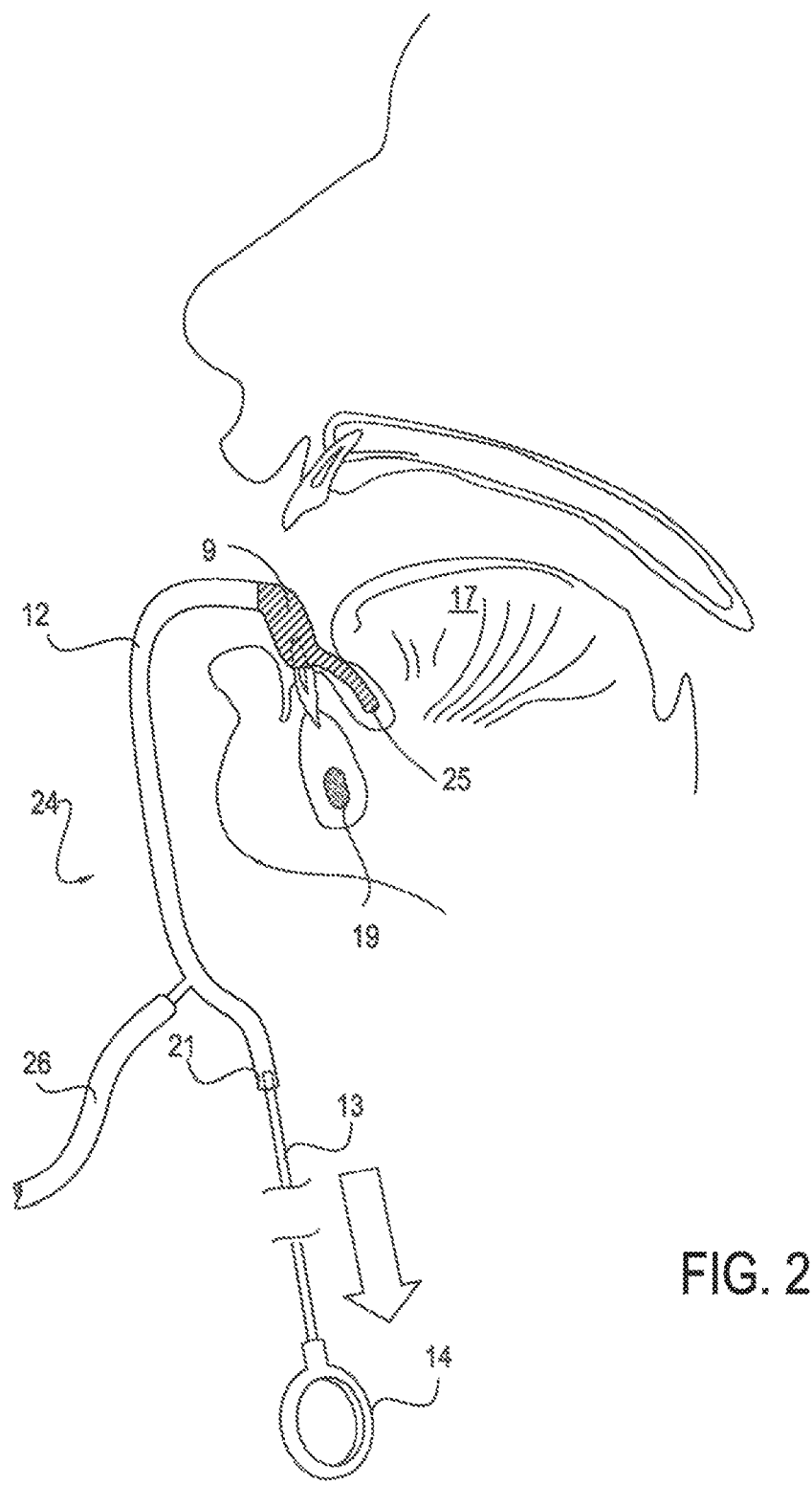
FIG. 2 is a sagittal view of a mouth and a side view of a mouth opening device in position in the mouth, according to many embodiments.

Referring now to FIG. 2, a sagittal view of the mouth is shown, along with a mouth opening device 24. The attaching component 9, extension element 12, flexible component 13 and ring 14 of the mouth opening device 24 may be the same or similar to the corresponding components of the mouth opening device 5 and other mouth opening devices described herein. A difference may be that the extension element 12 of the mouth opening device 24 does not include a chin pad. The device 24 may also include a suction channel within the extension element 13 and attaching component 9. A suction extension 25 may extend from the attaching component 9 to a point under the tongue 17 where most of the saliva exits the salivary ducts. There may also be a suction tubing 26, attached to the extension member 12 on one end and available suction machine on the other end. This combination of comfortable distraction of the jaw 19 and suction of saliva can be appealing for several reasons, one of which is that it may obviate the need for recurrent interruptions of the procedure to aspirate saliva from the mouth. It may even obviate the need for a dental assistant.

With reference now to FIGS. 3A-3D, a mouth opening device 28 is shown, which may not include the flexible member of the mouth opening devices 5 and 24 described herein. Otherwise, the components of the mouth opening device 28 may be the same or similar in many respects to that of the other mouth opening devices described herein and vice versa. The device 28 may include a tooth piece component 30, which may fit over at least one lower tooth, an inflexible extension component 32 (or "handle"), which may extend out of the mouth and over the lower lip extending caudally to a point under the chin to a point approximately in the same coronal plane as the two lower front teeth, and a gripping member 33 (or "finger loop") for gripping and applying downward traction by the patient. The gripping member 33 may be a finger hole, but any other types, sizes and configurations of gripping portions may also be used. The tooth piece 30 may be made of a softer durometer material, formed into small posts 31, which may form the small groove 34 to accommodate the teeth and provide stability. The posts 31 may be arranged so that the teeth may fit between them, either side to side or front to back, so that the device 28 may be used either in the midline of the patient, i.e., directly over then under the chin, or from the side of the mouth, i.e., ninety degrees from the midline position. This latter position may place the curve of the handle 32 out of the way of the dental practitioner. Moreover, the posts 31 may be supplanted or augmented by deeper grooves (not shown) to receive the teeth. These grooves may be oriented transversely within the tooth piece 30 so that the device 28 may be positioned directly in the midline and in an anterior posterior or sagittal direction within the tooth piece 30, so that the device 28 may be positioned over the front teeth ninety degrees from midline. The device 28 may comprise either of the transverse or sagittal grooves or both and may be used from directly in the midline to the side of the mouth.

The handle 32 is contemplated in at least some embodiments as being solid and inflexible. The handle 32 can add stability to the device 28 and may help ensure that the direction of the force applied by the patient is in the long axis of the tooth. The finger loop 33 of the handle 32 may be directly beneath the tooth, whether the handle 32 and device 28 are positioned in the midline or ninety degrees from midline, so the direction of force applied by the patient is generally with the long axis of the tooth. Any traction not in the long axis of the tooth may tilt and loosen the teeth and potentially damage the TMJ, especially when traction is applied for 30-60 minutes, the usual length of most dental procedures.

Moreover, the inflexible handle 32 may allow the patient to adjust the tooth piece 30 from the finger hold 33, which may be difficult or impossible with embodiments that include a flexible member. The patient may also be able to control the tooth piece 30 when closing the mouth at certain intervals to rest and to maintain its position with the teeth. Maintaining the position on the teeth would be extremely difficult with a flexible connection between the hand hold means and the tooth piece, especially without any accessory attachment means to the teeth similar to the grooves or posts previously discussed.

Figure 3A:
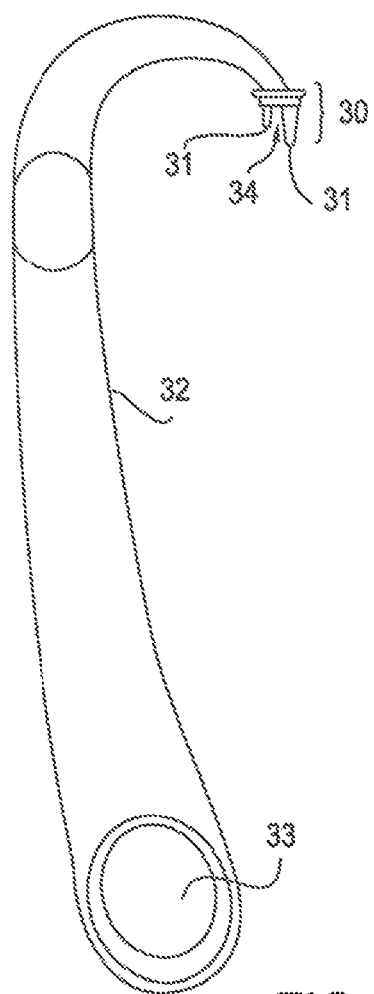
FIGS. 3A, 3B, and 3C are side, front and bottom views, respectively, of a mouth opening device, according to many embodiments.

As best illustrated in FIG. 3A, the tooth piece component 30, which fits over the lower teeth, may include a channel 34 with posts 31 on either side. The inflexible extension component 32 may extend out of the mouth and over the lip (not shown) then downward to a point below the chin (not shown.) The lower or caudal portion of this extension component 32 may include (or alternatively may be attached to) the gripping member 33, which may be a handle, a handheld ring, or the like. The tooth piece or mouthpiece 30 may be fairly rigid, so as not to slip off the perch on the lower teeth. This rigidity may be important in maintaining the relationship between the mouthpiece 30 and the teeth and in the ability to provide gradual and graded traction on the device 28, without it slipping off the teeth because of flexibility in the tooth piece. Flexibility may preclude the type of graded and gradual gentle pressure needed to accomplish maximum and comfortable mouth opening. The posts 31, or some other similarly functioning element to secure the tooth piece 30 to the teeth, may also provide the necessary stability for the device to function properly. For example, there may be times during a dental procedure when the dentist is not actively engaged in the mouth and changing tools or components that the patient may close or partially close the mouth. During this action of closing the mouth, the tooth piece 30 may become dislodged or mispositioned, if there were no means on the tooth piece 30 to secure it, especially if there was a flexible connection. The flexible connection would preclude control of the tooth piece 30 by the patient and the ability of the patient to adjust the position of the tooth piece 30 at all.

In addition, the device may have a tensiometer interposed between the extension component 32 and the gripping member 33, so that when downward traction is provided by the patient, the tensiometer displays the force. This display may encourage the patient to provide more or less traction by emitting different audible sounds if the tension provided by the patient was more or less than desired. This tensiometer-based alarm may be an important safety feature, which may optimize the opening of the mouth while preventing damage to the temporomandibular joint and other tissues. The tensiometer may be releasably attached to the gripping member 33 or some other point on the handle mechanism, and another traction point or finger hole may be provided from which to provide traction. As well, the tensiometer may be provided separately for employment with any of the mouth opening devices described herein. It may be attached to the component, which extends out of the mouth, a handle, or the gripping member 33 in one of any number of ways.

Figure 3B:
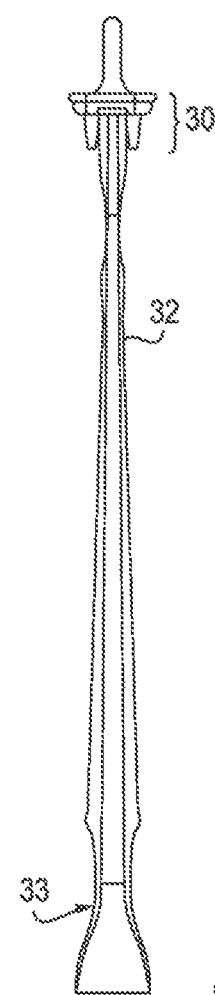

FIG. 3B is a front view of the mouth opening device 28, illustrating its thin profile. The thin design may occupy less space than thicker design while maintaining strength necessary to accomplish the necessary tasks. The tooth piece 30 may contain a swivel mechanism at the connection to the handle so that the tooth piece can be turned in relationship to the handle so that the handle can be positioned at virtually any position from one side of the mouth to the other.

Figure 3C:
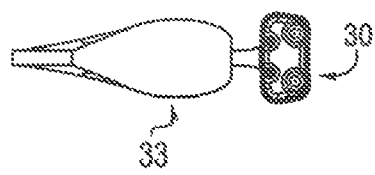

FIG. 3C is a bottom-up view of the device 28, slightly tilted to demonstrate the finger loop 33 is directly beneath the tooth piece 30.

Figure 3D:
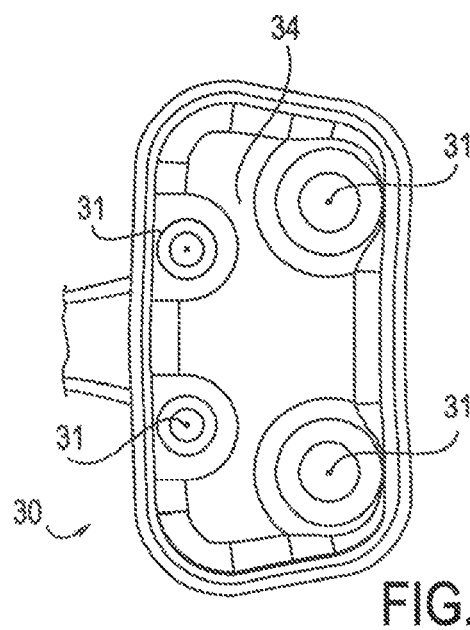
FIG. 3D is a close-up, bottom view of a tooth piece of the device of FIGS. 3A-3C.

FIG. 3D is a bottom view of the tooth piece 30, demonstrating the position of the posts 31. This arrangement may allow the device 28 to be positioned in the midline or ninety degrees from midline while still positioning the finger loop 33 directly under the front teeth and allowing the downward traction to be along the long axis of the teeth.

Figure 4:
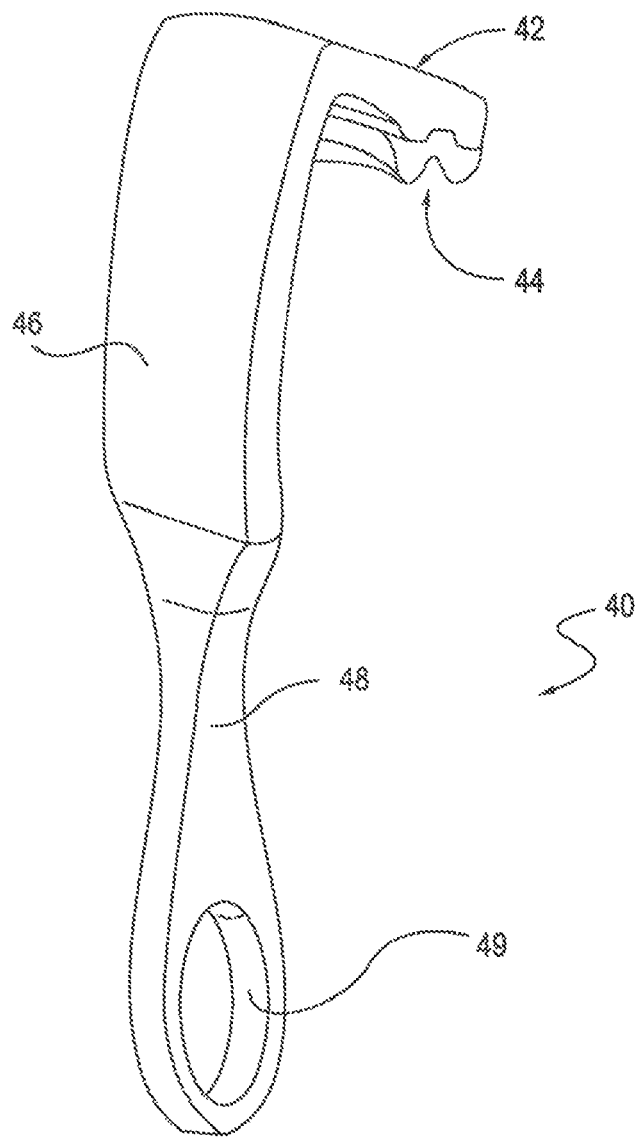
FIG. 4 is a posterior perspective view of a mouth opening device, according to many embodiments.

FIG. 4 is a posterior perspective view of a mouth opening device 40. The components of the mouth opening device 40 may be the same or similar in many respects to that of the other mouth opening devices described herein and vice versa. The device 40 may include a tooth engaging portion 42, which may include a soft, tooth-contacting surface 44, a neck portion 46 and a handle 48, which may include a finger hole 49. The top or apex of the neck portion 46 may not protrude as far cephalically in some of the other mouth opening devices described herein.

Figure 5:
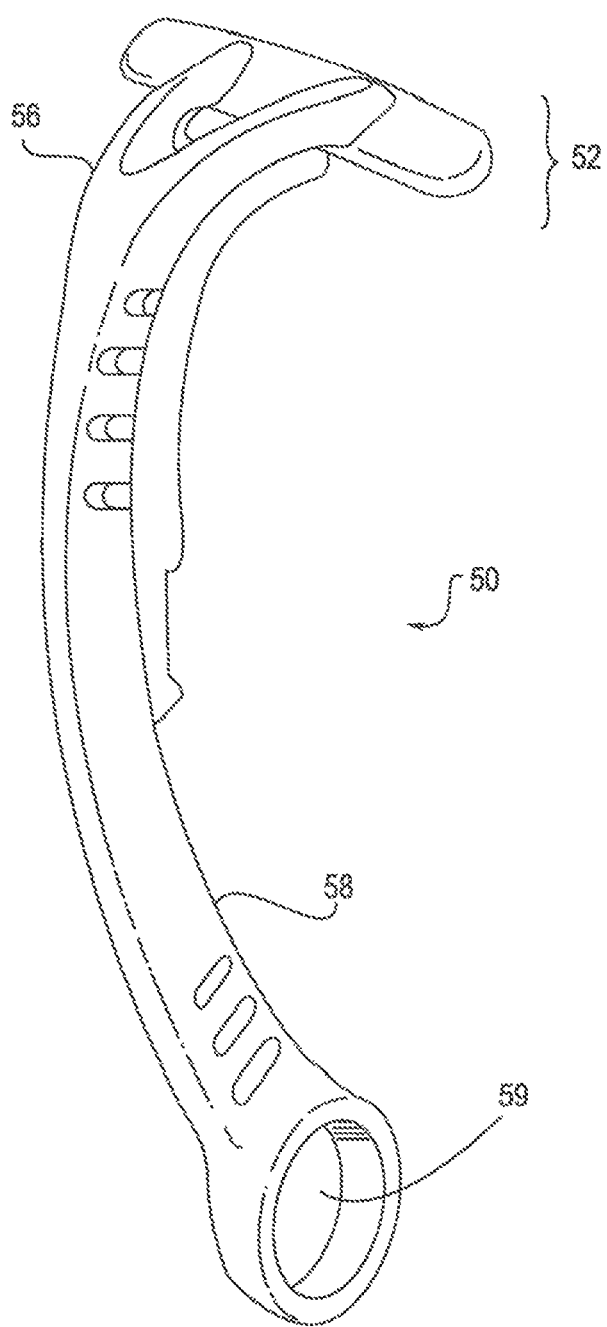
FIG. 5 is a posterior perspective view of a mouth opening device, according to many embodiments.

FIG. 5 is a perspective view of a mouth opening device 50, which may include a tooth engaging portion 52, a neck portion 56, and a handle 58 with a finger hole 59. The components of the mouth opening device 50 may be the same or similar in many respects to the other mouth opening devices described herein and vice versa. The tooth piece 52 may include any of the tooth-engaging components described herein, such as the posts and troughs described herein. As well, because of their low-profile design, the more cephalic aspect of the handle may provide a finger rest for the dentist to assist in stability of the dental devices and hands and fingers within the mouth. The direction of force may be with the long axis of the teeth.

Figure 6A:
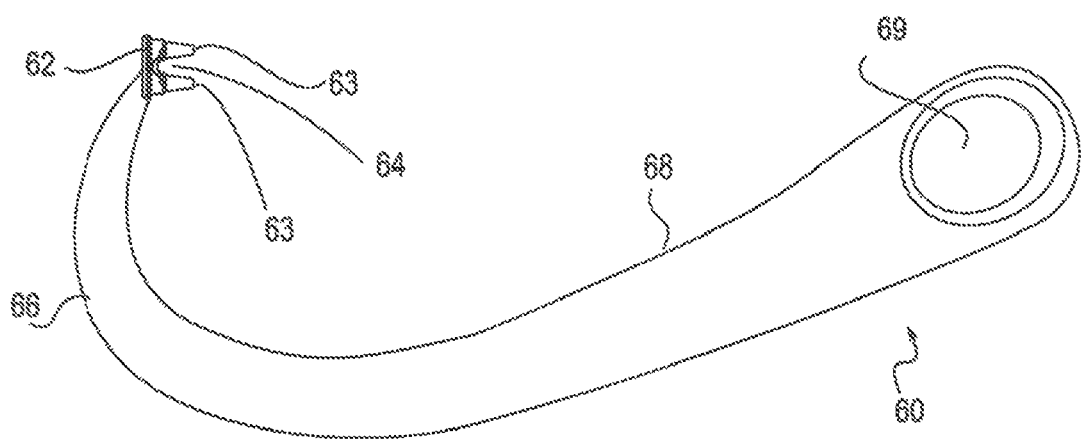
FIGS. 6A, 6B, and 6C are side, close-up/front and close-up/side views, respectively, of a mouth opening device, according to many embodiments.
Figure 6B:
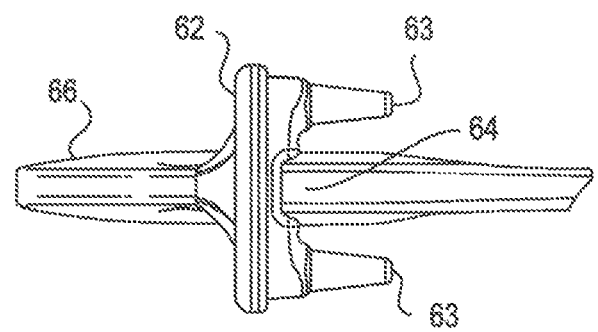
Figure 6C:
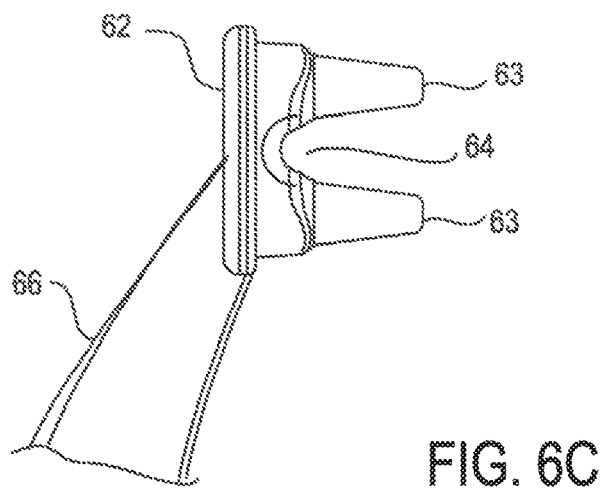

FIGS. 6A-6C are side, close-up front and close-up side views, respectively, of a mouth opening device 60. The components of the mouth opening device 60 may be the same or similar in many respects to that of the other mouth opening devices described herein and vice versa. The device 60 may include a tooth engaging portion 62, a neck portion 66, and a handle 68, which includes a finger hole 69. The tooth engaging portion 62 includes multiple posts 63, which are typically made of a softer material than the rest of the device 60, and which form a bidirectional trough 64 (or "groove"). The apex of the neck portion 66 may be less prominent, projecting not as far cephalically as in the mouth opening device 5 described herein. The curvature of the handle neck portion 66 and handle 68 may be exaggerated compared to that in the mouth opening device 5 described herein, which may provide additional room for the mandibular body and associated soft tissues within the curvature, so the device 60 can be placed ninety degrees from midline while still engaging the middle front teeth. The distance from the front teeth to the side of the jaw may be greater than the distance from the front teeth to the mental protuberance or chin, which may be appropriate for the device 60 if used from the side while the tooth piece is engaged over the lower middle front teeth. This aspect of the construction of the device gives the device 60 may give more utility than device which must be applied and used only from a midline position as it positions the device 60 to one side and out of the dentist's way.

FIGS. 6B and 6C are close-up views of the tooth piece 62, demonstrating the combination of the shallow groove 64 and posts 63 that may accommodate the front teeth from a midline position or ninety degrees from midline. A groove alone may not accommodate all different configurations of lower front teeth and different sized mandibular arches that occur in the general population. The variations in anatomy may demand different sized and shaped grooves if the tooth piece was constructed only with a groove or trough to engage the teeth. The combination of the groove 64 with the posts 63 will provide the stability and secure engagement necessary for the device to provide adequate downward traction without slippage. The tooth piece 62 may also be constructed with a soft durometer material, at least in the trough or groove 64, which may allow the teeth to indent that material when engaging the device, creating traction and more stability than would be present if the material was not soft and compressible. Hence, the tooth piece 62 may comprise at least one or a combination of the following: one or more grooves 64 or troughs to receive the teeth, posts 64 or other means to receive the teeth, and a softer durometer material at the base.

Figures 7A, 7B, 7C:
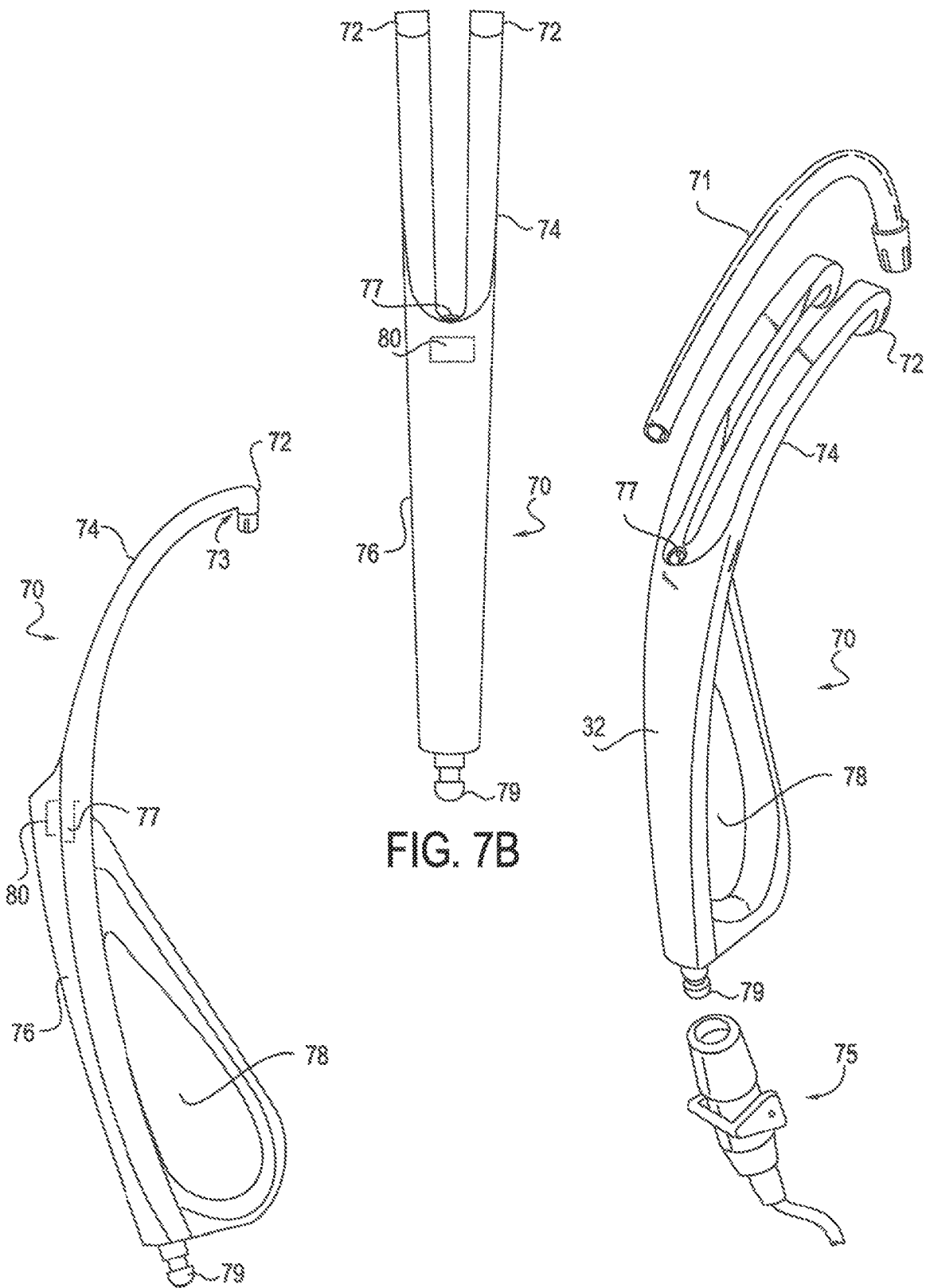
FIGS. 7A, 7B, and 7C are side, front and posterior perspective views, respectively, of a mouth opening device with components for connecting with a suction device, according to many embodiments.

Referring now to FIGS. 7A-7C, a mouth opening device 70 may include suctioning component(s) to provide suction through the device 70. The components of the mouth opening device 70 may be the same or similar in many respects to that of the other mouth opening devices described herein and vice versa. This combination of comfortable distraction of the jaw and suction of saliva may obviate the need for recurrent interruptions of the procedure to aspirate saliva from the mouth. In some procedures, it may even obviate the need for a dental assistant. It generally will make it simpler for the patient to hold onto only one item.

Suction or evacuation may be provided by either attaching a standard or modified suction device to one of the mouth opening devices described herein, or alternatively or in combination, may be provided via a built-in suction channel within a handle of the device. The device 70 may include a tooth engaging portion 72 with an angled section 73, a neck portion 74, a handle 76, which may include a hand hold 78, a suction channel 77 in the handle 76, and a suction connector 79 at the caudal end of the handle 76. As illustrated in FIG. 7C, a piece of suction tubing 71 may be connected to one end of the suction channel 77, and a source of suction force 75 may be attached to the suction connector 79, in order to provide suction within the mouth during a procedure.

FIGS. 7A-7C illustrate a mouth opening device 70 that includes a suction component. The tooth engaging portion 72 (or "tooth piece") may be configured as a rounded hook and includes a sharp corner 73, to engage the lower front teeth, instead of the posts and grooves described earlier. Alternatively, or in combination, the posts and grooves may be employed in the mouth opening device 70. The neck portion 74 extends from the tooth engaging portion 72, and the handle 76 with the hand hold 78 extends from the neck portion 74. As illustrated in FIGS. 7B and 7C, the tooth engaging portion 72 and the neck portion 74 may be forked, so that each portion has two halve or prongs. The suction channel 77 in the handle 76 may extend from a suction tubing recess 80 at one end to the suction connector 79 at the other end.

FIG. 7B is a frontal view of the device 70, which demonstrates the forked neck portion 74 and tooth engaging portion 72. Between them may be a space for the suction tubing. At the junction of the neck portion 74 with the handle 76, the suction tubing recess 80 may be configured to receive a proximal end of a piece of suction tubing 71, preferably with a friction fit. It may comprise an O ring or other means to secure within the cavity or recess 80. Alternatively, or in combination, a ribbed connector may be used instead of the cavity or recess 80.

FIG. 7C is an oblique perspective view of the device 70, which illustrates how a standard suction tube 71 may be inserted into the cavity or recess 80, so that the tip of the suction tube fits over the front teeth adjacent to the tooth pieces 72. With the suction tube 71 in place and the caudal end of the device connected to a suction hose 75, the suction tube 71 is stabilized, while downward traction can be provided by the patient.

Figure 8C:
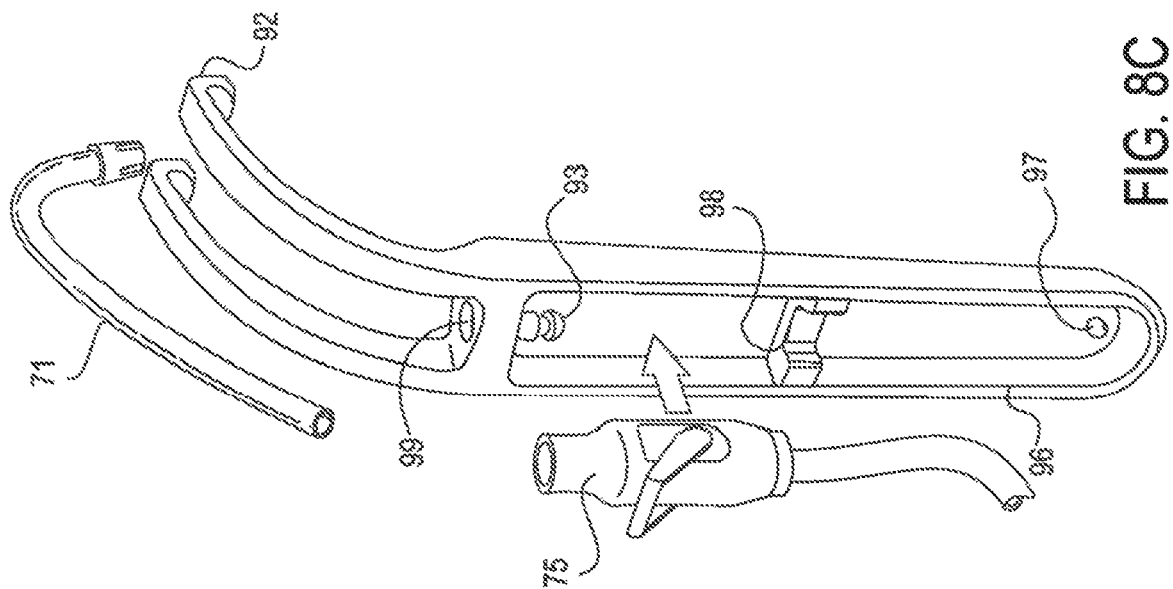
FIGS. 8A, 8B, and 8C are side, front and posterior perspective views, respectively, of a mouth opening device with components for connecting with a suction device, according to many embodiments.
Figure 8B:
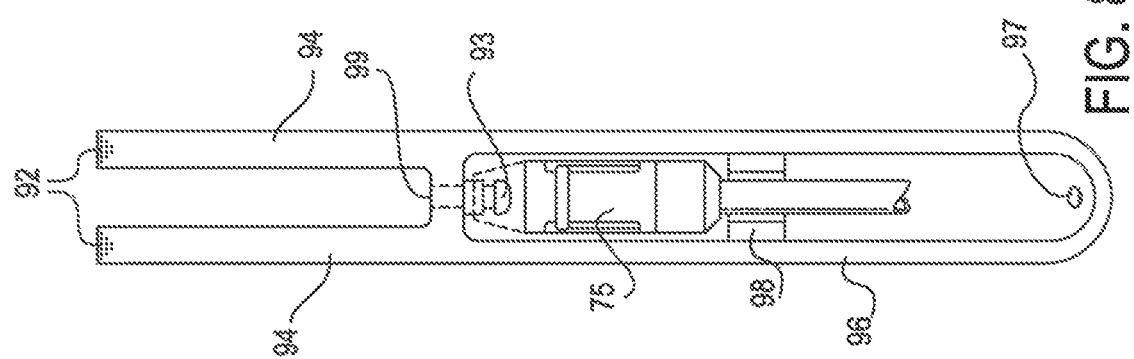
Figure 8A:
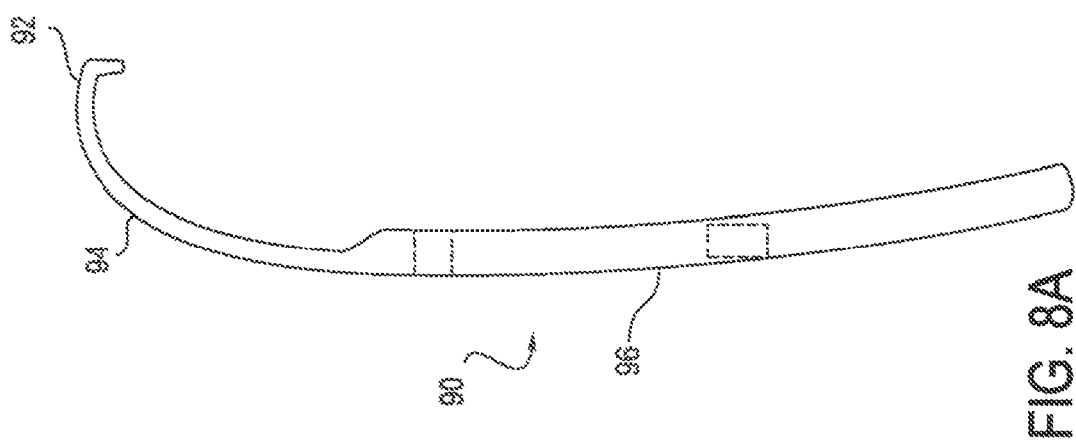

FIGS. 8A-8C are side, front, and rear perspective views, respectively, of a mouth opening device 90. The components of the mouth opening device 90 may be the same or similar in many respects to that of the other mouth opening devices described herein and vice versa. The device 90 may include a tooth engaging portion 92, a neck portion 94 and a handle 96. The tooth engaging portion 92 is forked and has a sharp corner to secure the teeth and a very low profile overall. The neck 94 may also be forked. The device 90 may also include a suction tube recess 99 and a suction valve connector 93, which are configured to attach to suction tubing 71 and a suction hose 75, respectively. The handle 96 may include a tube rest 98 for supporting the suction hose 75 and a finger hold 97 for facilitating holding of the handle 96 by the patient.

FIG. 8C is an oblique perspective view of the device 90, with the suction tube 71 and suction hose 75 detached. Standard suction tubes and standard suction valves that are commercially available may be used with any of these embodiments. Alternatively or in combination, specialized tubes and connectors may be used with any of the mouth opening devices described herein.

Referring now to FIGS. 9A-9E, a mouth opening device 100 may provide suction without the use of an additional suction tubing piece. The components of the mouth opening device 100 may be the same or similar in many respects as the other mouth opening devices described herein and vice versa. The device 100 may include a tooth engaging portion 102, a neck portion 104, and a handle 106, which includes a hand hold 107 and a suction connector. As illustrated in the cross-sectional drawing of FIG. 9D, the handle 106 and the neck portion 104 may both be hollow, thus forming a suction channel 110, which extends from the tooth piece 102 to the suction connector 108. As illustrated in FIG. 9C, suction inlets 112 into the suction channel 110 may be located along one or more sides of the tooth engagement portion 102. The suction inlets 53 may even extend even further toward the gingival margin 114 than is indicated in this illustration, even curving under and abutting the gingival margin 114 in some cases. With this configuration, the device 100 can help evacuate the mouth of saliva, if the patient closes his/her lips about the distal aspect of the device 100.

Referring to the tooth piece 102, it may be desirable that the tooth piece 102 extend as far toward the gingival margin as possible so that suction is optimized, but without contacting or impinging on the gums or gingiva. This could range from 3 to 15 mm, but optimally may be 6-9 mm. Since the suction inlets 112 may not extend to the dependent portion of the mouth where saliva and fluids collect, the mouth may be closed and the lips pursed around the neck portion 104 to evacuate fluid from these dependent portions of the mouth. In this position, with the lips closed around the neck portion 104, air may travel through the nostrils, the nasopharynx, and the oropharynx and out through the suction inlets 112, and, in the process, will evacuate fluid and saliva that may be pooled in the dependent portions of the mouth.

Alternatively or in combination, the inflexible one-piece construction of the handle 106, the neck portion 104 and the tooth piece 102 may allow the device to be tilted upward by elevating the handle 106 so that the tooth piece can be directed into dependent portions of the mouth by the patient or the dental practitioner to directly aspirate and evacuate fluid and saliva. A compact tooth piece 102 may allow the positioning the suction inlets 112 in a variety of areas within the mouth that would not be practical if the tooth piece 112 were larger. Moreover, without the inelastic, inflexible neck portion 104, this maneuver may not be possible. As well, the surface of the neck portion 104 which abuts the upper and lower lips may be smooth for this maneuver to be practical as the device may be more or less inserted into the mouth. Irregularities or sharp corners could irritate or even lacerate the lips during this maneuver.

Alternatively or in combination, a simple attachment mechanism may be provided on the handle proximal to the tooth piece to releasably or fixably attach the suction component and the attachment mechanism may be one or more of metal, rubber, plastic, polymer, fabric, fiber or adhesive or the like. Moreover, the intraoral suction component the mouth opening devices may be positioned so that there is tubing or other similarly function element to provide suction that may be placed over the front teeth or, alternatively or in combination, along the labial or front side of the teeth and circle dorsally around the molars so that the tip of the suction component is positioned on the lingual or back side of the lower front teeth. This portion of either suction component may also comprise a component which serves to displace at the cheek and/or the tongue away from the area in which the dentist intends to work. In other words, a displacement component may be combined with the suction component and may be placed either over the lower front teeth or along the labial or front side of the teeth and then around the molars so that it provides both suction and displacement. This displacement of the tissues may usually be away from the ipsilateral side occupied by the suction component. The displacing component of this displacing suction component may be tubular, flat, or any other shape which provides both suction and displacement and may provide such functions in a relatively low profile. This may provide exposure for the dental practitioner and keep the moist tissues of the cheek and tongue away from the area being treated.

Figure 10:
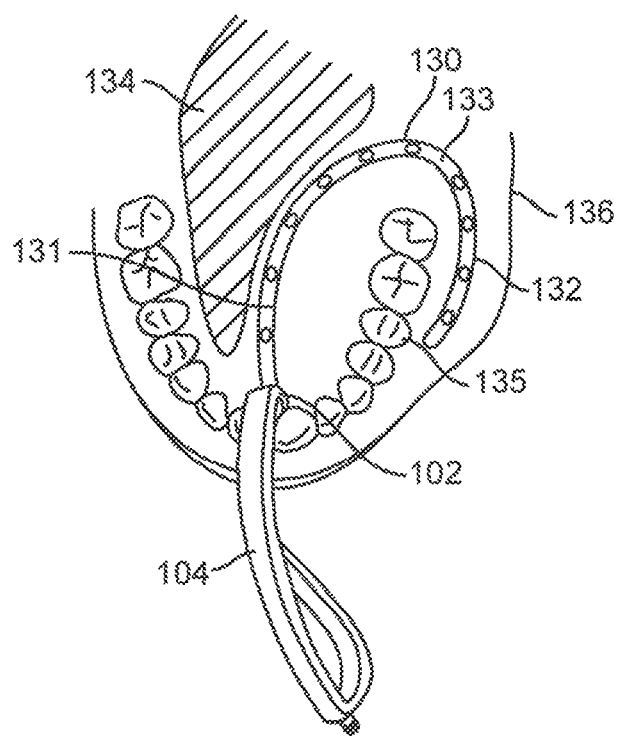
FIG. 10 is a top down perspective of the lower mouth with a mouth opening device, according to many embodiments.

An example of the device is shown in FIG. 10. The displacement mechanism is shown as attached to the device 90, for example, but it may be attached, affixed to or connected to any device which distracts the jaw downward and provides suction. In the devices in which the suction/distraction component is placed over the lower front teeth, as shown in FIG. 10, the suction/distraction component 130 may comprise a lingual component 131 adjacent to and displacing the tongue 134 and a labial component 132 which may be placed between the teeth 135 and the cheek 136 and may displace the cheek 136 away from the teeth 135.

The position of the suction and the displacing means may vary, depending on whether the device is placed so that it exits the mouth midline or on the right or left side and whether the side in which the device is placed is the ipsilateral or contralateral side of the mouth in which the dentist is working. Hence, multiple different configurations of the suction and displacement components are likely, as well as the attachment component to the suction and whether the suction is integral within the handle or a separate tubing, which may be attached to the device and on which side it is attached or connected to the handle.

Figure 11:
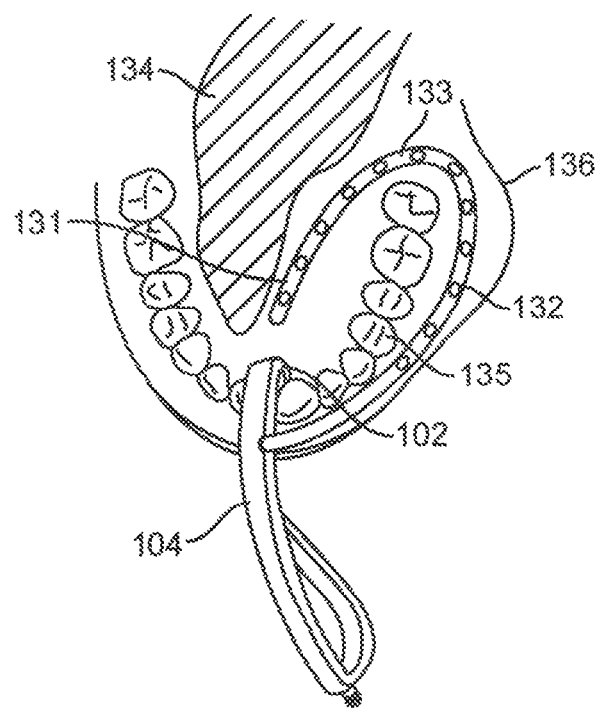
FIG. 11 is a top down perspective of the lower mouth with a mouth opening device, according to many embodiments.

In FIG. 11, the suction/displacement component 130 is attached to the distal aspect of the neck 104 of the traction device preferably on either side, but also possibly underneath or over the distal neck 104. The labial component 132 may comprise the proximal portion of the suction/displacement component 130 and may displace the cheek 136 while providing suction in that region. The lingual component 131 may comprise the distal portion and may provide displacement of the tongue 134 and suction in the floor of the mouth. Both may be tubular structures as illustrated with holes 138 to allow the fluids to enter and be removed.

Figure 12:
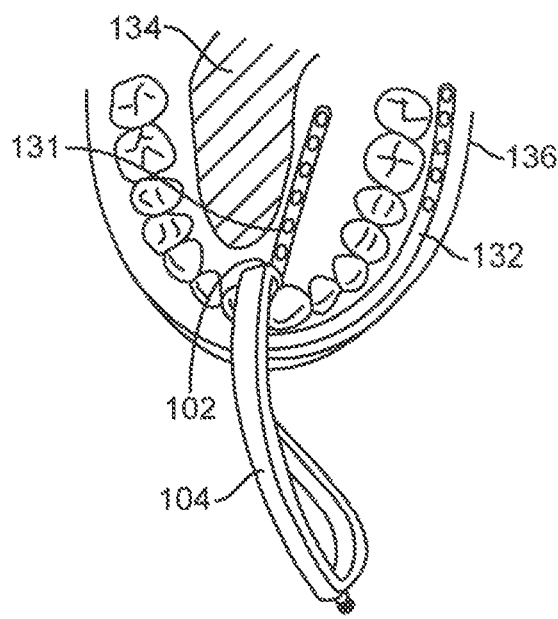
FIG. 12 is a top down perspective of the lower mouth with a mouth opening device, according to many embodiments.

In FIG. 12, the lingual portion 131 of the suction/displacement component 130 may originate from the tooth engaging portion 102 of the mouth opening device and the labial component 132 may originate from the distal neck 104 of the mouth opening device. The suction/displacement component 130 may be fixed to or releasably attached to the tooth engaging portion 102 or the handle 104 of the device in any number of ways, and the components may be attached to any of the different elements of the mouth opening devices described.

Figure 13:
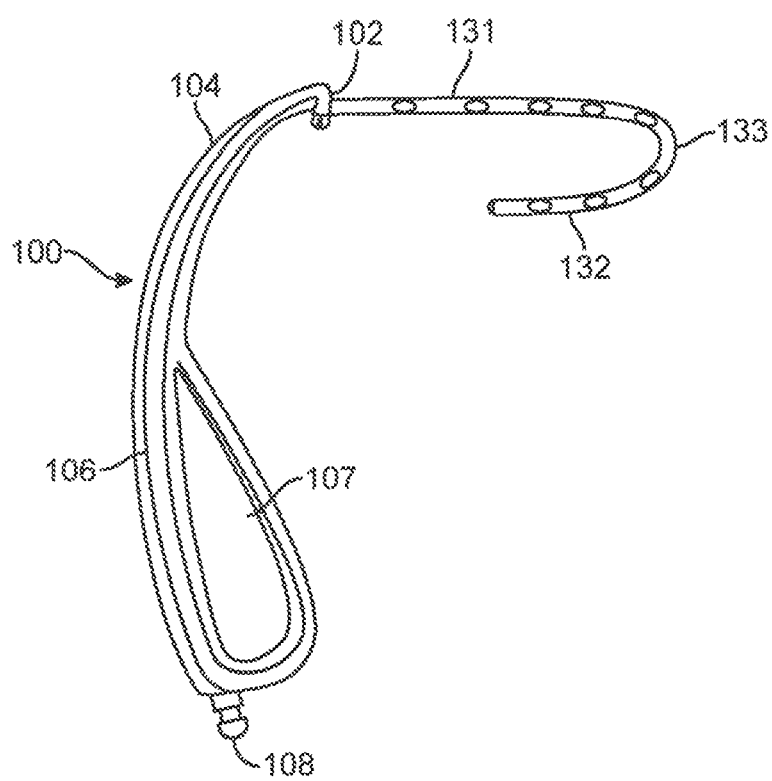
FIGS. 13, 14, and 15 are side perspectives of mouth opening devices, according to many embodiments.

In FIG. 13, the proximal portion of the suction/displacement component 130 is shown as attached to the tooth engaging portion 104, the lingual portion 131 being proximally positioned and the labial component 132 positioned distally.

Figure 14:
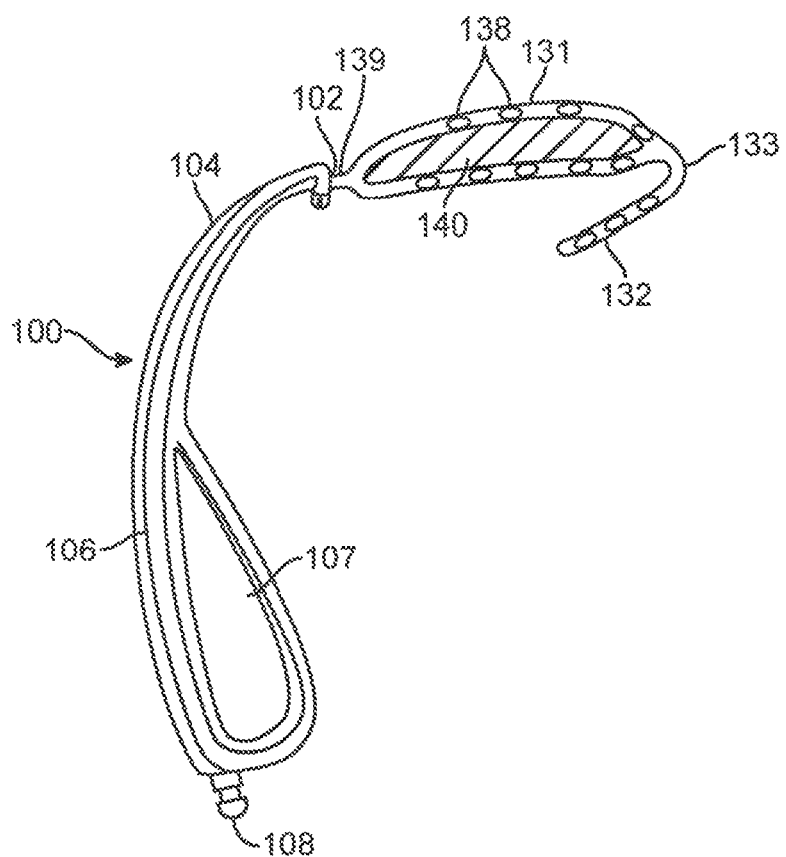

FIG. 14 demonstrates a similar configuration as FIG. 13, but the lingual component 131 may be wider than just a tubular structure. The lingual component 131 may comprise two tubes with holes 138 and a membrane 140 between the two tubes to keep them spatially separated. The membrane may be plastic or any one of a number of materials. Smaller tubes may even extend into the membrane 140 to provide additional suction to the lingual 131 and labial portions 132. Point 133 may be where the device wraps around the posterior molar and where the lingual portion 132 is directed forward in this and other embodiments herein. As shown, the membrane 140 is between the tubular structures, but it may extend beyond the margins of the tubular structures from 1 mm to 3 cm. Moreover, the membrane 140 may be constructed of or comprise a reflective material to enhance the available light within the mouth.

Figure 15:
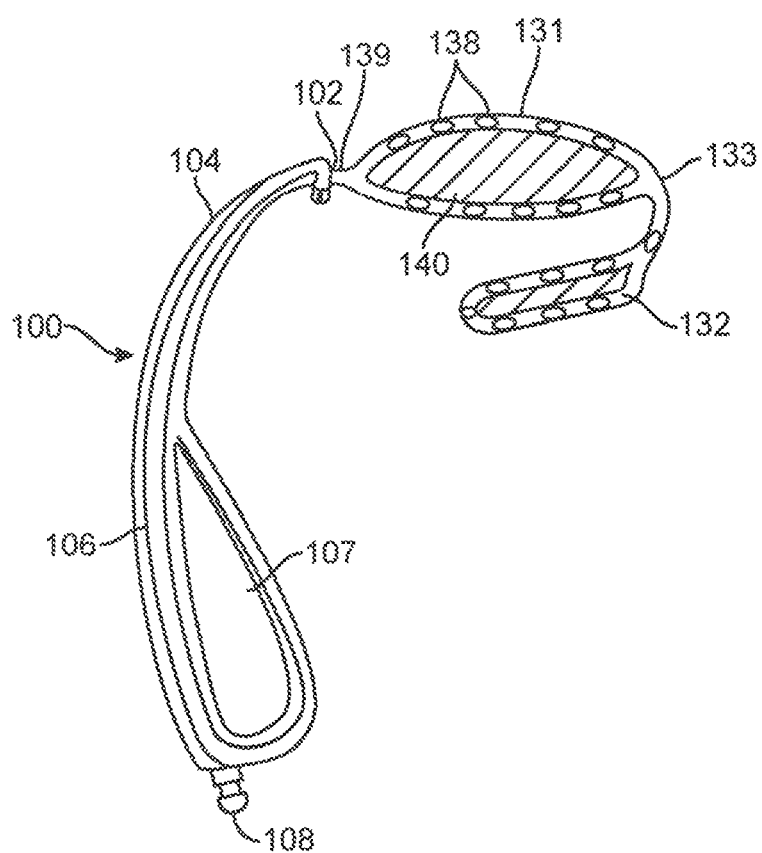

FIG. 15 demonstrates a configuration similar to that shown in FIG. 14, but the labial portion 132 may be a double tubular structure with a membrane 140 between the tubular structures. The point 133 may be a singular structure as shown to facilitate the curve around the posterior molars, but may be a double tubular or other structure (not shown) as well.

Figure 16:
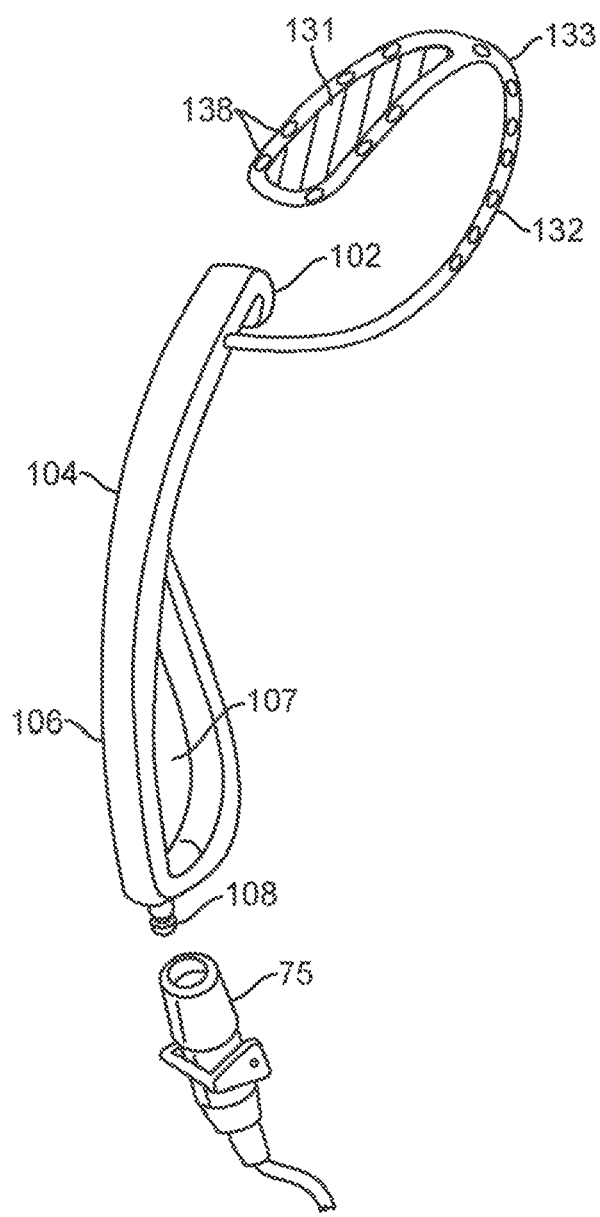
FIG. 16 is an oblique perspective of the device of FIG. 11.

FIG. 16 is a perspective of a mouth opening device configured similarly to that shown by FIG. 11. The labial component 132 is proximal and the lingual component 131 may be distal. It may be attached to any one of a number of points of the distal neck 104 of the device. Here it is attached to the side. The labial component 132 may displace the cheek and the lingual portion may displace the tongue.

The construction of suction/displacement component 130 may utilize any one of a number of materials including plastic, silicone, plyethylene, C-Flex, plyurethane, Chonoprene amongst others. A material of a durometer that maintains some stiffness but may be flexible enough to be comfortable may be used. In the one-piece configuration, it may be generally horseshoe shaped and may have a relatively low profile area 133 in the turn between the lingual 131 and labial 132 portions.

As illustrated herein, suction can be provided in a number of configurations, and thus, the described are merely examples of some of the configurations. Suction may be provided by just the suction tube, suction valve, and suction hose, or by providing connections between some of these suction components. The suction components also may attach to the elements of a device, to stabilize the suction apparatus. The elements of a device may stabilize the suction components by cradling the suction components, for example, rather than being connected or attached to them.

In any of the devices described herein, an added part or component may be provided to prop the mouth open. The devices of the present disclosure may be intended to keep the mouth open as described but may not prevent the patient from closing the mouth unexpectedly because of a sudden pain or impulse to close. Abrupt closing could potentially displace a drill, burr, or other dental device and may cause damage to the instrument, the patient, and/or the dentist or dental practitioner. Ideally in at least some cases, this propping mechanism may not actually prop the mouth open but may only serve to keep the mouth from closing significantly. In other words, it may function as a safety mechanism more than a means to keep the mouth open. The teeth may not about this component, unless and until the patient unexpectedly closes the mouth. For example, the mechanism may simply comprise a material added to the cephalic aspect of the tooth piece or may be a separate component which is releasably or fixedly attached to the distal aspect of the handle adjacent to the tooth piece. Alternatively, or in combination, these elements to prop open may be attached to the suction component or may be separate.

The devices described herein may also be used in concert with other commonly used dental devices, including dental dams and other devices. One may combine the current device(s) with a displacement device that displaces the tongue and cheek away from the targeted teeth. This may be accomplished, for example, by modifying the suction component as described herein to accommodate the displacement device and suction. One may also combine the mouth opening devices described herein with a lip retractor configured to retract the lips to gain better exposure to the oral cavity.

Additionally, a light or means of illumination may be added to the handle, the tooth piece, the suction component, or the displacement component, or it may be provided separately and attached to any of the components herein. Moreover, any of the components may be constructed of reflective material, which may serve to illuminate the teeth and oral cavity by reflecting light from the means of illumination described herein or from some other source of light. Even further, any of the components, and especially the displacing component, may be constructed of material that glows or emanates light when that substance contacts moisture or glows or emanates light because of some other physical or chemical reaction. This process could be because of fluorescence, chemoluminsecence, phosphorescence, light emitting diodes, or even organic light emitting diodes, among others. Any combination of light emitting substance and reflecting substance may be used.

The mouth opening device(s) described herein may also be made more visually attractive, which may be especially important when used in children. The mouth opening device(s) may comprise a detachable structure, a structure or attachment fixed to the device, or art applied to the device in one of several manners. While this visual component may represent an animate or inanimate object, one such structure may comprise a face or portions of a face that attaches to the neck to give the device a personality. This visual component may comprise one or more of eyes, mouth, ears, or nose and may represent an animal, person, plant, cartoon, or other figure. The visual component may be attached to, applied to, or incorporated into the neck or handle of the device. An exemplary visual component may be configured so that it may be removed from the device, preferably at the end of the procedure, and given to the patient. The visual component may be constructed so that it may be worn by the patient on clothing, in the hair, or even as a ring on a finger.

In maintaining a mouth of a patient in an open position during a dental procedure, methods of using the mouth opening device(s) described herein may comprise placing, by either the patient or the dental practitioner, a groove of a tooth engaging portion of a mouth distraction device over at least one lower tooth in a lower jaw of the patient's mouth and pulling down or providing traction on a handle of the mouth distraction device, preferably by the patient, to maintain the lower jaw in an open position relative to an upper jaw of the patient's mouth. This traction may be substantially continuous or intermittent. Suction may be provided by attaching a suction or vacuum source to or incorporating the suction or vacuum source within the distraction device. A tongue, cheek, or a tongue and cheek displacement element may be positioned by the dental practitioner to displace the tongue and/or cheek away from the area to be treated. A lip retraction element may also be positioned by the dental practitioner.

In at least some cases, optimally, the patient would provide downward traction on the mandible that would be sufficient to open the mouth as wide as possible while avoiding discomfort. The ideal balance of degree of distraction and the lack of discomfort can be achieved by the patient controlling the downward force of traction over the course of the procedure. The degree of distraction may be varied by the patient over the course of the procedure and may gradually increase as the initial traction causes the muscles of the jaw to relax. This variation may cause the jaw to open even more as the procedure progresses. The patient may intermittently close the mouth to relax, swallow or rest or may purse the lips about the neck of the device to evacuate the fluid within the mouth. Traction then may be reapplied by the patient to a degree that opens the mouth as wide as possible without generating discomfort. Repeating the traction, relaxation, and traction cycles may allow the mouth to open even further and without discomfort. By providing a handle that is rigidly affixed to the tooth engaging apparatus, the devices may maintain their relationship and prevent the tooth engaging portion from becoming displaced from the teeth when the patient closes the mouth to rest, relax, swallow, or evacuate fluid as may be the case with prior art devices. At the termination of the procedure, the device may be removed by the patient or the dental practitioner and properly disposed.

Special mention of the ability to evacuate saliva is in order. Standard saliva ejectors are plastic or metal tubes with a cap on the end in which there are slits for the saliva, water and other fluids to enter. These saliva ejectors are connected to suction tubes and eventually to a suction machine. They function moderately well but frequently the suction slits are adjacent to or touch soft tissue and oral mucosa, and the suction causes the soft tissue or mucosa to be sucked into the suction slits. This is uncomfortable and can damage the sensitive and delicate mucosa and soft tissues of the oral cavity. To prevent this, a dental assistant is needed to administer the suction intermittently when needed and to prevent the "grabbing" of mucosa and soft tissue by the suction tip. This adds unnecessary expense and complexity to the procedure as frequently the hands of the dentist and the dental assistant are all within or near the mouth. It is an object of a particular embodiment of the current invention to provide an atraumatic suction device which may be used as a saliva ejector that does not "grab" the mucosa or soft tissue, and provides more or less continuous suction, obviates the need for a dental assistant to provide suction and is comfortable and formable at the same time.

Some of the embodiments of the current mouth opening invention (FIGS. 1-9) may not need an improvement in the suction design as the suction holes or apertures are directly over the lower incisors in most cases and not near mucosa that could be inadvertently sucked into the slits or holes of the device. However, alternative embodiments, such as FIGS. 10-16, which have tubular structures extending to the posterior oral cavity, alongside the tongue, near the cheeks or into the tonsillar fossae may indeed tend to aspirate tissue along with fluids, especially if a high volume ejector (HYE) is utilized. Hence, in these instances without a dental assistant to provide and monitor the suction, protecting the tissues of the mouth while providing HYE suction is critical to keep from damaging the soft tissues. In the dental hygiene arena, ultrasonic scaling has recently become widely used to clean the teeth. This process uses more water than other procedures, mainly to dissipate the heat generated by the device. There is a need for the hygienist to evacuate the copious amounts of water in the mouth from this technique without an assistant present and to do so without grabbing or sucking tissue with the HYE suction.

Two other elements to consider are comfort and formability. The apparatus must be comfortable or it will not be tolerated by the patient, but at certain, but not all, times must be formable so it can be shaped for the individual patient's mouth or placed on the contralateral side. Formable elements are usually stiff and uncomfortable and frequently have a metal wire to provide stiffness, whereas comfortable tubes are usually soft but non-formable. Hence, there is a dilemma in providing a safe and comfortable saliva ejector or dental suction apparatus that solves all of the issues above in one device.

The accessory suction device of the current invention solves all five of these issues: 1) Protects the mucosa of the mouth during suction of saliva ejection, 2) Does not need an assistant to provide and monitor suction, 3) Is comfortable, and 4) Is formable into different shapes and lengths and 5) Is capable of evacuating large amounts of fluid from the oral cavity. This is accomplished by providing an inner suction tube that is firm and formable but is coaxially placed within a tubular mesh braid which provides the soft comfort that the inner suction tube does not. More importantly, the tubular braid displaces the tissues and mucosa away from the suction slits or holes of the suction tube and prevents the aspiration or sucking of tissue or mucosa by the inner tube which provides the actual suction. The inner tube is rather stiff and formable, but the tubular mesh braid covering it is soft and pliable causing the net result to be a comfortable configuration that will be readily accepted by the patient but one which can be modified for each particular patient and is capable of evacuating large volumes of fluid.

The tubular braid is preferably formed as a mesh of individual non-elastic filaments (or "yarns"), although it may have some elastic filaments interwoven to create certain characteristics. The non-elastic yarns can be materials such as polyester, PET, Polypropylene, polyamide fiber, composite filament wound polymer, extruded polymer tubing, stainless steel, Nitinol, or the like so that axial shortening causes radial expansion of the braid. These materials have sufficient strength so that the braid element will retain its expanded condition in the mouth while protecting the tissue from the inner suction tube shaft and the holes and/or slits in that piece as well as cushioning the pressure from the stiff and uncomfortable inner suction tube.

The braid may be of conventional construction, comprising round filaments, flat or ribbon filaments, square filaments, or the like. Non-round filaments may be advantageous to decrease the axial force required for expansion to create a preferred surface area configuration or to decrease the wall thickness of the tubular braid. The filament width or diameter will typically be from about 0.5 mils to 25 mils, usually from about 5 to 10 mils. Suitable braids are commercially available from a variety of commercial suppliers.

The tubular braids are typically formed by a "Maypole" dance of yarn carriers. The braid consists of two systems of yarns alternately passing over and under each other causing a zigzag pattern on the surface. One system of yarns moves helically clockwise with respect to the fabric axis while the other moves helically counterclockwise. The resulting fabric is a tubular braid. Common applications of tubular braids are lacings, electrical cable covers, "Chinese hand-cuffs" and reinforcements for composites. To form a balanced, torque-free fabric (tubular braid), the structure must contain the same number of yarns in each helical direction. The tubular braid may also be pressed flat so as to form a double thickness fabric strip. The braid weave used in the tubular braid of the present invention will preferably be of the construction known as "two dimensional, tubular, diamond braid" that has a 1/1 intersection pattern of the yarns which is referred to as the "intersection repeat." Alternatively, a Regular braid with a 2/2 intersection repeat and a Hercules braid with an intersection repeat of 3/3 may be used. In all instances, the helix angle (that being the angle between the axis of the tubular braid and the yarn) will increase as the braid is expanded. Biaxially braided fabrics such as those of the present invention are not dimensionally stable. This is why the braid can be placed into an expanded state from a relaxed state (in the case of putting it into the compressive mode). When put into compression the braid eventually reaches a state wherein the diameter will increase no more. This is called the "Jammed State." Much of the engineering analysis covering braids are calculated using the Jammed State of the structure/braid. These calculations help one skilled in the art to design a braid with desired characteristics. Further, material characteristics are tensile strength, stiffness, and Young's modulus (elasticity) amongst others. In most instances, varying the material characteristics will vary the force with which the expanding condition of the tubular braid can exert radially. Even further, the friction between the individual yarns has an effect on the force required to compress and un-compress the tubular braid. For the present invention, the desired characteristics and function are maintaining enough radial force to displace the inner suction tube away from the tissues of the mouth or displacing the tissues away from the inner suction tube for both patient comfort in tolerating the presence of the device and preventing the aspiration of tissue by the suction inlets. This is best achieved by utilizing the tubular braid in a compressed, but not Jammed State. The Jammed State may reduce flexibility and the interstices of the braid may be diminished so that fluid is impeded from flowing freely through the fully compressed braid. Hence, applying the braid to the inner suction tube in a compressed state which approaches, but does not achieve, the Jammed State is preferable.

Tubular mesh braid can be constructed in any one of many ways. Usually a weave pattern is utilized where each member crosses under an intersecting member and then over the next intersecting member, and so on. If the braid is elongated, it has very little outward radial force, but when the ends are compressed and brought closer together, the tube of braid expands outwardly and does gain force and strength as the members develop an angle that approaches 90 degrees more so than in the elongated configuration. It is in this state, i.e., when the ends of the tube of mesh braid are compressed together, that the braid will gain radial strength and be able to shield the suction slits and holes from tissue or mucosa. The braid is still compressible and flexible, hence, comfortable. It is in this moderately compressed state that the braid will also provide an optimized comfortable cover to the stiff and uncomfortable inner suction tube, although simply applying a relaxed braid coaxially over the inner suction tube may indeed function fairly well.

Figure 17A:
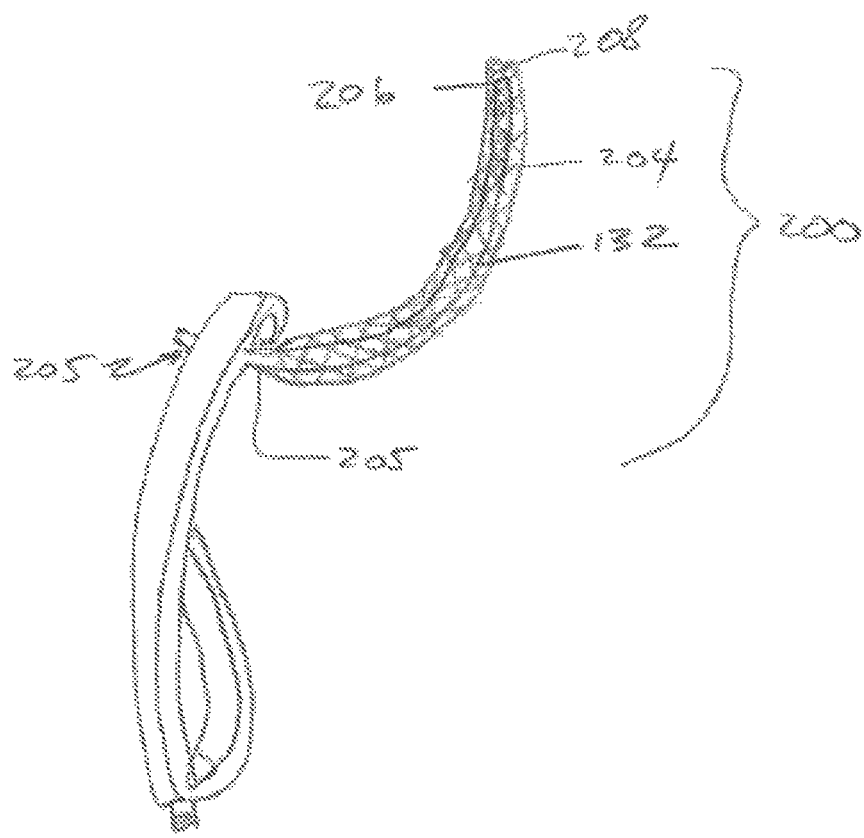
FIG. 17 A is a side perspective view of a mouth opening device, according to many embodiments.
FIG. 17B is a top down perspective view of the lower mouth with the mouth opening device of FIG. 17 A placed therein.
Figure 17B:
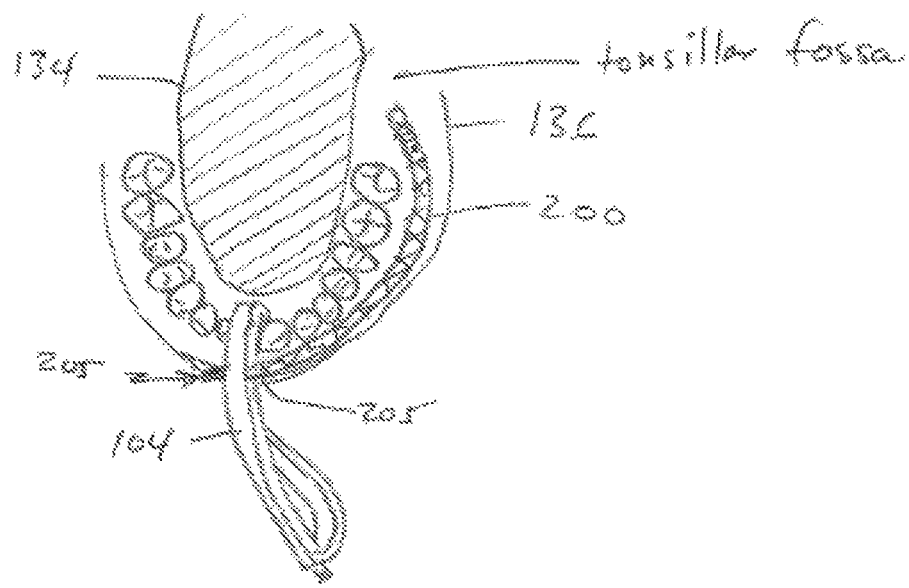
Figure 18:
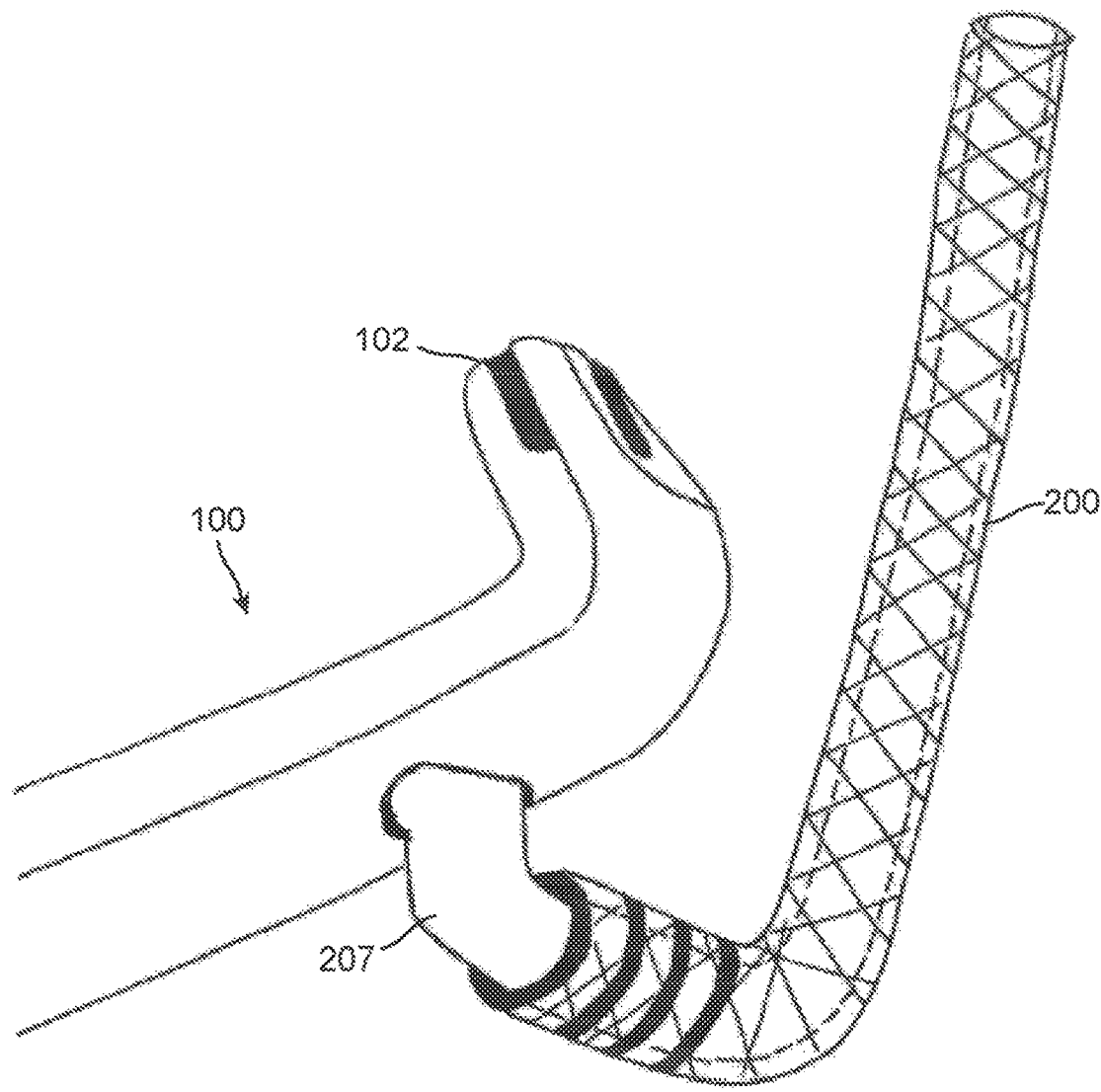
FIG. 18 is a magnified perspective view of the tooth capturing end and suction tube of a mouth opening device, according to many embodiments.

The above coaxial configuration of an inner suction tube and an outer sleeve of tubular mesh braid are collectively referred to as the suction apparatus and are detailed in FIGS. 17A and 17B. The suction apparatus 200 is attached to the mouth opening device 100 described earlier either from the dorsal or ventral aspect or from one of the sides of that device. The holes or inlets 138 in the tooth engaging portion 102 may be either covered or omitted from the design in the case of alternative suction devices. The suction apparatus 200 may be attached to the mouth opening device 100, which comprises a suction channel within, by means of an attaching mechanism that may take any one of several configurations and may include a simple friction fit of the suction tube apparatus 200 over or within a fitting that is attached to the mandibular traction or mouth opening device 100. In one embodiment the fitting is an elbow fitting 207 as demonstrated in FIG. 18 directed more or less perpendicularly to the axis of the mouth opening device 100 which may be removable and directed to either right or left sides. In other configurations, the fitting may be small nipples 205 as shown in FIGS. 17A and 17B projecting off either side of the mouth opening device amongst other configurations. In this case, suction apparatus may be provided for both right and left sides or, in the case of providing just one suction apparatus, small caps may be placed over the nipple not being utilized. The suction apparatus may also be connected to the tooth engaging portion of the mouth opening device by a fitting (not shown) or a sleeve (not shown) which attaches the suction apparatus 200 to the mouth opening device 100. As well, the suction tube apparatus 200 may be connected to other suction tubes, other devices or may be used as a standalone device (not shown).

Figure 19A:
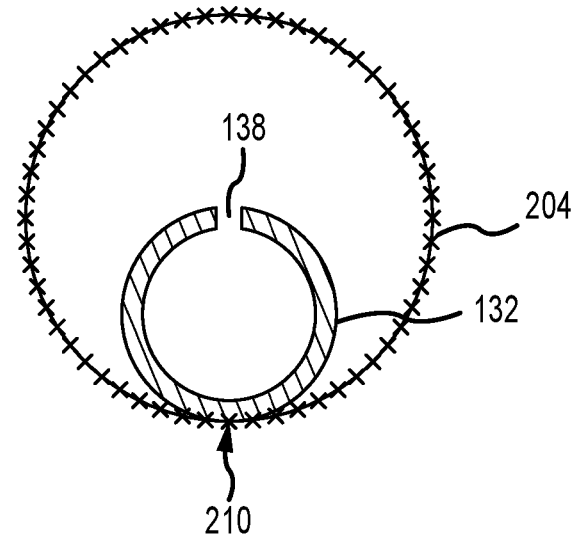
FIGS. 19A and 19B show cross-sectional views of a suction tube apparatus for use with a mouth opening device, according to many embodiments.
Figure 19B:
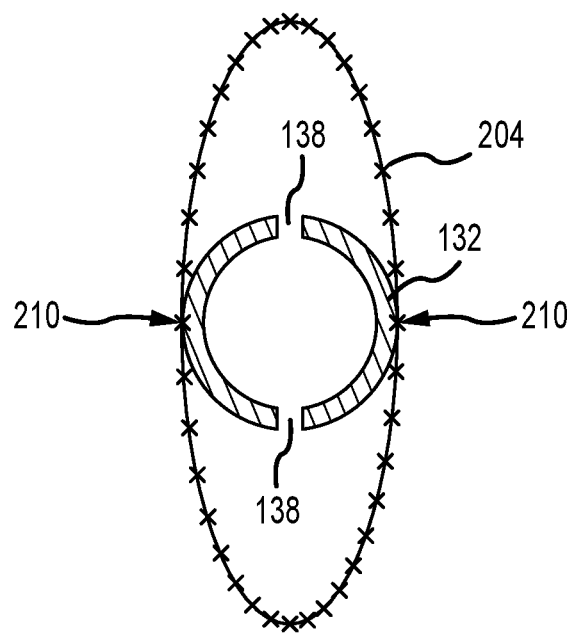

The suction tube apparatus 200 may include an elongate suction tube 312 with holes or slits 138 at least in the distal end, placed inside an expandable tubular braid 204. The tubular mesh braid 204 may extend from the proximal portion of the inner suction tube 132 to at least the distal end 206 of the inner suction tube 132, and in different embodiments may extend past the distal end 206 of the inner suction tube 132. This is illustrated in FIG. 17 in which an inner suction tube 132 is placed coaxially within a more or less compressed tubular braid 204. In this configuration, the suction apparatus 200 is configured to extend into the tonsillar fossa of the oral cavity where fluid frequently collects. If the distal end hole of the inner suction tube is left open, it is important that the tubular braid comprises a section 208 that extends beyond the distal end 206 of the inner suction tube 132 so that it encloses the distal end hole 209 and protects the tissue from being sucked into the distal end hole. To construct the coaxial device, one may compress the tubular braid from end to end and bond the tubular braid to the inner elongate suction tube while the braid is being compressed. The bond may be a heat bond, chemical bond or other means. Bonding the tubular braid to the inner suction tube while the braid is being compressed will give the braid sufficient radial outward force to displace tissue away from the shaft of the inner suction tube hence making the whole structure more comfortable to the patient, and most importantly, keep the tissues away from the slits and holes in the inner suction tube and prevent the aspiration of tissue by the suction. The braid may be bonded to the inner suction tube at or near the proximal end and at or near the distal end, and it may be bonded to the inner suction tube at other locations along the shaft of the inner suction tube. As detailed in FIGS. 19A and 19B, which are cross sections of the improved suction apparatus 200, the bonds 210 may be placed strategically on the device so that the bond 210 is on the opposite side of the inner suction tube 132 from any holes or slits 138 as in FIG. 19A. This would ensure that the braid 204 would not approximate the holes or slits 138 and allow any tissue to approximate the holes or slits 138. In fact, the bonds 210 may be arranged on either side of the inner suction tube 132 as in FIG. 19B which would cause the braid to take on an elliptical shape vs. the cylindrical shape.

The foregoing explanation is important in the construction of the current suction apparatus and to achieve the desired goals as simply placing a braid over the inner suction tube or the distal end of the inner suction tube will not achieve the desired goals. Bonding the tubular braid to the inner suction tube in a moderately compressed state is feasible and advantageous. Simple heat bonding of the braid and inner suction tube, or other methods, may be readily utilized for that portion of the braid which overlies the inner suction tube. Heat bonding, chemical, and other methods of bonding are all feasible. It is anticipated that the tubular mesh braid 204 and the shaft of the inner suction tube 132 be related chemically with similar physical properties for facilitate whichever means of bonding is chosen. If a polymer is chosen as the material for the braid and shaft of the inner suction tube, then choosing a material for each from the same or a related polymer family is anticipated to facilitate the bonding process.

However, extending the tubular braid beyond the distal end of the inner suction tube and maintaining it in a compressed state so that it maintains outward radial forces may be problematic as there is no anchor to maintain the compression of the tubular braid extending beyond the distal end of the inner suction tube. This section of the tubular braid will elongate and loose its radial outward strength or force and not protect the distal end hole of the inner suction tube from sucking the braid and the adjacent tissue into at least close proximity, if not immediately adjacent to, the suction apertures and the distal end hole. To address this dilemma, FIGS. 20A-20C demonstrate potential solutions. FIG. 20A demonstrates that attaching the tubular braid 204 to the distal inner suction tube 132 with a bond 210 of choice, closing the distal end hole of the inner suction tube 132 and placing the suction apertures or inlets 138 proximal to the end 206 of the inner suction tube 132 where they will be protected or covered by the compressed tubular braid is a potential solution. Another configuration shown in FIGS. 20B and 20C that solves this dilemma may be to place and attach an extension member between the distal end of the inner suction tube and the tubular braid end that extends beyond the distal end of the inner suction tube. This member may anchor the distal end of the braid in a compressed state, or at least serve to anchor the braid end in more or less a compressed state hence "protecting" the distal end hole. This extension member may be a separate structure, such as a more or less linear strut that is bonded to both the distal end of the inner suction tube and the end tubular braid securing in a more or less compressed state extending beyond the end of the suction tube. A string like member not shown) that tethers the distal end of the tubular braid to the end of the inner suction tube may maintain the end of the braid in a compressed state and preserve the characteristics needed to keep the tissues away from the inner suction tube inlets. As illustrated in FIG. 20B, the extension member may be an extension of a stiffening wire 201 that may be a part of the inner suction tube 132 to give it formability. The wire 201 creates problems in that it is stiff and may injure tissues. Also, the bond 210 to the braid 204 may have to be a metal compression fitting 202 that also may be uncomfortable to the tissues and may cause injury.

As demonstrated in FIG. 20C, the extension member 208 also may be comprised of a portion of the shaft of the inner suction tube 132 that extends beyond the distal end hole 209. Simply removing approximately half or more of the wall of the cylindrical inner suction tube 132 over the distal 1-2 cm or so may provide the extension member 208 needed to anchor the distal braid in a more or less compressed state while effectively placing the distal end hole of the inner suction tube remote from the braid end.

Figure 21:
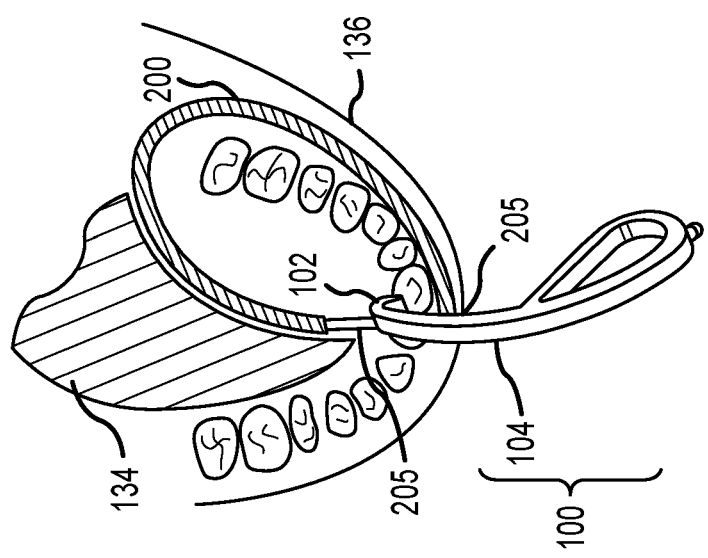
FIG. 21 shows a top down perspective view of the lower mouth with a mouth opening device, according to many embodiments.

FIG. 21 demonstrates an improvement on the configuration of FIGS. 10-20. The improved suction apparatus 200 described herein is utilized, as it may be with the configurations of FIGS. 10-20, but the suction apparatus 200 of FIG. 21 is connected to the mouth opening device 100 at least two points or locations 205. This serves two purposes: 1) It provides more uniform suction throughout the suction apparatus 200, and 2) It provides stability and strength to the device as it displaces the tongue 134, cheek 136 and other tissues away from the teeth that need instrumentation. These connections 205 may be fittings as described herein, sleeves or alternative fittings or methods, which may be placed on the dorsal or ventral surfaces or sides of the neck 104 of the mouth opening device 100 and may be connected to the tooth engaging portion 102 of the mouth opening device 100 as shown. In this configuration, there may be no need for the embodiments detailed in FIGS. 20A-C.

A method of utilizing the embodiment of FIG. 21 may entail placing the mouth opening device 100 into the mouth and over the lower front teeth while having one end of the improved suction apparatus 200 already attached to the mouth opening device 100. The dental practitioner then would place the improved suction apparatus 200 in appropriate position within the mouth so that it comfortably displaces the tongue 134 and cheek 136 and is positioned for optimal suction. The second end of the improved suction device may then be connected to the mouth opening device 100.

Figure 22:
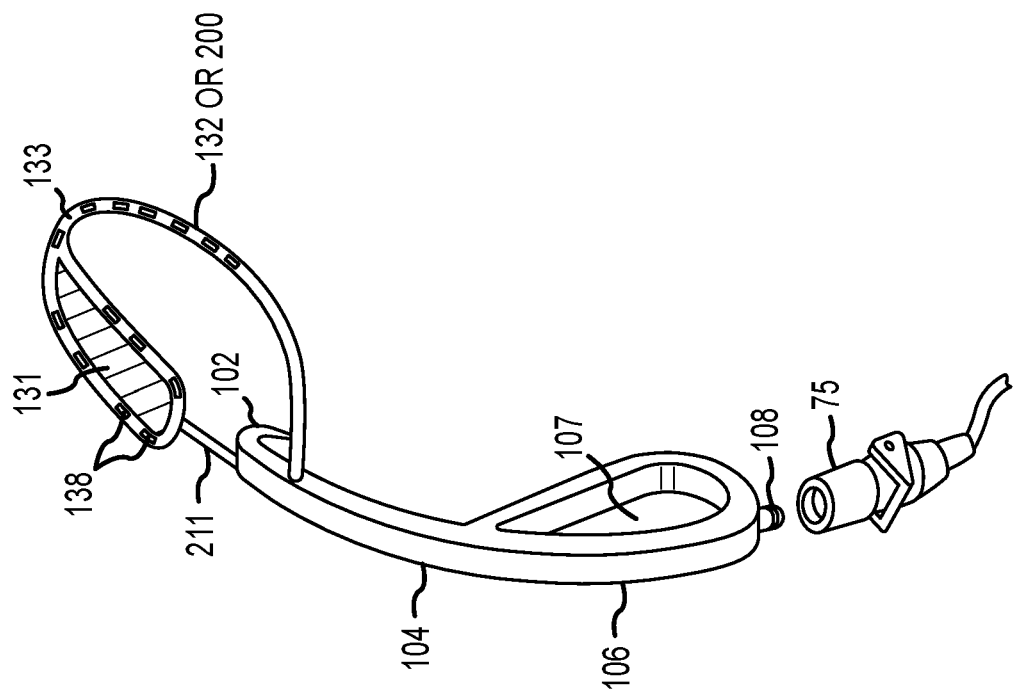
FIG. 22 shows a side perspective view of a mouth opening device with a suction apparatus coupled thereto at two suction ports, according to many embodiments.

Alternatively, the improved suction apparatus 200 may be utilized in configurations of FIGS. 13-16 in which loops may be formed to better displace the tongue 134 and cheek 136 away from the teeth of operatory interest. In these instances, a second connection to the mouth opening device 100 may be accomplished as demonstrated in FIG. 22 but may or may not provide for suction. The second connection may be for stability only. If this second connection is for stability only, it may take any one of several forms and configurations including a clip or attachment 211 to secure the improved suction apparatus 200 or just the inner suction tube 132 to the mouth opening device 100. This attachment 211 may be adjustable by one of several means so that after comfortably displacing the tongue 134 away from the teeth of interest, the dental practitioner may displace the tongue even more by extending the length of the attachment means 211 and forcing the tongue to the side of the mouth even further hence providing more exposure for the practitioner. The means (not shown) for connecting the attachment mechanism 211 to the suction apparatus 200 and the mouth opening device 100 may be constructed so the tongue displacement apparatus may be purposefully and forcefully positioned a selected and variable distance away from the connection point of the mouth opening device 100.

Figure 23:
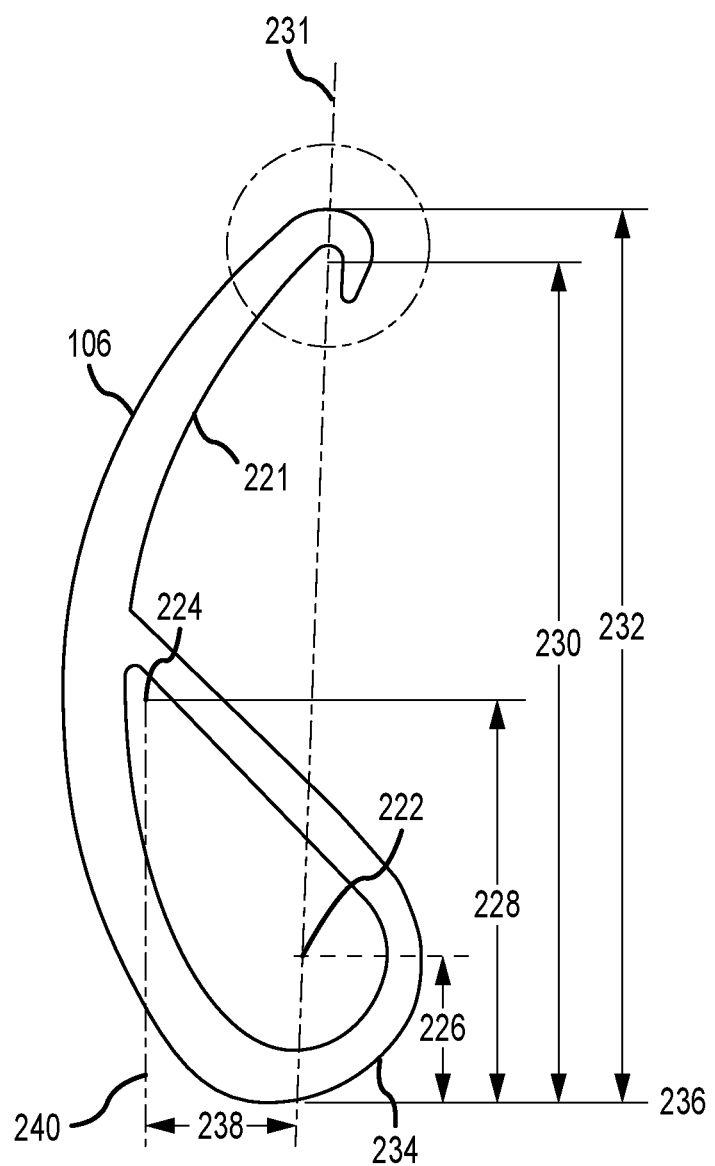
FIG. 23 shows a side view of a main body, including its handle, of a mouth opening device, according to many embodiments.

FIG. 23 is an illustration of a handle 106 used to retract the temporomandibular joint. The handle 106 is shown with a pronounced arc which begins at the tooth hook 223 (See FIGS. 24A-B) to and terminates at proximal radius 222. This arc allows for the handle 106 to sweep around the chin and terminate at the proximal handle configuration. 230 defines the arc, when 230 is short it brings the hook to the finger loop diameter 226 closer causing the handle to bulge outward bringing the finger loop 226 closer to the chin causing a unnatural and more uncomfortable situation whereby the hook 223 pulls the tooth out of its natural position. The optimum length for the distance 230 is between 4 and 10 inches. Handle 106 ranges in length 232 from 2.00 inches to 24.00 inches in length from hook to baseline 236. The cutout for the finger engagement is defined by minor radius 224 which is measured from the baseline 236 distally 228 approximately 0.50 inches to 10.00 inches. It is biased from the longitudinal axis 231 by distance 238 to centerline 240. This length can range from 0.25 inches to 2.00 inches in length. Major radius 222 forms the longitudinal axis 231 with radius 222. Length 226 can range from 0.25 inches to 4.00 inches from baseline 236 measured from its center point. The distance between minor radius 224 and major radius 222 defines the "Tear Drop" shape a shown. For instance, the closer the minor radius 224 is to the major radius 222 the more the tear drop becomes a circle. The opposite is true when the minor diameter 224 is further away from the major radius 222 the tear drop becomes more pronounced. In this embodiment the tear drop is formed by minor radius 224 being approximately 0.125 inches and approximately 1.00 inches off longitudinal axis 231, the major radius 222 being approximately 1.00 inches and on the longitudinal axis 231. The cutout can be used by any finger of either hand but as an example using the thumb the weight of the hand provides enough downward traction as to comfortably relax the temporomandibular joint.

Figure 24A:
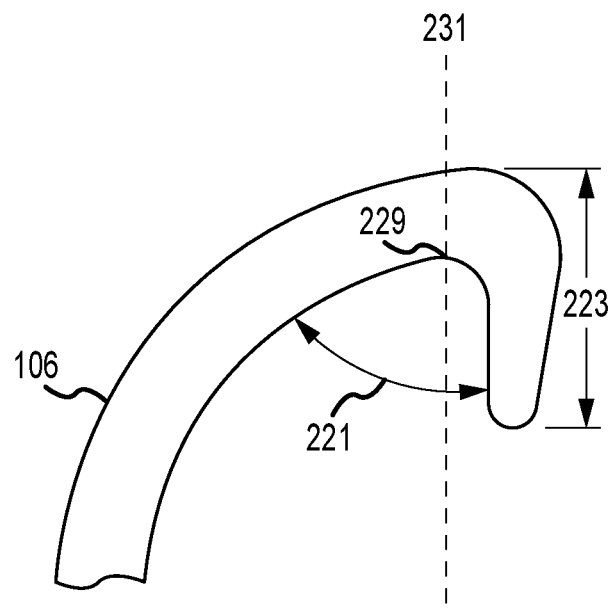
FIGS. 24A and 24B show side views of the tooth hook of the mouth opening device of FIG. 23.

FIG. 24A is an enlarged view of the hook 223. The hook 223 is defined by internal radius 229 which in turn defines angle 221. As an example, internal radius 109 can be very acute being 0.020 inches which in turn translates into approximately 25 degrees of engagement from the tooth face 235 which is parallel to longitudinal axis 231. This allows for a very tight purchase on the lower mandible, engaging one or more teeth. The angle 221 can range from 5 to 110 degrees but is preferably between 30 and 90 degrees. The hook 223 length is defined by radius 225 plus length 223 terminating at radius 227.

Figure 24B:
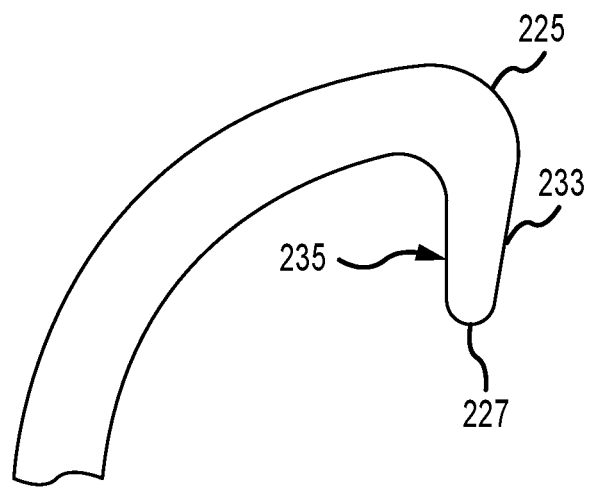

FIG. 24B is an enlarged view of the hook 223 with tooth face 235 which engages one or more teeth's inner surface. On the hook 223 is a radius 227 at its distal tip which is provided to mitigate irritation to the tissue of the gum.

Figure 25B:
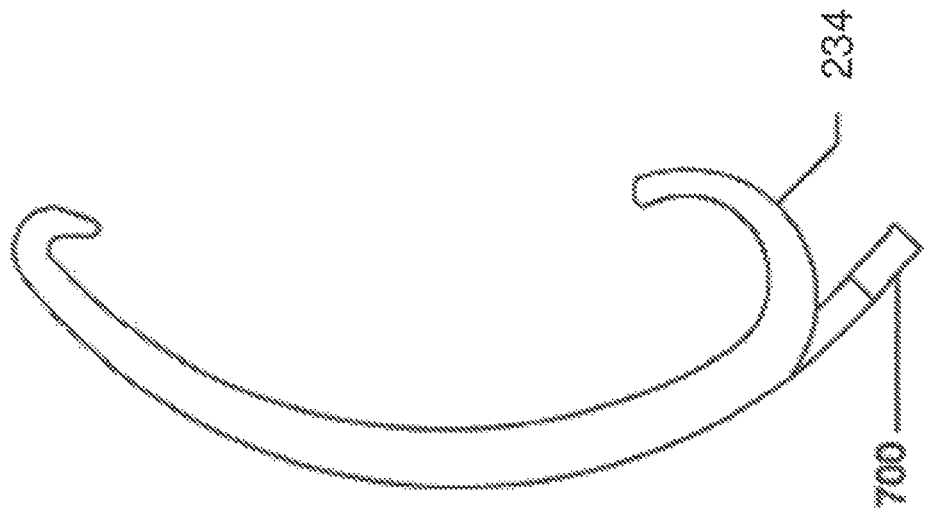
FIGS. 25A and 25B show side views of the handles of various mouth opening device, according to many embodiments.
Figure 25A:
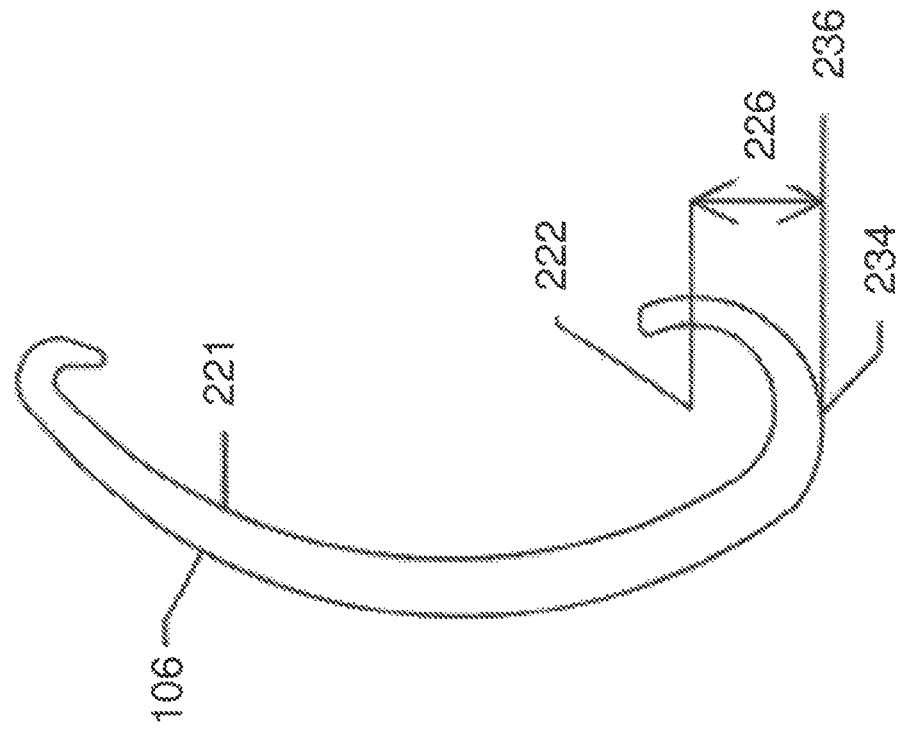

FIG. 25A is an illustration of a handle with open loop 234. Radius 222 is sized from 0.25 inches to 2.00 inches and is located at center point 226 which is 0.25 inches to 2.00 inches from baseline 236. The end of the open loop described can be contiguous and end at or before 230 of inner arc 221 of handle 300 with or without joining inner arc 221.

FIG. 25B is an illustration of a handle with suction attachment 700 at proximal end of open loop 234. The suction attachment 400 is sized to accept standard suction tubing (not shown) with inner diameters ranging from 0.0625 inches to 0.50 inches.

FIG. 26A is an illustration of handle 106 with formable distal tip 250 allowing for adjustment of purchase angle. The distal tip 250 is compliant and can be bent by hand at 260 on axis 255. It will take a set due to a looped wire backbone (not shown). The distance of the bended section can be adjusted from 0.125 inches to 0.75 inches long. The length of the formed tip 250 is defined by the length 230.

FIG. 26B is an illustration of handle 106 with formable distal tip 250. Angle 275 can be from 10 to 90 degrees and is defined by radius 270.

FIG. 26C is an illustration of handle 106 with suction attachment 700 sized to accept standard suction tubing (not shown) with inner diameters ranging from 0.0625 inches to 0.50 inches.

Figure 27C:
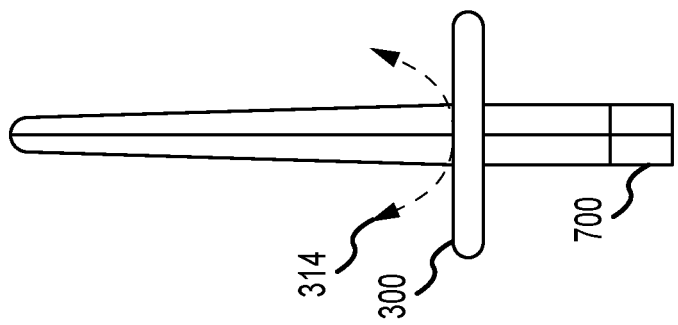
FIGS. 27A, 27B, and 27C show end views of the handles of various mouth opening device, according to many embodiments.
Figure 27B:
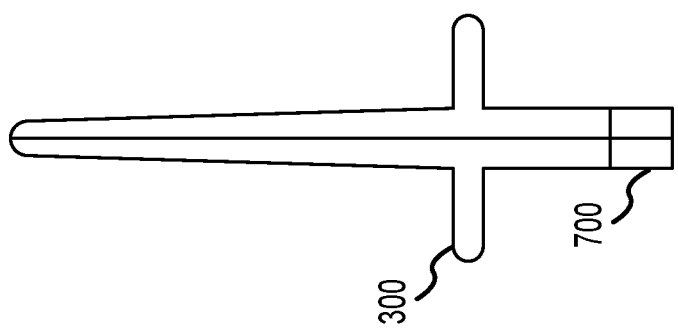
Figure 27A:
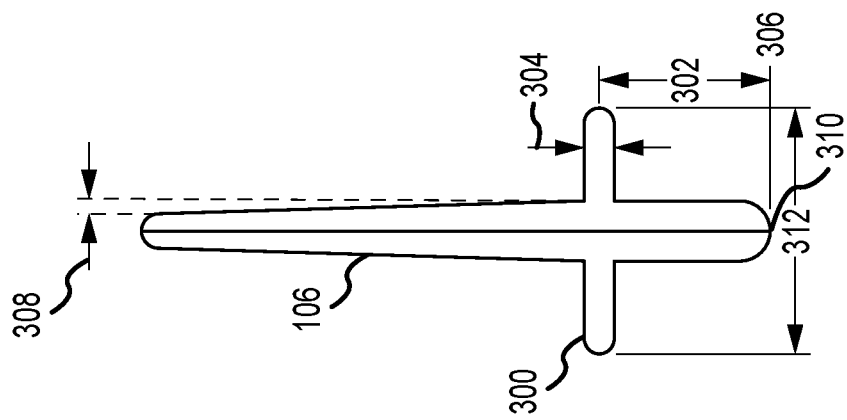

FIG. 27A is an illustration of end view of "T" handle 300. The height of the "T" is defined by the distance 302 from baseline 306 which can range from 0.50 inches to 10.0 inches in length. The diameter of each arm 304 can be from 0.125 inches to 0.50 inches. The shape of each arm 304 can be round, oval, square and hexagonal (not shown). The width 312 can be centered to the body or offset and can range from 1.00 inches to 4.00 inches in length. Additionally, there is a radius 310 provided at the proximal end of the handle. Draft angle 308 is tapered distal to proximal with the distal end being of a smaller shape than the proximal end of the handle 106.

FIG. 27B is an illustration of the end view of the "T" handle 300 with suction attachment 700 sized to accept standard suction tubing (not shown) with inner diameters ranging from 0.0625 inches to 0.50 inches.

FIG. 27C is an illustration of the end view of the "T" handle 300 where the "T" 300 can rotate 360 degrees in either direction 314. The suction attachment 700 is sized to accept standard suction tubing (not shown) with inner diameters ranging from 0.0625 inches to 0.50 inches.

Figure 28C:
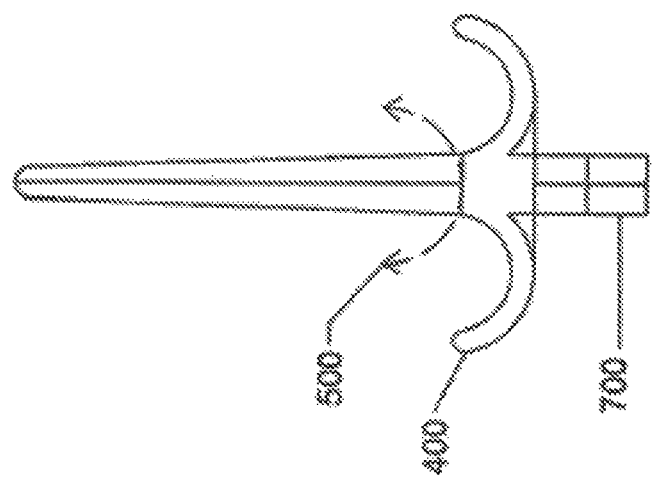
FIGS. 28A, 28B, and 28C show end views of the handles of various mouth opening device, according to many embodiments.
Figure 28B:
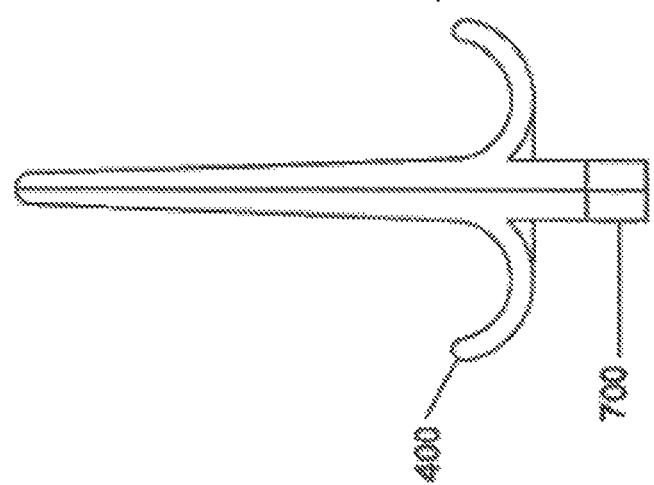
Figure 28A:
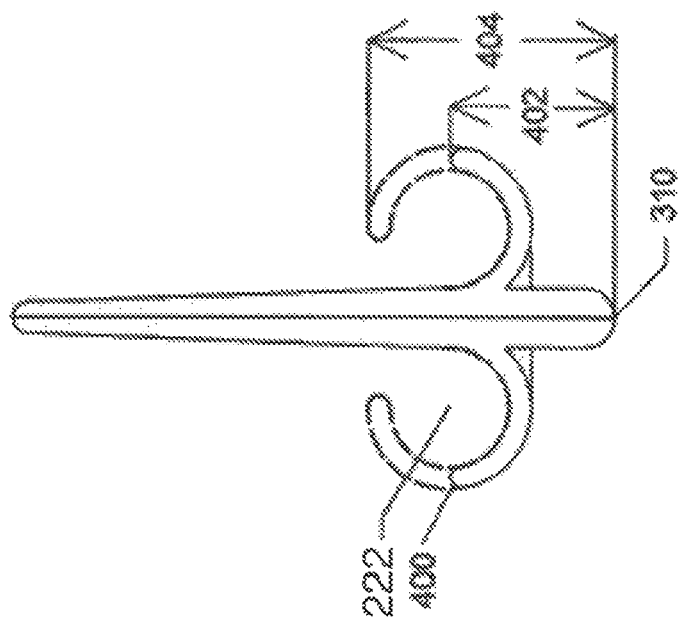

FIG. 28A is an illustration of the end view of a double open loop 400 configuration. The open radii 222 of open loop 400 can begin at 15 degree and continue through to 359 degrees. Open loop 400 is shown at 45 degrees 402. The open loop 400 is also shown (dotted line) at the 180-degree position 404. Additionally, there is a radius 310 provided at the proximal end of the handle. These loops are intended to be used by the index and middle fingers predominantly but do not exclude the thumb and or index finger use.

FIG. 28B is an illustration of the end view of open loop handle 400 with the suction attachment 700 sized to accept standard suction tubing (not shown) with inner diameters ranging from 0.0625 inches to 0.50 inches.

FIG. 28C is an illustration of the end view of open loop handle 400 which is separately disposed on handle 106 and can rotate 500 separately. It is also provided with a suction tube attachment 700 which is proximal to the rotating handle 500 and is of a length so as to accept a standard suction tube (not shown) with inner diameters ranging from 0.0625 inches to 0.50 inches.

Figure 29C:
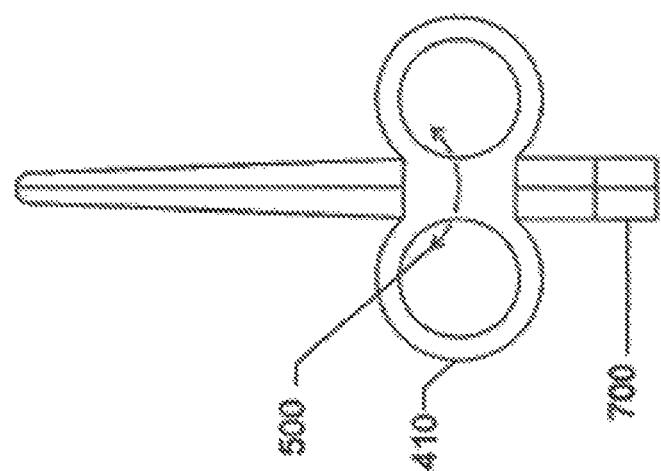
FIGS. 29A, 29B, and 29C show end views of the handles of various mouth opening device, according to many embodiments.
Figure 29B:
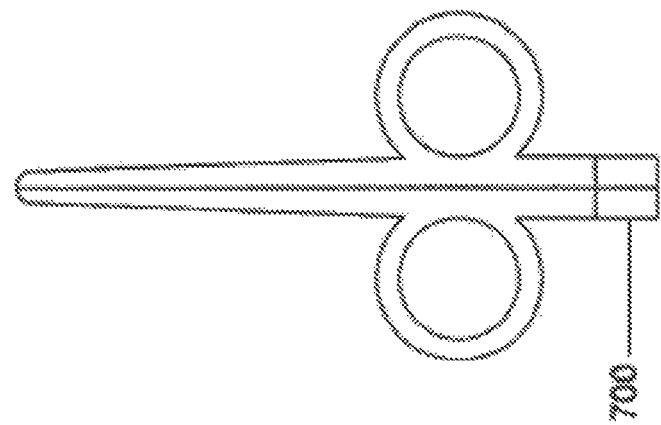
Figure 29A:
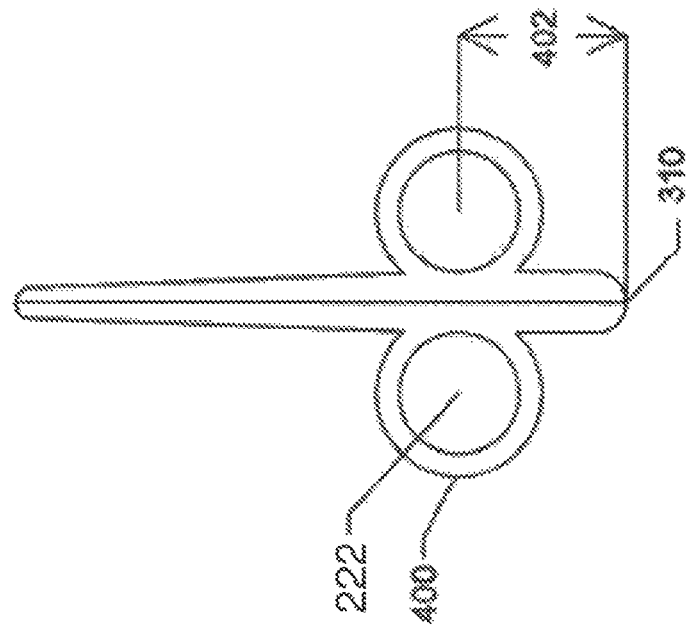

FIG. 29A is an illustration of a front view of handle 106 with double closed finger looped configuration 400. The radius 222 is between 0.25 inches and 2.00 inches. Its height from the proximal end of the handle 106 is defined by distance 402. 402 correlates directly with radius 222, if radius 222 is large then distance 402 must be in turn longer so as to accommodate larger finger loops. These loops are intended to be used by the index and middle fingers predominantly but do not exclude the thumb and or index finger use.

FIG. 29B is an illustration of the end view of open loop handle 400 with the suction attachment 700 sized to accept standard suction tubing (not shown) with inner diameters ranging from 0.0625 inches to 0.50 inches.

FIG. 29C is an illustration of the end view of closed loop handle 410 which is separately disposed on handle 106 and can rotate 500 separately. It is also provided with a suction tube attachment 700 which is proximal to the rotating handle 500 and is of a length so as to accept a standard suction tube (not shown) with inner diameters ranging from 0.0625 inches to 0.50 inches.

FIG. 30A is an enlarged view of the distal tip of handle 106 illustrating the front view of the hook component 223 in its normal or longitudinal position on longitudinal axis 231.

FIG. 30B is an enlarged view of the front view of the hook 223 in its swung or angled position 239 off of longitudinal axis 231. The hook 223 can be of various shapes and sizes—for example the hook can be primarily square, oval or triangular in nature or combinations of all or some.

FIG. 31A is an illustration of a handle 106 with a secondary zig zag tether 700. It is provided at the proximal end of handle 106 and composed of an elastic material but not limited to silicone. It is independently assembled, or it can be made as a continuation of a silicon or other elastic based handle 106. At the proximal most aspect of the zig zag element 700 is a finger loop 702 which can be made as a continuation of the zig zag element 700 or independently assembled to.

FIG. 31B is an enlarged view of 700 zig zag configuration of the elbow angle 704. The angle of each elbow can range from 5 to 30 degrees prior to expansion for instance and as much as 45 to 180 degrees as an example after traction on finger loop 702.

FIG. 31C is an illustration of the handle 106 under traction using finger loop 702 elongating the zig zag element 700.

Figure 32:
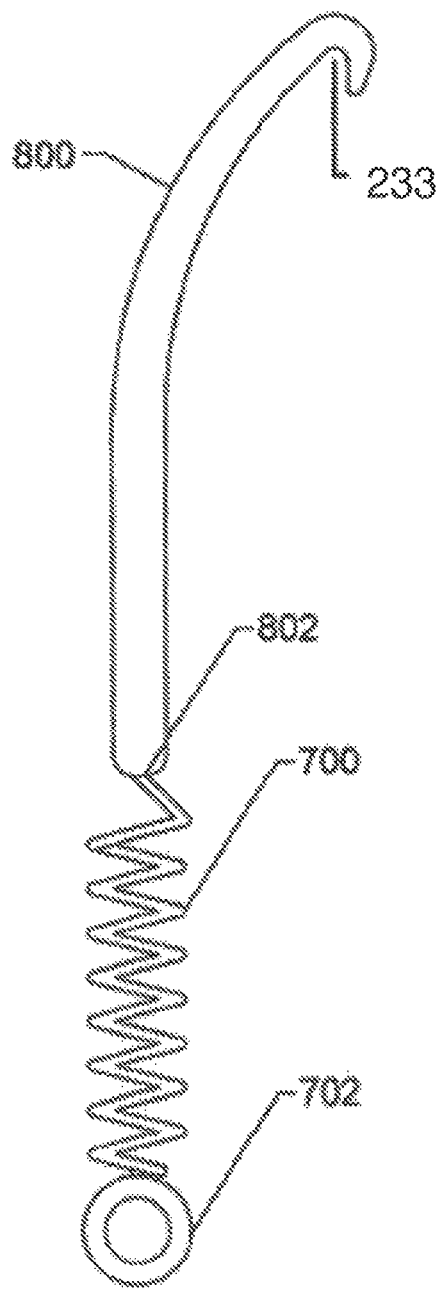
FIGS. 32 show side perspective views of a mouth opening device with an elastic zig zag element that can be pulled downward, according to many embodiments.

FIG. 32 is an illustration of a handle 800 provided with an elastic zig zag element 700 assembled to its most proximal end 802. Additionally, the handle 800 and zig zag element 700 could be made as a single unit whereby the durometer of the handle 800 would be of sufficient hardness such that hook 233 maintains its shape under traction while the zig zag element 700 is able to elongate using the finger loop 702.

Figure 33:
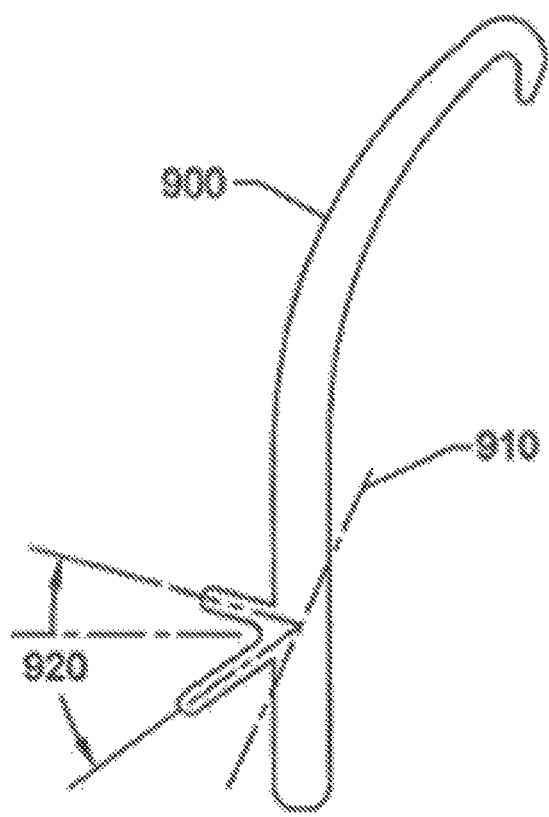
FIG. 33 shows a side perspective view of a handle of a mouth opening device with a "V" grip, according to many embodiments.

FIG. 33 is an illustration of a handle 900 which is provided with "V" grip 920. "V" grip 920 is off axis from 910 and can range from 180 degrees of axis 910 to a minimum of 30 degrees 920 as an example.

Figure 34:
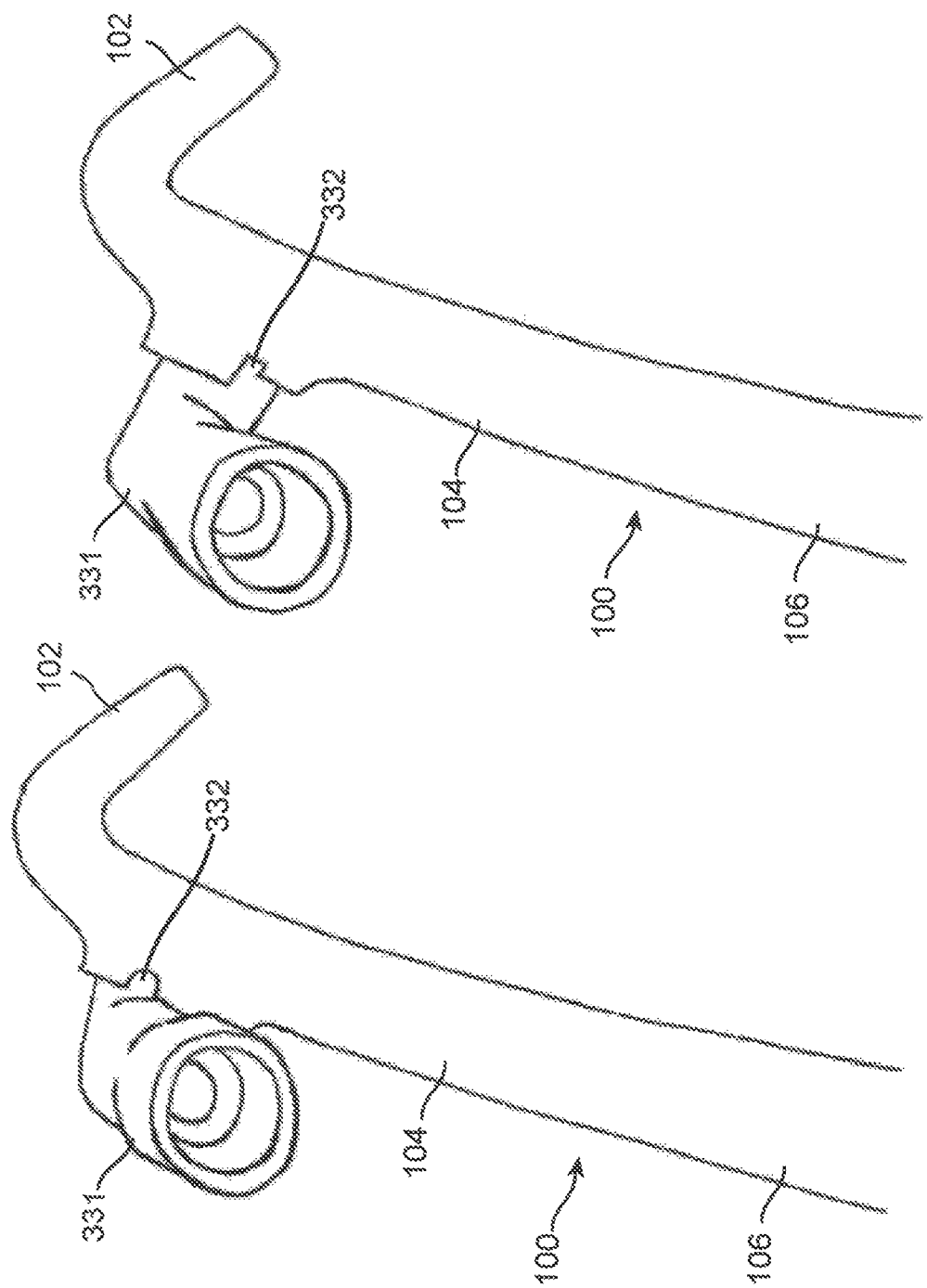
FIGS. 34A and 34B show magnified perspective views of a tooth hook end of a mouth opening device with a swivel mechanism for its suction port, according to many embodiments.

Referring again to FIGS. 17A-17B and 18, a device as disclosed herein may comprise a suction tube exiting from either the right or left side, or both sides, of the distal aspect of the handle of the device proximal to the tooth engaging portion. In some cases, such a configuration may be somewhat inconvenient during use as the dental practitioner may have to remove the device, remove the suction apparatus 200, remove the small caps from the nipple, place the suction apparatus 200 on the contralateral nipple, and place the small caps on the original nipple. To make changing from the right or left side to the other side easier, another embodiment of the device 100 shown in FIGS. 34A and 34B may comprise a swivel mechanism 331 that may be substituted for the elbow fitting in FIG. 18. FIG. 34A shows a shorter swivel mechanism 331 and FIG. 34B shows a taller swivel mechanism 331. The swivel mechanism may allow the elbow connection to rotate 360 degrees, but this may cause the suction apparatus to move about in the mouth and not maintain a selected position. In fact, most swivel configurations would not be stable and would require a detente or certain means 332 or mechanism to stabilize the suction apparatus once it is placed within the mouth. Other means and mechanisms to prevent the movement of the suction apparatus (not shown) once it is placed within the mouth and can be moved by the tongue, lips, dental instruments or even the dental practitioner are anticipated and included herein as potential embodiments. In a preferred embodiment, the rotation may be limited to 180 degrees or less and more preferably 130-160 degrees with the center of this rotational arc being the longitudinal axis of the handle 106 of the device and zero and 360 degrees being neck 104 and tooth engaging member 102. The suction connector is 180 degrees in this example. Hence, in a more preferred embodiment in which the swivel rotates 150 degrees, the swivel may rotate from 105 degrees to 265 degrees of the clock like 360-degree arc. To limit the rotation, a stop mechanism of one of various types on the outer surface of the neck 104 of the device may be employed. Alternatively, a stop mechanism within the swivel mechanism may be employed. By limiting the travel to 150 degrees in this example, the suction apparatus (not shown) is prevented from being displaced while in the mouth as it is prevented from rotating into the upward areas of the arc by the stops on the swivel. In this configuration, the upward pressures exerted by the lower lips tend to force the suction apparatus upward to a point where the stop prevents the suction apparatus from further upward movement. This upward pressure of the lips on the suction apparatus may pin the suction apparatus against the stop and stabilize the suction apparatus, preventing it from moving about when it is placed inside the mouth. The swivel configuration with the stop mechanism allows for the dental practitioner to change the suction apparatus from the right or left side by rotating it from approximately 8 o'clock to approximately 4 o'clock easily while preserving the stability of the device when it is placed at a precise location within the patient's mouth.

While most of the illustrations and the discussion reference a suction apparatus that is directed to only one side, bilateral suction apparatuses may be employed and will be employed in many instances. Other embodiments may utilize a suction that originates from the end of the tooth engaging portion 102 which may be modified to accept a suction tubing 130 as illustrated in FIGS. 34A and 34B.

Figure 35:
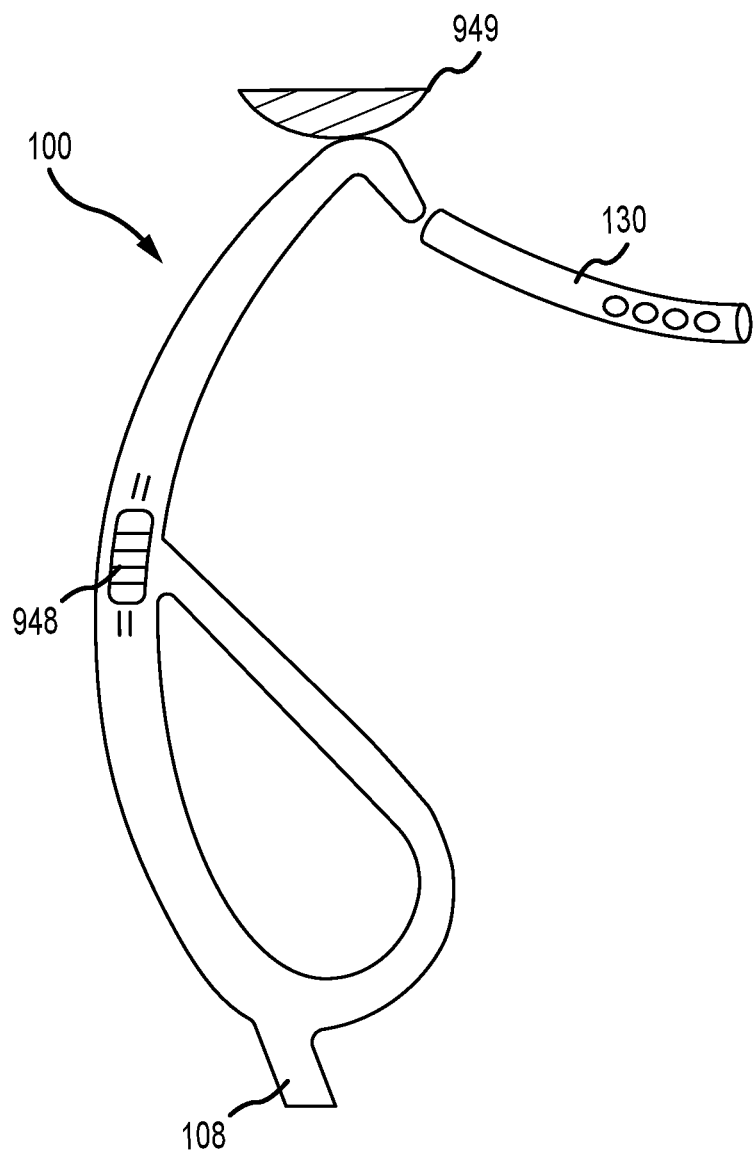
FIG. 35 shows a side perspective view of a mouth opening device with a mist collector, according to many embodiments.

Frequently, with ultrasonic scaling and the use of copious amounts of water in the process, there is a large amount of water that collects in the posterior mouth and the foregoing embodiments coupled with suction may be very advantageous in removing this water. As well, there frequently is a large amount of splatter of water as it is sprayed onto the teeth. The splatter of droplets and mist is problematic as it escapes the oral cavity and wets the patient and hygienist as well as the surrounding environment. Another embodiment of the device previously described which distracts the jaw downward while providing suction may solve both problems, collection of water in the mouth and the spray and splatter of ricocheting water off the teeth, within the same device and it is illustrated in FIG. 35. Co-pending U.S. patent application Ser. No. 14/504,518, which is incorporated herein by reference, demonstrates a fluid suction tube extending into the posterior aspect of the mouth. A cup-like mist or splatter collector may be added to the devices shown and described with respect to FIGS. 10 and 13 of that application, along with a more or less straight perforated suction tube 130 with a controlling mechanism that will allow the patient to control the suction from either the suction tube or the mist collector. In FIG. 35, an improved embodiment may comprise a traction device 100 with suction tubing means 130 with distal perforations, a suction connector 108 on the opposite end, and a mist collector 949, which may be shaped like a shallow cup. The suction tubing 130 means may measure 2-8 mm in length, but optimally 6 mm, comprise an outer diameter of 1/16 inch-1/2 inch but optimally around 3/8 inch, and have a durometer of 40-60, but optimally around 60. The holes may be from one to 20, but optimally around 8 and they may be oriented in opposing pairs. The holes optimally have a diameter of 2.5 mm, but may range from 1 mm to 4 mm. The embodiment may preferentially be connected to the HYE suction commonly present in dental offices, although it may be connected to standard low volume suction.

While a free connection to both the fluid collector tubing 130 and the mist collector 949 may be feasible, a means may be present for directing the suction to one or the other to enhance the suction or vacuum. A slidable mechanism 948 or some other mechanism may direct the suction to either the suction tubing 130 or the funnel shaped mist collector 949.

The slidable mechanism 948 may be activated with the patient's thumb or other digits. The slidable mechanism 948 may default suction to the mist collector 949 by a spring or other mechanism (not shown) when not engaged by the patient providing suction to the mist collector 949 until fluid evacuation is needed via the suction tubing 130. Hence, when the patient needs to evacuate fluid from the mouth, they may do so by a simple movement of the slidable mechanism 948 to direct suction toward the suction tubing means 130 and away from the mist collector 949. Upon removing fluid from the mouth, the patient may release the slidable mechanism 948 and the suction may then be directed to the mist collector 949. The slidable mechanism 948 may be located at any point along the shaft of the traction device 100 to be more ergonomic. Alternatively, when mist collection is not as important when cleaning the posterior teeth, the patient may utilize the fluid collector tubing 130 more than the mist collector 949.

The mist collector 949 is typically cup shaped to enhance collection of the mist but may take any one of other shapes. It may tilt in one or more planes with manual pressure or electronically so to be directed to the area of maximum spray, mist or splatter. Hence, this embodiment solves a lot of problems associated with ultrasonic scaling dental hygiene procedures by providing downward traction on the mandible and relaxing the muscles creating a comfortable atmosphere for the patient, a wider opening for the dental practitioner, fluid evacuation from the posterior mouth, spray and splatter collection preventing unwanted moisture outside the mouth, as well as involving the patient in the process which is psychologically important. Both the patient and the hygienist benefit.

Figure 36:
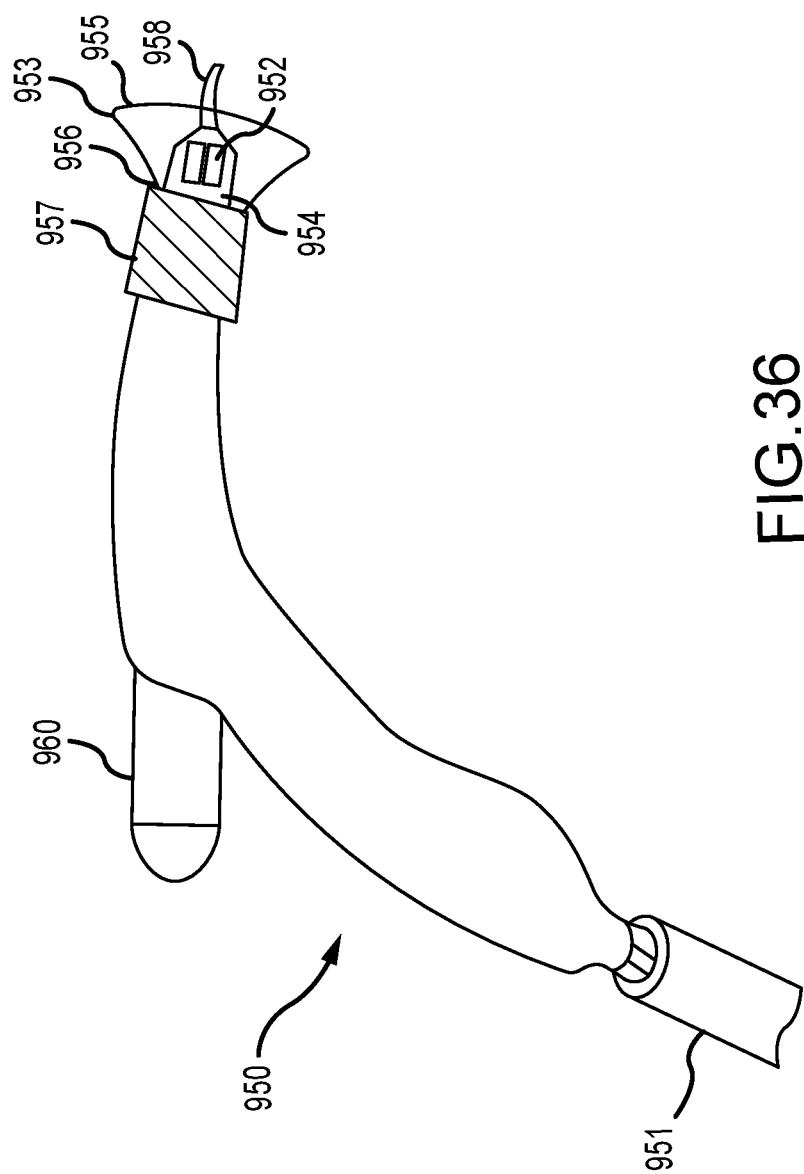
FIG. 36 shows a side perspective view of an ultrasonic scaler hand piece with a mist collector, according to many embodiments.

FIG. 36 illustrates a modification of an ultrasonic scaler hand piece 950 which in currently available scalers comprises at least one of a pressurized air and pressurized water supply. There also may be the option of adding additional materials to clean and polish the teeth to the fluid to a container 960 attached to the hand piece 950. The presence of both pressurized air and water exacerbates the splatter/spray phenomenon when cleaning the teeth. Even pressurized water alone causes significant spray or splatter. Hence, the dental hygienist must use separate devices to attempt to control the fluid which collects in the posterior oral cavity and to attempt to control the spray/splatter, while holding the ultrasonic scaler hand piece to clean the teeth. Since the hygienist only has two hands and needs three devices, this is frequently problematic, especially since the current fluid evacuator devices do not adequately remove the fluid and the suction apparatus used to control the spray/splatter only functions marginally. There is a needed improvement in the design of the current scaler hand pieces which are very efficient at cleaning but cause unwanted problems of fluid and spray/splatter control.

Some current ultrasonic scalers are connected to pressurized air or pressurized fluid or both via a tubing 951 which may be attached to the hand piece 950. The air and fluid may exit from the same or adjacent tubular openings 958 near the distal aspect of the hand piece 950. The improved embodiment of the current invention also may comprise a separate suction channel (not shown) in addition to either pressurized water or air or both. Apertures or holes 952 in the end of the hand piece 950 will suck the spray/mist caused by the pressurized air and water ricocheting off of the teeth into the suction channel within the hand piece (not shown). The suction channel within the hand piece is connected to a suction hose at the base of the hand piece and may be incorporated into the same hose 951 which contains the pressurized air and water channels.

To enhance the collection of more spray/mist, a funnel apparatus 953 which may be stationary, expandable and collapsible or directional may be attached to the distal aspect 954 of the hand piece. The funnel apparatus 953 may be only funnel like with a larger circumference at the mouth or opening 955 of the apparatus and a smaller circumference at the neck 956 or the point at which the apparatus is connected to the suction channel. Also, it may be a partial funnel like configuration with part of the funnel removed for visibility or other reasons (not shown). For example a half funnel or some other fraction of a funnel shaped apparatus may be utilized and positioned to gather the most reflected spray or splatter. The fractional funnel may also be rotatable around the end of the hand piece to be positioned for optimal suction, optimal visibility of the teeth being cleaned, or optimal access with other instruments or because of anatomy. One embodiment may comprise a nitinol mesh braid with an elastomeric coating, although there are many other fabrics and materials which may be employed. The funnel may be collapsible by one of several means. One means is a tubular member 957 which slides over the funnel 953 thereby collapsing the funnel 953 for improved access to posterior teeth or visibility or both. If the tubular member 957 covers the funnel 953, it will be collapsed in a tubular configuration. Retracting the tubular member 957 will allow the funnel 953 to expand into the useful funnel shape as illustrated in FIG. 36. An attachment (not shown) to the tubular member 957 may facilitate the movement of it to collapse and expand the funnel so that it may be partially expanded in a number of positions or completely expanded or completely collapsed. The funnel 953 may be from ¼ inch to 4 inches long, have a diameter at the mouth 955 of ½ inch to 4 inches. Alternatively the housing of the hand piece 950 may actually serve as the tubular member 957 to constrain the funnel, and expansion and collapsing of the funnel may be controlled by translating the funnel forward or backward. The funnel may be positioned closer or further away from the distal tip of the hand piece 950 than is illustrated in FIG. 36. An embodiment may include one or more of the features listed herein in different combinations.

There may be a means (not shown) of directing pressurized air, which is already present in the hand piece 950, into the funnel towards the neck 956 of the funnel 953 to enhance the direction of the water droplets or spray into the funnel 953 containing the suction so that the mist and spray is more efficiently removed via a Bernoulli or Venturi effect. The pressurized air directed toward the neck 956 of the funnel 953 will facilitate the flow of the mist/spray into the suction channel within the hand piece, obviating the current situation which tends to saturate the patient and dental hygienist with fluid.

Additionally, a surfactant which diminishes the surface tension of water, and hence creates smaller droplets, may be added to the air or water that is sprayed onto the teeth. This will serve to create lighter weight and smaller droplets that are more easily aspirated or sucked from the oral cavity as the lighter weight will prevent the smaller droplets from travelling as far. The combination of the funnel to collect the spray, the surfactant to cause the spray to be collected easier, and the suction to remove the spray will be more effective than any one method alone. Furthermore, by utilizing the jaw retraction device previously described in FIG. 35 with the device shown and described in reference to FIG. 36, the fluid which collects in the posterior oral cavity and the reflected spray/splatter may both be controlled much better than is done currently.

The improvements disclosed herein may be implemented with the devices described herein or with other suction devices that are commercially available including the Isolite, IsoDry, IsoVac, Mr. Thirsty, eBite, Miracle Suction, standard dental suction devices and the like. The subsequent improvements may be implemented with the embodiments of the current invention described herein or with other commercially available devices. Many of these latter devices combine suction with a bite prop that fits between the posterior teeth and a means of displacing the tongue and/or cheek away from the area to be treated. While somewhat efficient at removing fluid, they are not directed toward reducing the deflected water and resultant spray or splatter. Improving these devices and others by placing a means to collect the spray, which may be similar to the means described herein, on these devices may improve their function. The preceding discussion is directed toward improvements of a specific device, but they also may be applied to the class of devices that serve to remove fluid from the mouth. The means to improve suction of spray on these devices may consist of a shallow somewhat cupped shaped device that serves as a mist collector and may be connected to the suction channel within the device. As with the description herein of FIG. 35, there also may be a manual or electronic mechanism which regulates the amount of suction directed to either the existing intraoral suction apparatus or to the mist collector (not shown). If the mechanism is electronic, it may comprise a sensor that directs suction preferentially to the mist collector when there is little or no fluid flowing through the standard intraoral fluid collection apparatus, but when significant fluid is present through the standard intraoral fluid collector system, more suction is directed toward it. Alternatively, the suction directed toward the mist collector may be synchronized with the air and water spray of the ultrasonic scaler hand piece. In other words, the mist collector suction may be operable only when the hand piece is activated for cleaning purposes, including set times before and after the hand piece activation, and essentially only when there is spray to collect. This time may vary from one tenth of a second to ten seconds, although the suction preferentially would begin ½ second beforehand piece activation and three seconds after hand piece activation. The mechanism may be all or none or partial, i.e., directing all of the suction toward the intraoral apparatus or the mist collector, or directing only a portion of the suction toward the intraoral apparatus and another portion of the suction to the mist collector and it may be variable between the two suction apparatuses.

As well, the improvements may comprise adding a positive air pressure means to these isolation/suction devices to achieve one or more of facilitating the suction by creating a Bernoulli/Venturi effect and enhancing suction, or to dry the air to enhance evaporation of the spray. The means to provide positive air pressure may consist of a separate tube which may be added to or incorporated within the suction tubing of this class of suction devices and controlled by means known in the industry. Specially fabricated connectors to connect both the suction and positive air pressure channels to the respective suction/vacuum and pressure sources within a dental office may be utilized. The air may preferentially be directed toward the neck or bottom of the cup like or funnel like mist collector to direct moisture laden air into the suction channel connected to the mist collector. Channels that direct the positive air pressure to points near the free end of the mist collector may be employed so that air may be directed toward the neck of the funnel like shape. As well, the positive air pressure may comprise of a means to subject the air to a desiccant or to warm the air or both which may be incorporated into the improved device or may be a separate attached device.

Figure 37B:
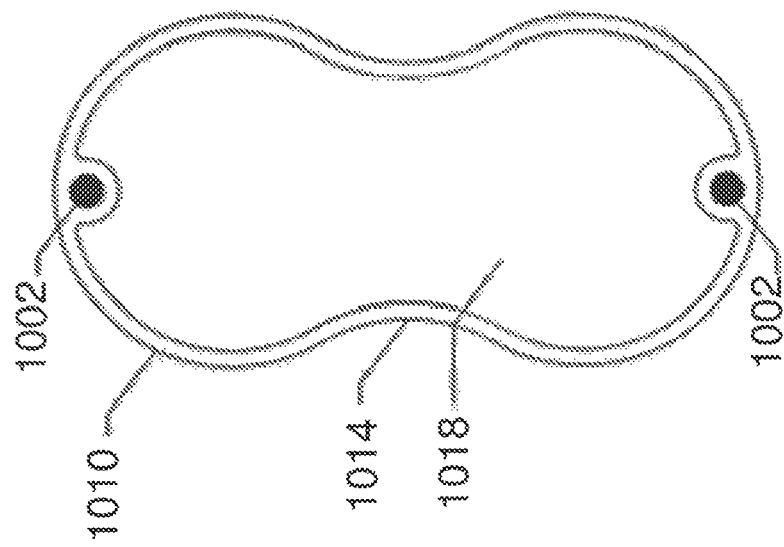
FIG. 37B is a transverse cross-section view of an exemplary embodiment of a suction tube for insertion into the mouth.
Figure 37A:
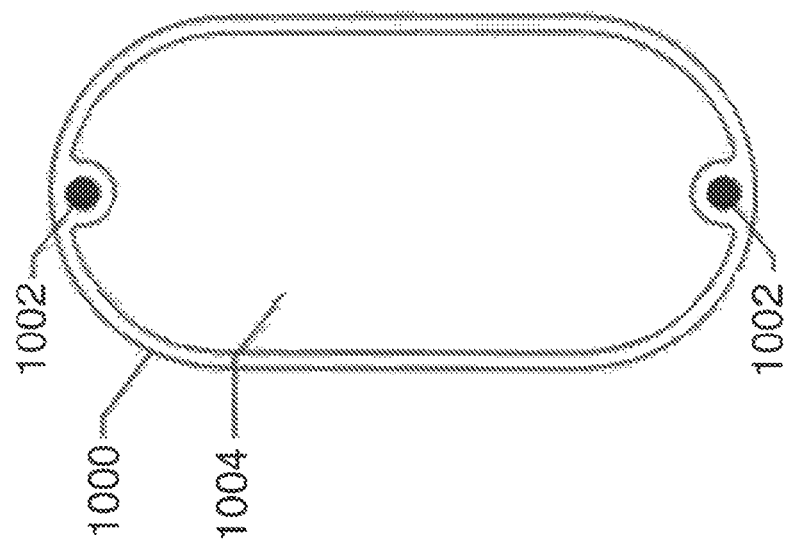
FIG. 37A is a transverse cross-section view of an exemplary embodiment of a suction tube for insertion into the mouth.

FIG. 37A is a transverse cross-section view of an exemplary embodiment of a suction tube for insertion into the mouth, suitable for incorporation with any mouth opening device as described herein. The suction tube 1000 may comprise an oval-shaped cross-section, so as to fit more comfortably between the gum line inside the mouth. The suction tube may further comprise one or more support wires 1002 coupled to the tube. The support wires are malleable and can be bent numerous times so as to allow for adjustments as needed during the oral procedure. Any number of support wires may be provided with the suction tube, and the support wires may be coupled to the tube using any appropriate method. For example, as shown in FIG. 37A, the suction tube may comprise two support wires capture-molded within the tubing material, at opposing ends along the major longitudinal axis 1006 of the oval-shaped cross-section (e.g., at 12 o'clock position and 6 o'clock position as shown). The capture-molding of the support wires within the tubing material can allow for a clear aspiration lumen 1004.

FIG. 37B is a transverse cross-section view of an exemplary embodiment of a suction tube for insertion into the mouth, suitable for incorporation with any mouth opening device as described herein. The suction tube 1010 may comprise a generally oval-shaped cross-section with a waist section 1014, the waist section having a width 1015 that is smaller than the maximum width 1011 of the cross-section. The suction tube may further comprise one or more support wires 1002 substantially similar to the support wires described in reference to the embodiment of FIG. 37A For example, the support wires may be provided at opposite ends along the major longitudinal axis 1016 of the substantially oval-shaped cross-section, and the support wires may be capture-molded within the tubing material so as to not impede flow through aspiration lumen 1018. The support wires may be malleable and capable of being bent numerous times to allow for adjustments as necessary.

FIG. 38 is a transverse cross-section view of an exemplary embodiment of a multi-lumen suction tube, suitable for incorporation with any mouth opening device as described herein. The suction tube 1030 may comprise one or more support wires 1002 as described herein, extending axially throughout the length of the suction tube. The suction tube may comprise a plurality of separate lumens 1032 extending axially through the length of the suction tube. The one or more support wires may be capture-molded within the tubing material, such that each of the plurality of lumens remains unobstructed by the support wires. While the embodiment of FIG. 38 shows the suction tube 1030 having a substantially circular cross-section with a single support wire disposed at the center of the circular cross-section, suction tube may have any cross-sectional shape, and may comprise any number of support wires disposed at any appropriate location(s) within the tube. Similarly, while the embodiment of FIG. 38 shows four lumens 1032 of equal shape and size distributed radially symmetrically about the longitudinal axis of the suction tube, the suction tube may comprise any number of lumens having any shape, size, or distribution within the suction tube.

FIG. 39A is a transverse cross-section view of another exemplary embodiment of a suction tube, suitable for incorporation with any mouth opening device as described herein. The suction tube 1040a may have a substantially circular cross-sectional shape. The suction tube may further comprise one or more support wires 1002 as described herein, capable of being bent numerous times to allow for adjustment. For example, the suction tube may comprise two support wires 1002, disposed at opposite ends across the diameter of the suction tube. The support wires may be capture-molded within the tubing material to allow for a clear suction tube lumen 1042a.

FIG. 39B is a transverse cross-section view of another exemplary embodiment of a suction tube, suitable for incorporation with any mouth opening device as described herein. The suction tube 1040b is similar in many aspects to suction tube 1040a shown in FIG. 39A, except the suction tube 1040b comprises four support wires 1002. The support wires are capture-molded in the tubing material so as to allow for a clear flow through the aspiration lumen 1042b. In this exemplary embodiment four support wires are distributed in a radially symmetric manner about the circumference of the tube, such that each support wire is radially offset by 90° with respect to an adjacent support wire. Such a configuration allows for bending of the suction tube in all planes. The configuration of FIG. 39B is shown by way of example only, and the suction tube may incorporate a smaller or greater number of support wires distributed in any manner within the suction tube.

When the security threat is identified, the method 700 may proceed to step 751. At step 751, the security operation platform may generate a report based on the identified threat. Such a report may comprise the information included in the updated incident identifier. The report may in some embodiments comprise next steps to be taken by a security analyst, the affect user, or other entities. The report may be presented via a UI to a security analyst, or the affected user, or may be saved as a file on a network location. After generating a report, at step 754, the security operation platform may end.

Figure 40A:
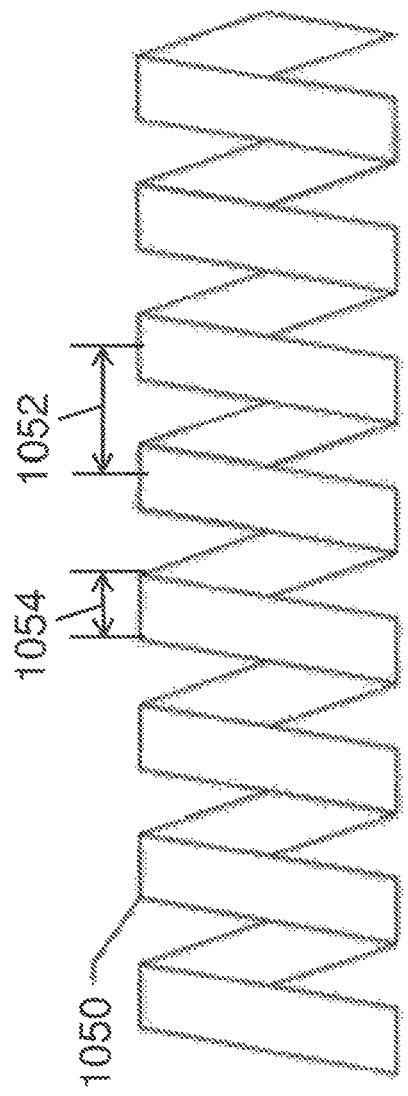
FIG. 40A shows an exemplary embodiment of a helical ribbon of a suction tube.

FIG. 40A shows an exemplary embodiment of a helical ribbon of a suction tube, suitable for incorporation with any mouth opening device as described herein. The helical ribbon 1050 may be disposed about the periphery of a suction tube, for example capture-molded within the tubing material, coupled to the internal surface of the tube facing the lumen, or coupled to an external surface of the tube. The helical ribbon may comprise a malleable wire configured to have a spring-type shape, for example. The helical ribbon may have a tight or elongated pitch 1052 as desired or necessary. For example, the helical ribbon may be configured to have pitch that is long enough to prevent stacking of the winds when the ribbon is bent at an acute angle. A relatively elongated pitch may have the advantage of allowing for a greater sweep of the suction tube or a more acute bend angle. The width 1054 of the helical ribbon may also be adjusted to control the range of motion of the suction tube. A relatively narrower ribbon may allow for a greater bending range due to reduced stacking on the winds during bending, while a relatively wider ribbon may result in quicker stacking of the winds during bending and thereby achieve less acute bending angles.

Figure 40B:
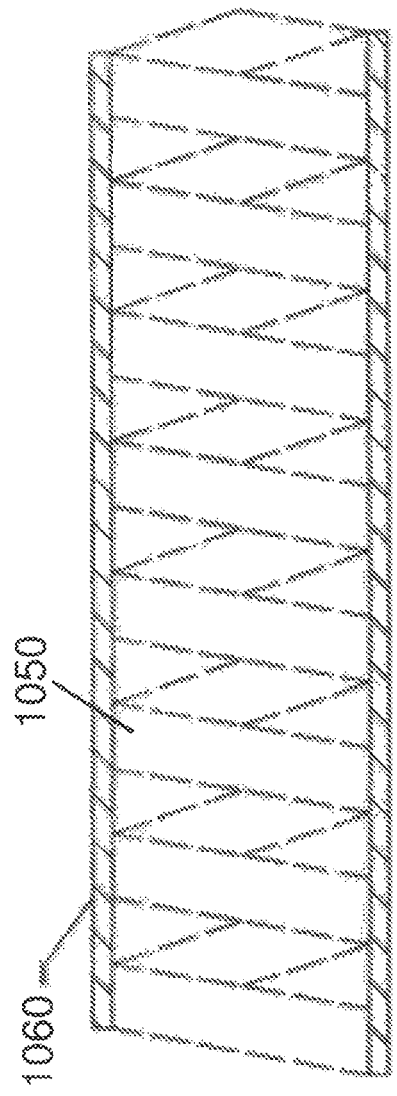
FIG. 40B shows an exemplary embodiment of suction tube comprising a helical ribbon.

FIG. 40B shows an exemplary embodiment of suction tube comprising a helical ribbon, suitable for incorporation with any mouth opening device as described herein. The suction tube 1060 comprises an integrated helical ribbon 1050, which may be similar in many aspects to the helical ribbon 1050 shown in FIG. 40A. In this embodiment, the helical ribbon is capture-molded within the tubing material such that the aspiration lumen remains clear. The helical ribbon may comprise a malleable material that is capable of bending numerous times to allow for adjustment as needed during the procedure.

Figure 41:
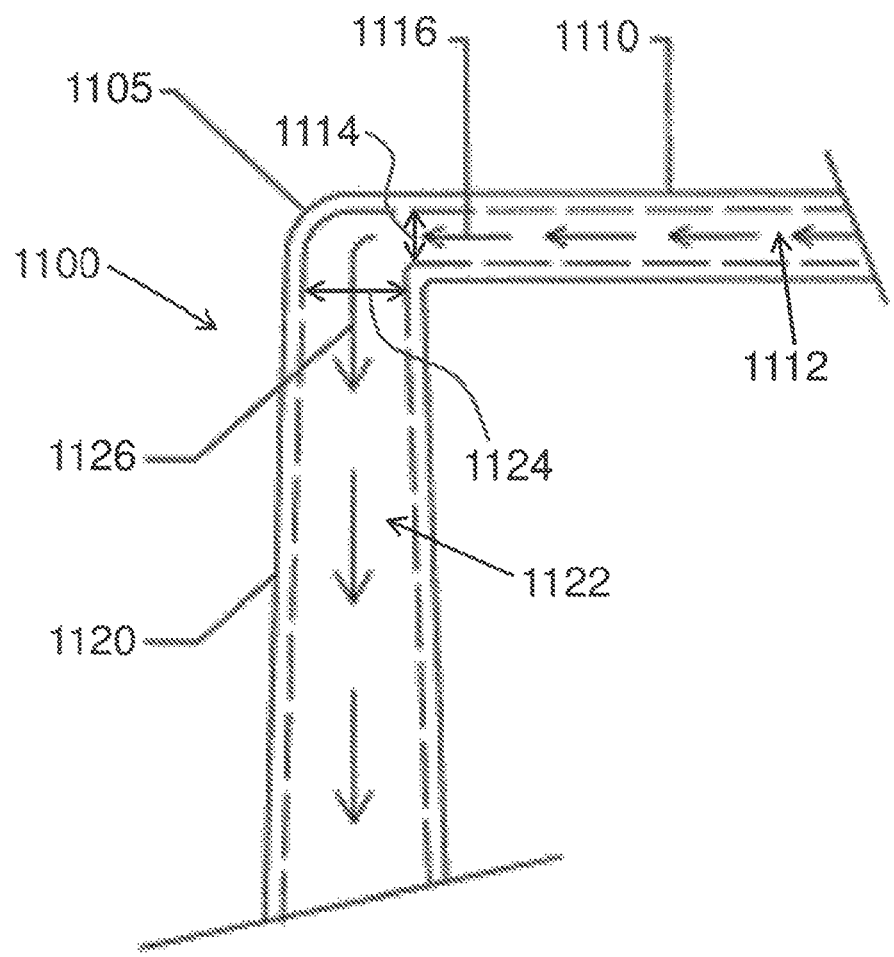
FIG. 41 is a schematic illustration of an exemplary embodiment of a suction tube.

FIG. 41 is a schematic illustration of an exemplary embodiment of a suction tube suitable for incorporation with any mouth opening device as described herein. The suction tube 1100 comprises a mouth suction tube 1110 for insertion into the mouth and a main suction tube 1120. The mouth suction tube and the main suction tube may be separate components coupled together at the juncture 1105, or they may be different portions of a single, integrated suction tube, wherein the mouth suction tube portion transitions into the main suction tube portion at juncture 1105. The mouth suction tube may have a first aspiration lumen 1112 with a first internal diameter 1114, and the main suction tube 1110 may have a second aspiration lumen 1122 with a second internal diameter 1124, wherein the first and second aspiration lumens are fluidly coupled at the juncture 1105. Each of the first and second internal diameters of the aspiration lumens may vary over the length of the suction tubes, as shown in FIG. 41 for the second aspiration lumen of the main suction tube, whose internal diameter increases along the length of the main suction tube in the direction of flow of the aspirate. In preferred embodiments, at the juncture 1105, the internal diameter 1114 of the first aspiration lumen 1112 is smaller than the internal diameter 1124 of the second aspiration lumen 1122, as shown in FIG. 41. The difference in the internal diameters of the lumens can lead to differences in the aspiration rates through the two aspiration lumens, with the first aspiration rate 1116 through the first aspiration lumen 1112 greater than the second aspiration rate 1126 through the second aspiration lumen 1122. The correlation between the aspiration lumen diameters and the aspiration rates can be summarized by the following equation:

$$D1 < D2, \text{ therefore } V1 > V2$$

wherein D1 is the internal diameter 1114 of the mouth suction tube lumen at the juncture 1105, D2 is the second aspiration lumen diameter 1124 of the main suction tube lumen at the juncture, V1 is the first aspiration rate 1116 through the mouth suction tube, and V2 is the second aspiration rate 1126 through the main suction tube.

All of the physical components of suction and the actions described herein, including but not limited to suction and positive air pressure, may be synchronized or activated with the scaler or other dental hand piece, may be activated by a foot pedal or the like, may be activated by manual activation by the patient or dental practitioner, or controlled by a like means.

The suction inlets in all of the examples herein may be directly connected to the suction channel which extends through the suction connector and is continuous with the suction channel of the suction valve. As well, any one feature may be combined with any other feature described herein, and the specific features mentioned should not be limited to a specific embodiment or species.

The devices described herein comprise different components and various configurations of these different components. The single or multiple configurations of the separate components may be combined with any single or multiple configuration of another component or components that may result in a device not explicitly described herein. By providing this flexibility in the structural configuration of various devices, the goals of providing the dental practitioner with greater exposure and convenience and the patient with greater comfort can be achieved.

Figure 42:
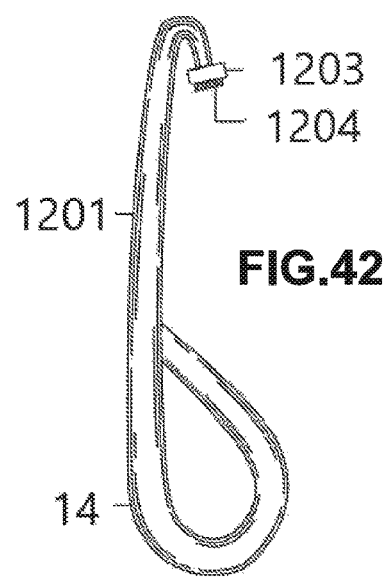
FIG. 42 shows a side view of the device of the invention.
Figure 44:
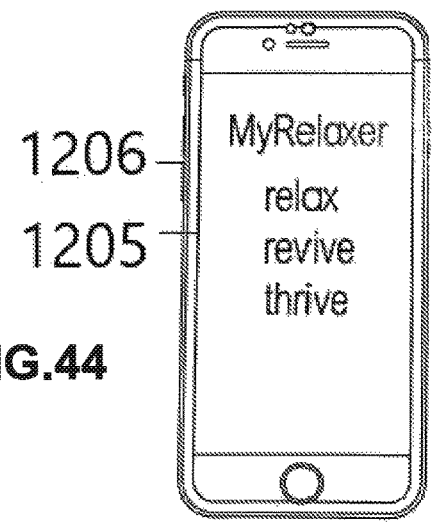
FIG. 44 shows a front view of the software app.
Figure 43:
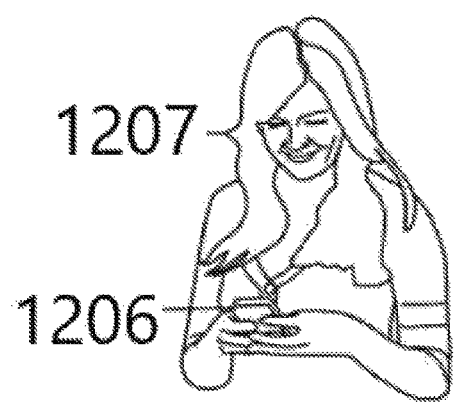
FIG. 43 shows a perspective view of the invention app being operated.
Figure 45:
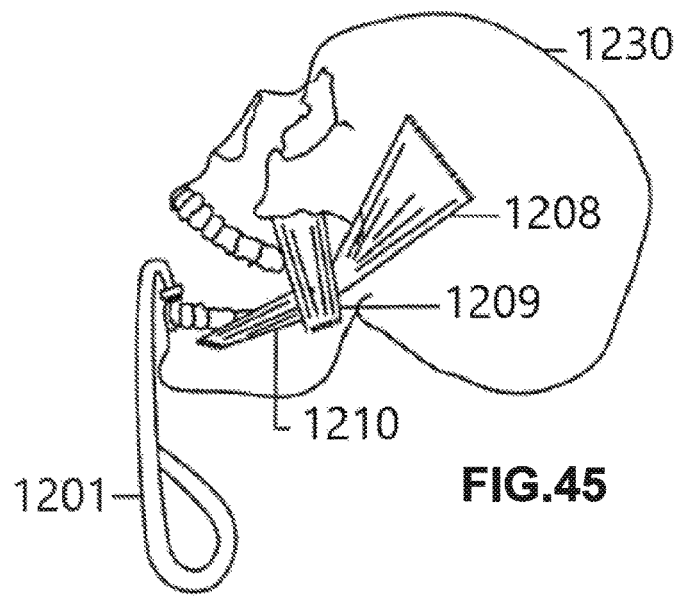
FIG. 45 shows a side view of the device with intended use position in relation to a human skull and muscles of mastication.

FIG. 42 shows a side view of the invention with the relaxation device 1201 having a 'b' shape made of a slightly flexible yet rigid material such as but not limited to plastic, rubber, metal, and the like. One distal end having a loop shaped handle 14 and another distal end having a hook shape with a more or less rectangular-shaped tooth engaging component 1203 having a multitude of bristles 1204 configured perpendicular to said tooth engaging component 1203. FIG. 43 shows a perspective of user 1207 interacting with smartphone 1206 and FIG. 44 shows a front view of the software app 1205. Said invention software app 1205 being written from code that may include, but not be limited to: Java, C++™, Visual Basic™, Linux™, Basic™ and the like. The software also compatible with a plurality of operating systems such as, but not limited to: Windows™, Apple™, and Android™, and compatible with a multitude of hardware platforms such as, but not limited to: personal desktops, laptops, tablets, smartphones and the like. FIG. 45 shows a side view of the device 1201 inserted on a cranium 1230 jaw and stretching Masseter muscle 1209, Buccinator muscle (facial expression muscle) 1210, and Temporalis muscle 1208. Other muscles of mastication include the medial and lateral pterygoid muscles and the suprahyoid group of muscles (digastric, stylohyoid, mylohyoid, geniohyoid muscles) and the infrahyoid muscles (sternohyoid, thyrohyoid, and omohyoid muscles).

The act of smiling takes more energy (calories) than frowning. Relaxing the Buccinator muscle 1210 (and other muscles of facial expression) is of importance as relaxing the muscles of facial expression will make it easier to smile. Smiling generates parasympathetic activation which will relax the subject overall. An object of this invention is to generate parasympathetic activation by relaxing not only the muscles of mastication, but also the muscles of facial expression. This is a key ingredient of the invention.

Additionally, use of the current device, maneuver, system and method will relax the individual creating an environment wherein it will be easier for the individual to smile. It is difficult to smile when one is stressed and reactive, hence relaxing the individual by engaging the parasympathetic nervous system with the maneuver and system will encourage a response to a stimulus, person, or event that is accepting rather than reactive and more likely resulting in a smile. Since a smile is one's most attractive and engaging physical attribute, one or more of the device, maneuver, method and system will contribute to the users physical appearance and beauty more so than make up and other beauty or anti-aging products. This is another goal of the invention: to improve the physical appearance of the user by engaging the parasympathetic nervous system to relax them, to relax the muscles of facial expression, and to relax them emotionally to promote smiling as a response to a stimulus, person or event.

Figure 46:
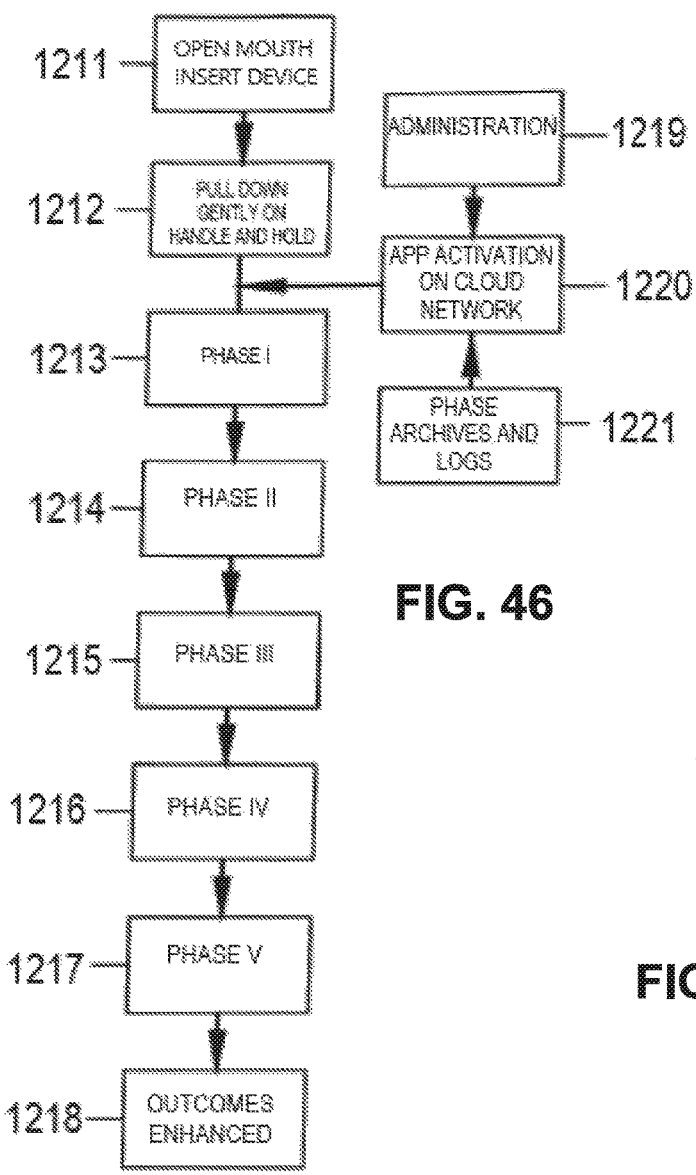
FIG. 46 shows a representative view of an example of the invention process.

FIG. 46 shows a representative view of a process according to one embodiment of the present disclosure with a user opening their mouth 1211 and inserting relaxation device 1201 onto the tops of their central and lateral incisors and gently pulling down on the handle 1212. In certain embodiments, the jaw stretching relaxation device comprises a handle to be engaged with the user's hand or fingers, a more or less soft tooth piece that engages the top of the lower teeth or the insides of the laterally placed right or left lower teeth and a connecting portion between the handle and the tooth engaging piece. The method of using the jaw stretching device to achieve parasympathetic activation and subsequent relaxation includes placing the tip of the device over the lower front teeth and pulling the handle of the device downward until a gentle stretch is felt. This downward traction is then maintained for a period of several seconds to minutes, typically from 30 to 60 seconds. Subsequently, a stretch to one side or the other is optionally performed, followed by downward stretches or any combination of downward and sideways stretches. However, in at least some embodiments, it is the downward stretch which actually causes the relaxation, and only downward stretches are employed to relax a stressed individual and promote parasympathetic activation. There is a difference in stretching the jaw muscles to relax the jaw muscles and relieve the tension in the jaw area and the stretching the jaw muscles to achieve psychological relaxation. It is the latter effect that the device, method, maneuver, and system of the current invention produces, not just the tension relief from physically stretching the jaw muscles.

Another method of using the jaw stretching device to achieve parasympathetic activation involves downward stretches combined with measured breathing while the stretching is being accomplished. This involves slowly breathing in for approximately 5 seconds, pausing, slowly breathing out for approximately 6 seconds and pausing. Three to four measured breaths while stretching is preferably performed, although from one to 60 or more may be employed by this method. Measured breathing has been documented in the literature to relax individuals.

Still another method of utilizing the jaw stretching device to achieve parasympathetic activation involves added guided meditation, inspirational messages, music, sounds, aromas, or ingestion or inhalation of relaxation inducing substances during or immediately prior to the stretching sessions amongst other additions. In some embodiments, the guided meditations and other content, such as guided stretching sessions, provided during or immediately prior to the stretching session are provided digitally on the website, as a web app, or as a smartphone app amongst other means.

In certain embodiments, a reminder can be provided for the user to perform either the stretching relaxation session, the guided meditation or other content, to record their emotions/feelings/mood or the like at that time, and to track progress of using the device of the current invention, the ancillary programs, and improvement in stress, symptomatology, and the like. This reminder comprises recording these parameters in a conventional notebook or via a digital application connected to a smartphone or computer. The user then activates the app connected to a cloud network 1220 or alternative means having operations such as but not limited to administrative functions 1219 (subscriptions, user demographics, payments etc.) and phase archives and logs 1221 that keep records of user experiences therein. In further embodiments, the user is provided with tips and advice on how to review these archives and logs to further improve their experience. In still further embodiments, the system may adjust the program based on the user input to improve the user input. In other embodiments, the cloud network may also transmit guided meditation programs or soothing sounds to the user's device.

FIG. 46 also shows the five phases a user will go through while being guided by software app 1205. An object of the current invention is to utilize one or more of these phases together or with other maneuvers not included herein to control stress by relaxing the subject with the device, method, maneuver, and/or system. Phase I 'Need to Relax Decision to Pursue Personal Change' 1213 guides users in understanding that pain and distress must be overcome or under control before even considering the prospect of improving the basic habits that will cause one to feel better. That is the instant jaw stretching device: to relieve the tension and mental stress that contributes to the physical pain of tension headaches, migraines, and orofacial pain. A second benefit is to relax one so that life becomes a bit more enjoyable while they are acquiring skills to deal with stress and tension and related maladies. Again, since it is impossible to be reactive (to stress) and creative at the same time, one must be relaxed or unstressed in order to have the cognitive wherewithal and decision-making abilities to create their path of improvement. Use of the jaw stretching device to relax and feel better immediately, is necessary so that one is able to choose to pursue a personal change path, and to embark on the path of acquiring feel good skills.

Phase II 'Becoming Stronger via Stress Management Toolkits' 1214 presents thoughts related to improving basic natural habits will provide the solid foundation and the resilience for the body and the mind to respond to challenges. That is the purpose of the Phase II of the system. Again, goal setting techniques and scientifically proven techniques on how to best, most time efficiently, and most simply effect change in these habits will be provided along with practical tips and tricks to accomplish these goals. These will be provided in Toolkits, a stepwise fashion that will also bolster the self-discipline needed to properly address subsequent steps and other challenges in life. Unequivocal evidence documenting the importance of 1) proper sleep, 2) movement, 3) nutrition, 4) positive attitude and gratitude for what one currently has, and 5) knowledge of habit change methods amongst others are provided as part of the System. The instant gratification of feeling better now and tomorrow will be emphasized. The tired, over-used delayed health benefits rationale typically and unsuccessfully employed in numerous diets, exercise programs, etc., will be de-emphasized. Humans just don't respond to warnings of Alzheimer's forty years hence from poor sleep habits or Type II Diabetes in ten years from poor movement and dietary choices. Humans do respond to maneuvers that will provide more or less instant results and improvement in their current painful conditions of daily life. Combining the 1) instant gratification of use with 2) social incentives ("Other people like me with problems similar to mine are doing this to get better") to promote belonging and 3) progress monitoring reports to give the needed feedback further enhances the Stress Management System concept. The System and Method of the instant invention will provide these elements.

Phase III 'Control Over Stress' 1215: Once the mental and physical pain are under control and the good habits have begun to provide a resilience factor to deal with life's stressors, the subject will be provided means to accumulate more skills and techniques to prevent backsliding to the "Old Way" of living AND to propel one to the next step. Intriguing insights into how and why we do the things we do, time affluence, happiness, motivation, digital use minimization, how to achieve any (practical) goal and on and on and on. This is the purpose of subsequent content articles, articles, blog posts, etc. on relieving tension, stress, and pain and beginning to thrive in all areas.

One may visualize this phase as a consolidation phase before further growth. In some embodiments, this phase comprises a series of lessons delivered by email or text to the subjects to maintain engagement in the process. The delivery of this information in a stepwise manner rather than a bulk download of information is a key component of this phase. This also is a time to reflect on the journey so far and the empowerment felt as a result of the successes achieved. And a time to put into practice those insights, tools, habits that were gained in Phases I and II. But it is mainly to prepare one for the path ahead.

Phase IV is titled 'Beyond Stress, Headaches, and Tension 1216. By this time, the distracting stress should be under control and since one is no longer reactive, they become creative and have the ability to create a new path to Well-Being. One realizes that one grand purpose of life is simply being passionately on one's unique path to be better than one's former self, benefiting oneself and the world. Being passionately on that path to improvement is the key to happiness and fulfillment and to flourishing in life. It is a desirable place to be, but stress is so distractive that it will prevent the ability to even recognize that the path even exists. One reaches the level of flourishing when five items are all present and congruent: positive emotion, engagement, meaning, positive relationships, and accomplishment. This phase focuses on optimizing one's life in all five areas. This is the purpose of the Stress Management System Advanced System which comprises inspirational modules of self-awareness, meditation, self-discipline, purpose, and the like that would not be able to be considered by the individual earlier in this journey. Earlier in the journey, the individual would still be struggling and focused on surviving at best.

During Phase V 'Continuing the Journey' 1217 users receive follow-up communications and posts will encourage, inspire, and support the lifelong journey. Additional inspirational material and encouragement are provided to remind and bolster the commitment to being on and staying on the path to optimizing one's life. After all phases are completed a user will move toward their own version of an enhanced outcome 1218.

Figure 47A:
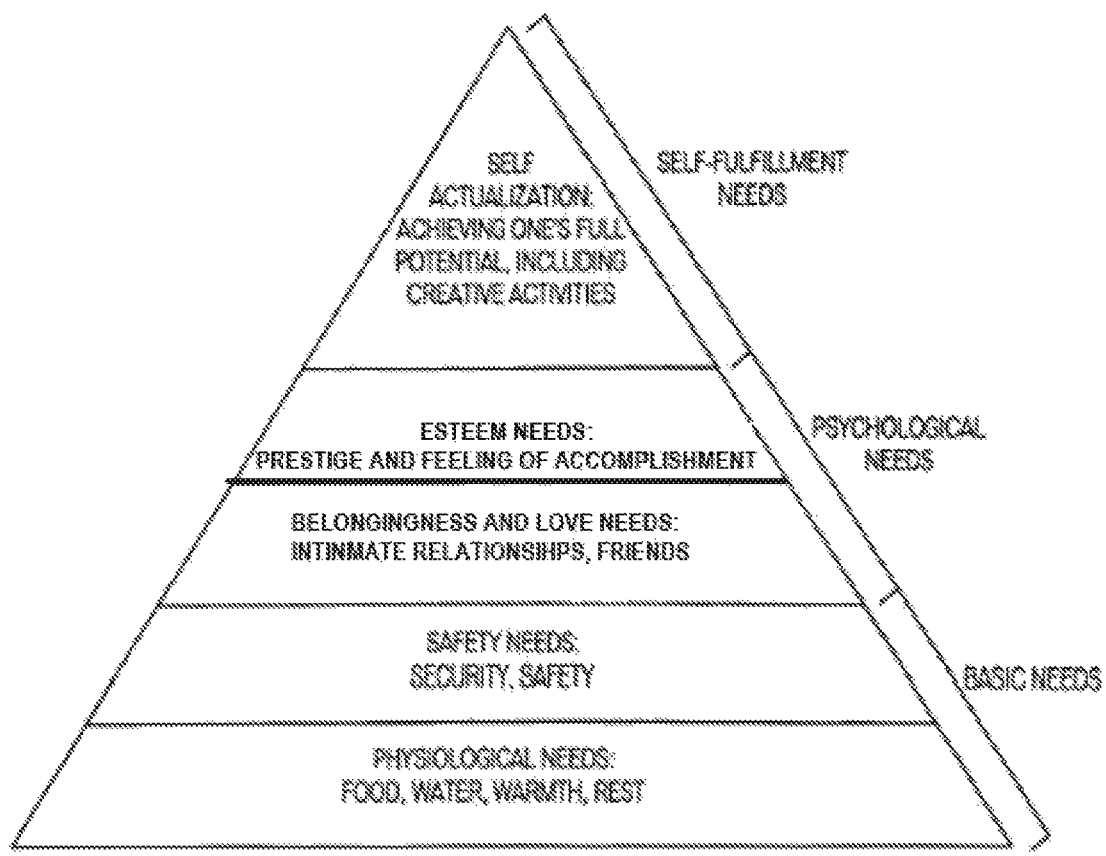
FIG. 47 A demonstrates Maslow's hierarchy of needs triangle.

FIG. 47A demonstrates Maslow's hierarchy of human needs, a classic representation of how the foundational component of basic needs support higher levels of consciousness and existence.

Figure 47B:
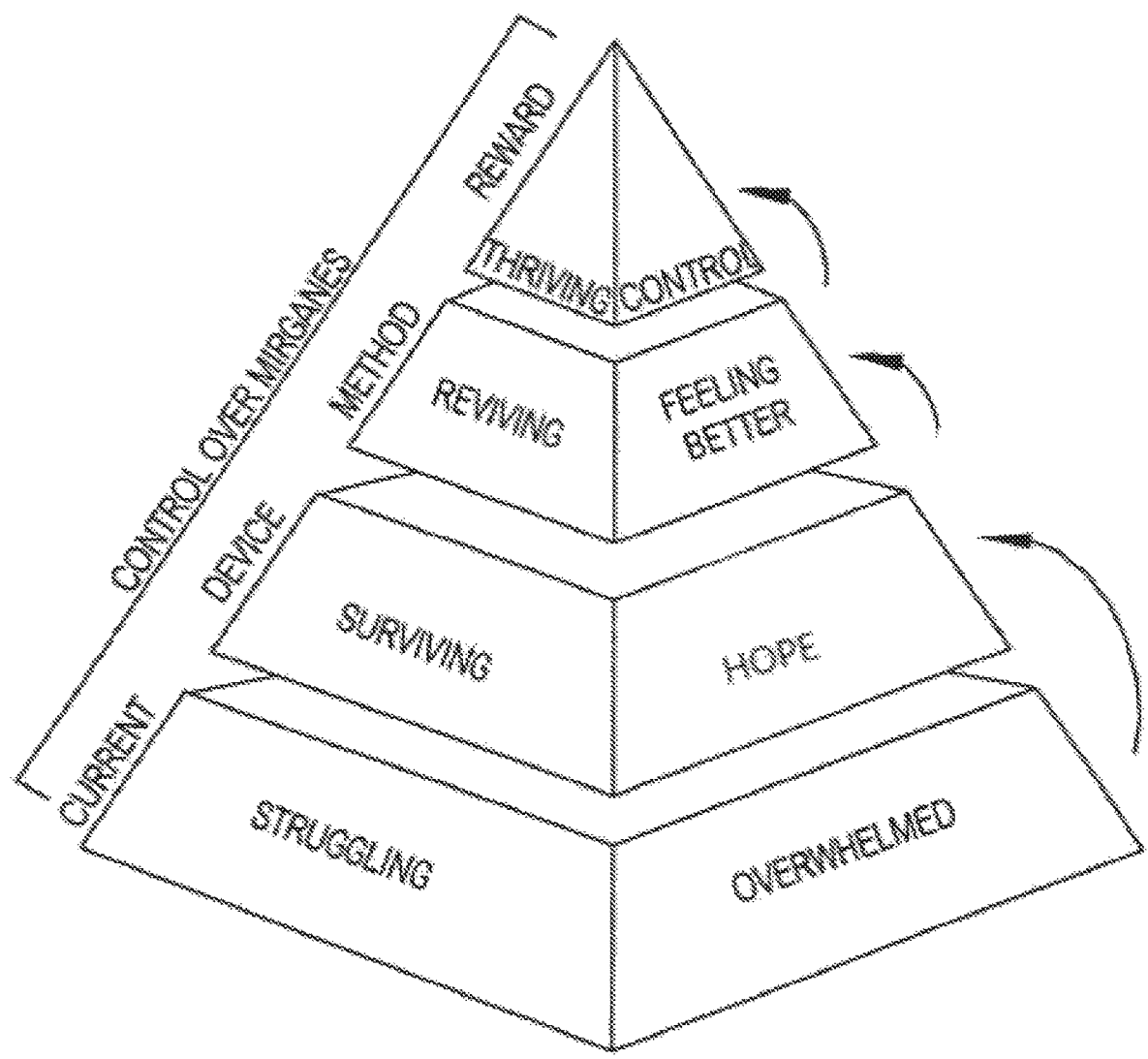

FIG. 47B is and adaptation of Maslow's pyramid and demonstrates the stepwise manner in which the device, method, and system of the current invention propels the subject to a higher level of functioning. In this example, improvement in migraine headaches is indicated, but in other embodiments of the method, this stepwise approach is utilized for any stress related condition including, but not limited to tension headaches, temporomandibular joint conditions, computer neck and other neck pain, insomnia, bruxism, tinnitus, cognitive or learning ability, anxiety, decision making, psychological conditions, PTSD, addictive behaviors, psychological counselling, and the like. In other embodiments, the device, method, and system is used to improve one's voice by relaxing the muscles of phonation and amplitude, tone, timber, and frequencies involved in phonation while speaking or singing. In certain embodiments, the device, method, and system is utilized to improve one's physical appearance by relaxing the muscles of facial expression and engaging the parasympathetic nervous system to relax one physically, mentally and emotionally as a relaxed person is more attractive than a stressed person. Competitive sports will be enhanced in the same manner. Even driving a car is easier when one is relaxed. The above examples are only examples and should not limit the extent nor domain of the use of the current device, method, maneuver, and system which apply to virtually any activity.

Returning to migraines, these headaches are frequently triggered by stressful events, lack of sleep, lack of activity, hormonal changes, caffeine, alcohol, different foods, sensory stimuli, and the weather amongst others. The system of the current invention may also include means and strategies in the form of instruction, motivation, or encouragement to avoid many or all of these migraine triggers in addition to the relaxation jaw stretching device described herein. In some embodiments, educational means are provided to the user, such as content articles, articles, blog posts, lectures, and videos etc. on reducing, preventing, and avoiding the triggers that cause migraines.

Figure 48:
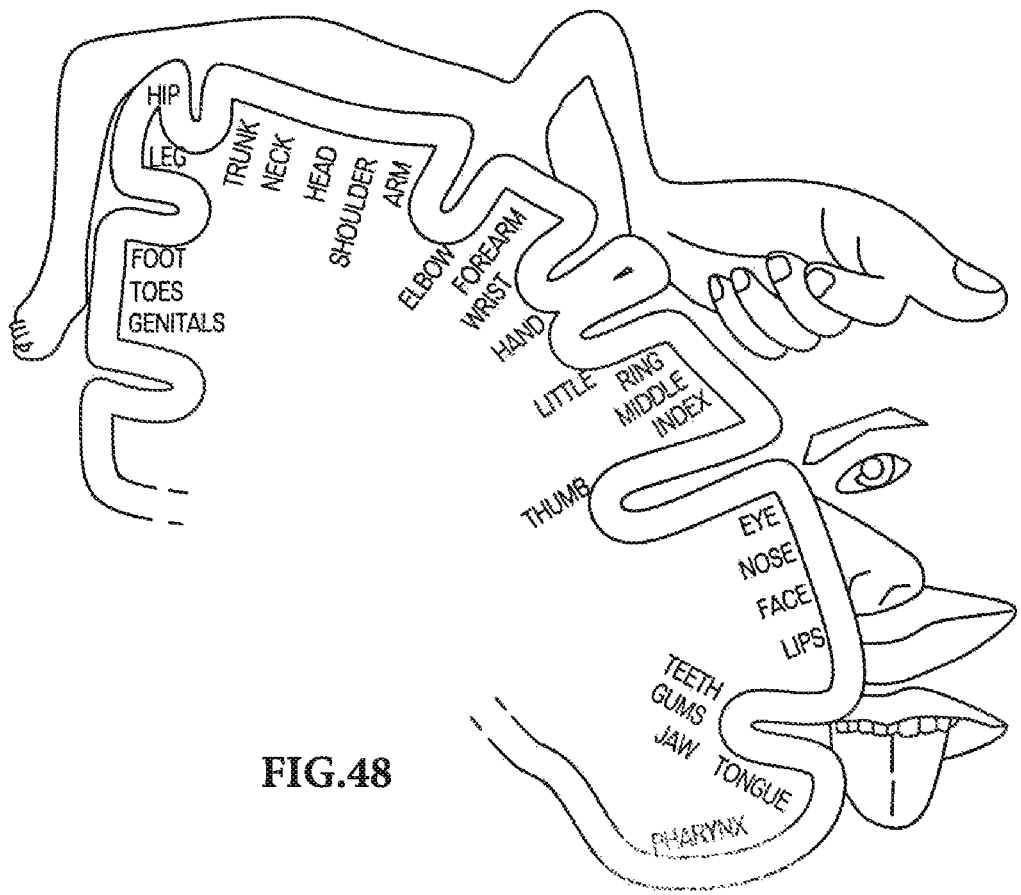
FIG. 48 is an image demonstrating the homunculus concept.

FIG. 48 demonstrates the homunculus concept of the sensory connections of certain body parts within the brain. The hands and facial area dominate. Utilizing a device which employs the hands and the mouth area, as the current invention does, will relax the subject as already described. Humans are wired to utilize these relatively overrepresented areas and that is at least one reason they are overrepresented. Utilizing the hands to hold the relaxation device and placing it in the mouth has a calming effect. Using the device to gently stretch the jaw also has a calming effect.

All of the individual actions mentioned herein may not contribute to the relaxation effort individually to be noticed by the subject, but the collective effect will promote a noticeable and recognizable change from stress to a more relaxed effect. The collective effect of these individual actions is a goal of this invention.

Figure 49:
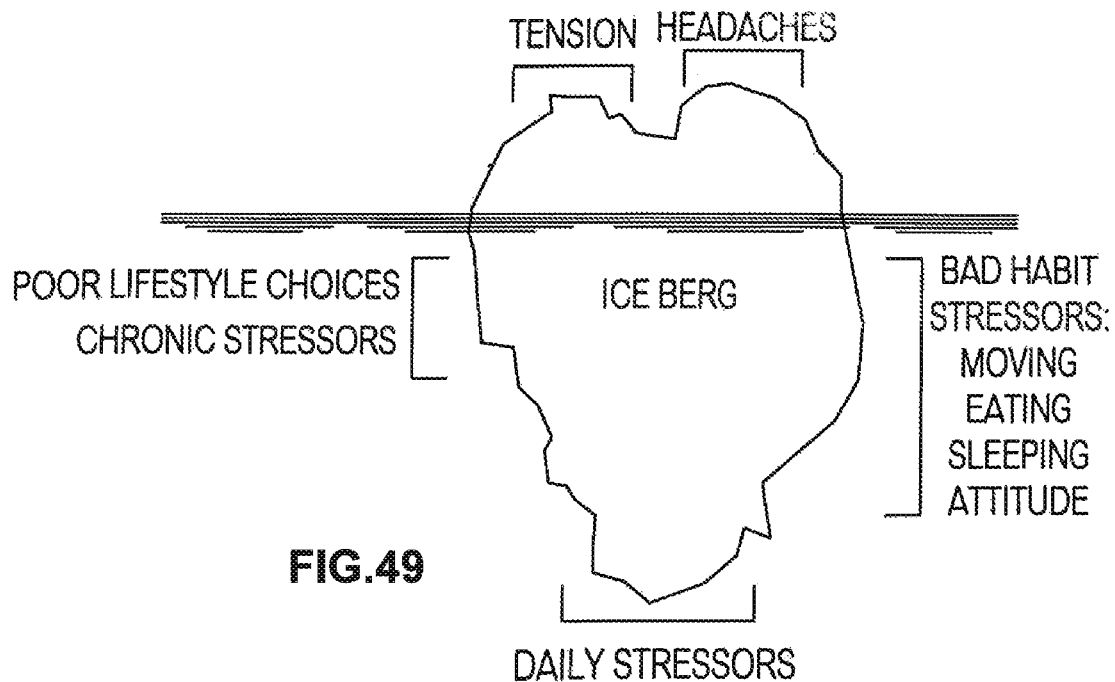
FIG. 49 demonstrates the iceberg concept of stress and recognizable symptoms and the unrecognizable causes.

FIG. 49 demonstrates the iceberg effect of stressors and the symptomatology that is above the surface and noticed by the individual as well as the contributing factors which may not be recognized by the subject below the surface.

In certain embodiments, the current invention comprises one or more of the phases described herein or parts and pieces of the phases in any one of innumerable combinations. The goal is to reduce stress by relaxing the subject. Other embodiments of the invention comprise one or more of utilizing the device, the maneuver, the phases, the app, the lessons, and other adjunctive means (measured breathing, mediation) individually or in some combination to engage and activate the parasympathetic nervous system to promote relaxation.

In further embodiments, one or more of utilizing the device, the maneuver, the methods, the system, the lessons, the app, and the adjunctive means are optionally employed as an adjunct to facilitate the implementation of specific therapies directed towards treating or improving various conditions, including tension headaches, migraine headaches, facial pain, TMJ pain and issues, bruxism, tinnitus, neck pain, learning, decision making, psychological therapies, counselling, addictions, attitude training, beauty enhancement, anti-aging therapies, sports enhancement, vocal and voice improvement, sleep enhancement, insomnia, performance of physical activities, concentration enhancement, focus training, motivational, meditation enhancement, yoga enhancement, as well as enhancement of other relaxation or stress reducing techniques and methods.

It is additionally noted and anticipated that although the device is shown in its most simple form, various components and aspects of the device may be differently shaped or slightly modified when forming the invention herein. As such those skilled in the art will appreciate the descriptions and depictions set forth in this disclosure or merely meant to portray examples of preferred modes within the overall scope and intent of the invention, and are not to be considered limiting in any manner. While all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the scope of the invention.

Moreover, references to the device, maneuver, method, and system are meant to reference the utilization of one or more of the device, maneuver, method, and system of the current invention, individually or combined with the other components and not necessarily the utilization of all of the components.

While various embodiments of the system have been described in detail, it is apparent that modifications and alterations of those embodiments will occur to those skilled in the art. It is to be expressly understood that such modifications and alterations are within the scope and spirit of the present disclosure. Further, it is to be understood that the phraseology and terminology used herein is for the purposes of description and should not be regarded as limiting. The use of "including," "comprising," or "having" and variations thereof herein are meant to encompass the items listed thereafter and equivalents thereof, as well as, additional items.

What is claimed is:

1. A method of relaxation, comprising:
providing a device comprising an attaching component at a proximal end of the device, an extension element that is substantially rigid, and a handheld component at a distal end of the device;
inserting the attaching component at the proximal end of the device such that at least one contact surface of the attaching component is positioned on a user's bottom front teeth within a user's mouth without application of a force on the attaching component by the user with a user's jaw;
positioning the extension element of the device proximate to a user's chin, wherein the extension element extends from the attaching component in an outward and downward direction in a curvilinear shape from the user's mouth toward a distal end of the device beneath the user's chin; and
applying a force to the handheld component at the distal end of the device that is substantially aligned with the at least one contact surface of the attaching component, wherein the handheld component is fixedly coupled to the attaching component via the extension element, and wherein the force is transferred to the user's jaw in a direction along an axis of at least one of the user's bottom front teeth from the handheld component to the attaching component via the extension element to distract the user's jaw downward while the user is not applying a force on the attaching component with the user's jaw, thereby stretching and relaxing a user's jaw muscles and activating a user's parasympathetic nervous system to relax the user.

2. The method of relaxation of claim 1, further comprising:
performing the stretching and relaxing in a guided short meditative session that further relaxes the user.

3. The method of relaxation of claim 1, further comprising:
using a series of lessons to encourage lifestyle habit changes in one or more of the following domains: sleep, attitude, gratitude, movement, nutrition, and habit change strategies.

4. The method of relaxation of claim 1, further comprising:
relaxing the user to limit or prevent an occurrence of one or more of the following conditions: headaches, temporomandibular joint pain, neck aches, bruxism, tinnitus, insomnia, anxiety, and cognitive ability challenges.

5. The method of relaxation of claim 1, further comprising:
guiding the user in meditation and stretching through a program stored on a smartphone.

6. The method of relaxation of claim 1, further comprising:
entering emotional data and device usage data into a medium; and
analyzing the emotional data and the device usage data to create a program of future use.

7. The method of relaxation of claim 1, further comprising:
providing music, sound, or a guided meditation program through an application stored on a smartphone.

8. A method of reducing psychological stress and improving Heart Rate Variability utilizing a physiologic maneuver, the method comprising:
a. providing a device comprising a tooth-engaging end at a proximal end and a handle at a distal end, wherein the tooth-engaging end and the handle are connected via a substantially rigid and curvilinear extension element;
b. engaging at least one contact surface of the tooth-engaging end at the proximal end of the device with a user's bottom front teeth in a user's mouth;
c. gently pulling down on the handle at the distal end of the device positioned beneath a user's chin by the substantially rigid and curvilinear extension element such that a user's jaw is in a stretched open position while the user is not applying a force on the tooth-engaging end of the device with the user's bottom front teeth, wherein the handle is substantially aligned with the tooth-engaging end, and wherein a force applied by gently pulling down on the handle is in a direction along an axis of at least one of the user's bottom front teeth to trigger a user's parasympathetic nervous system while a user's jaw muscles are relaxed; and
d. holding the stretched open position of the user's jaw by pulling down on the handle of the device for a period of time.

9. The method of claim 8, wherein the period of time is between 30 and 60 seconds.

10. The method of claim 8, further comprising at least one of:
e. repeating steps b through d for a number of repetitions; and
f. playing a guided mediation that instructs the user when to perform one or more of steps b through d.

11. The method of claim 8, further comprising:
e. inhaling for approximately 5 seconds and exhaling for approximately 6 seconds simultaneously with step d.

12. A system for relaxation comprising:
a device comprising:
a tooth-engaging end that is substantially flat and at a proximal end of the device, wherein the tooth-engaging end includes a contact surface is positionable within a user's mouth without application of a force on the tooth engaging end by the user with a user's lower teeth within the user's mouth;
a handle having a loop at a distal end of the device;
a substantially rigid shaft connecting the handle and the tooth-engaging end, wherein the substantially rigid shaft extends in an outward and downward direction in a curvilinear shape from the user's mouth toward the distal end of the device such that a force applied to the handle is substantially aligned with the tooth-engaging end and an axis through at least one lower tooth of the user's lower teeth, and wherein at least one of:

the handle is positioned beneath a user's chin with the curvilinear shape of the substantially rigid shaft; and a chin pad is coupled to the substantially rigid shaft and operable to rest on the user's chin; and one or more of:

a computer program stored on a digital device having a display and a speaker, the computer program causing the digital device to output a visual via a display and/or output soothing sounds through a speaker;

a series of lessons or instructions delivered digitally to the user; and a means of digitally tracking a user's progress.

13. The system for relaxation of claim 12, wherein the soothing sounds are a guided meditation having instructions for stretching a user's jaw.

14. The system for relaxation of claim 12, wherein the visual is at least one lesson designed to reduce stressors in a user's life which address one or more of habit changes of sleep, attitude, gratitude, movement, dietary choices, and habit change strategies.

15. The system for relaxation of claim 12, wherein the visual contains one or more of a lesson to manage stress effectively, a message on how to prevent stress, and a video having different phases.

16. A method of providing immediate relaxation to a user using the system for relaxation of claim 12, the method comprising:

using the tooth-engaging end of the device to engage the user's lower teeth;

pulling down on the handle of the device, while the user is not applying a force on the tooth-engaging end of the device with the user's lower teeth, such that the user's mouth is held open and a user's parasympathetic nervous system is activated; and providing one or more of soothing noises, instructions for measured breathing, yawning, meditation, or a momentary disengagement of a current activity.

17. The system of claim 12, further comprising:

a cloud network that is in communication with the digital device; and, the cloud network configured to send the visual to be displayed and/or the soothing sounds to be output to the digital device.

18. A method of preventing or limiting a frequency of migraine headaches using the system for relaxation of claim 12, the method comprising:

a. using the tooth-engaging end of the device to engage a user's bottom teeth;

b. gently applying the force to the handle of the device by pulling down on the handle of the device in a direction along the axis of the at least one lower tooth of the user's lower teeth such that a user's jaw is in a stretched open position, while the user is not applying the force on the tooth-engaging end of the device with the user's bottom teeth, to trigger a user's parasympathetic nervous system while a user's jaw muscles are relaxed;

c. holding the stretched open position of the user's jaw by pulling down on the handle of the device for a period of time;

d. receiving reminders from the digital device to perform steps a through c; and e. providing strategies for avoiding migraine triggers by one or more of educational, motivational, and educational means.

\* \* \* \* \*